(12) United States Patent
Condon et al.

(10) Patent No.: US 8,022,230 B2
(45) Date of Patent: *Sep. 20, 2011

(54) DIMERIC IAP INHIBITORS

(75) Inventors: Stephen M. Condon, Glenmoore, PA (US); Matthew G. LaPorte, Honey Brook, PA (US); Yijun Deng, Dresher, PA (US); Susan R. Rippin, Wilmington (DE)

(73) Assignee: TetraLogic Pharmaceuticals Corporation, Malvern, PA (US)

( * ) Notice: Subject to any disclaimer, the term of this patent is extended or adjusted under 35 U.S.C. 154(b) by 133 days.

This patent is subject to a terminal disclaimer.

(21) Appl. No.: 12/403,915

(22) Filed: Mar. 13, 2009

(65) Prior Publication Data

US 2010/0075911 A1  Mar. 25, 2010

Related U.S. Application Data

(63) Continuation of application No. 11/363,387, filed on Feb. 27, 2006, now Pat. No. 7,517,906.

(60) Provisional application No. 60/656,201, filed on Feb. 25, 2005, provisional application No. 60/668,344, filed on Apr. 5, 2005, provisional application No. 60/692,111, filed on Jun. 20, 2005, provisional application No. 60/706,649, filed on Aug. 9, 2005, provisional application No. 60/729,853, filed on Oct. 25, 2005.

(51) Int. Cl.
C07D 209/12 (2006.01)

(52) U.S. Cl. ...................................... 548/494

(58) Field of Classification Search ................ 548/494
See application file for complete search history.

(56) References Cited

U.S. PATENT DOCUMENTS

| | | | |
|---|---|---|---|
| 3,832,253 A | 8/1974 | DiPalma et al. |
| 3,854,480 A | 12/1974 | Zaffaroni |
| 4,278,793 A | 7/1981 | Durckheimer et al. |
| 4,452,775 A | 6/1984 | Kent |
| 4,667,014 A | 5/1987 | Nestor, Jr. et al. |
| 4,748,034 A | 5/1988 | deRham |
| 5,075,109 A | 12/1991 | Tice et al. |
| 5,239,660 A | 8/1993 | Ooi |
| 5,660,811 A | 8/1997 | Mills |
| 5,766,572 A | 6/1998 | Hasegawa et al. |
| 6,110,691 A | 8/2000 | Wang et al. |
| 6,133,437 A | 10/2000 | Korneluk et al. |
| 6,187,557 B1 | 2/2001 | Rothe et al. |
| 6,338,835 B1 | 1/2002 | Shochat et al. |
| 6,608,026 B1 | 8/2003 | Wang et al. |
| 6,911,426 B2 | 6/2005 | Reed et al. |
| 6,992,063 B2 | 1/2006 | Shi et al. |
| 7,217,688 B2 | 5/2007 | Reed et al. |
| 7,244,851 B2 | 7/2007 | Cohen et al. |
| 7,309,792 B2 | 12/2007 | Harran et al. |
| 7,517,906 B2 * | 4/2009 | Condon et al. ............ 514/415 |
| 7,579,320 B2 | 8/2009 | Boudreault et al. |
| 7,589,118 B2 | 9/2009 | Laurent et al. |
| 7,718,600 B2 | 5/2010 | McLendon et al. |
| 7,807,699 B2 | 10/2010 | Hanson et al. |
| 2002/0132786 A1 | 9/2002 | Alnemri et al. |
| 2002/0160975 A1 | 10/2002 | Alnemri |
| 2002/0177557 A1 | 11/2002 | Shi |
| 2004/0054148 A1 | 3/2004 | Alnemri |
| 2005/0197403 A1 | 9/2005 | Harran et al. |
| 2005/0234042 A1 | 10/2005 | Palermo et al. |
| 2005/0261203 A1 | 11/2005 | Cohen et al. |
| 2006/0014700 A1 | 1/2006 | Cohen et al. |
| 2006/0025347 A1 | 2/2006 | Condon et al. |
| 2006/0052311 A1 | 3/2006 | Sharma et al. |
| 2006/0128632 A1 | 6/2006 | Sharma et al. |
| 2006/0167066 A1 | 7/2006 | Cohen et al. |
| 2006/0194741 A1 | 8/2006 | Condon et al. |
| 2006/0258581 A1 | 11/2006 | Reed et al. |
| 2006/0264379 A1 | 11/2006 | Jarvis et al. |
| 2007/0003535 A1 | 1/2007 | Reed et al. |
| 2007/0042428 A1 | 2/2007 | Springs et al. |
| 2007/0093428 A1 | 4/2007 | Laurent |
| 2007/0093429 A1 | 4/2007 | Laurent et al. |
| 2008/0269140 A1 | 10/2008 | Wang et al. |
| 2009/0005411 A1 | 1/2009 | Jensen et al. |
| 2009/0104151 A1 | 4/2009 | Hanson et al. |
| 2009/0123480 A1 | 5/2009 | Wang et al. |
| 2009/0142334 A1 | 6/2009 | Korneluk et al. |
| 2009/0192140 A1 | 7/2009 | Laurent et al. |
| 2010/0130539 A1 | 5/2010 | Koehler |

FOREIGN PATENT DOCUMENTS

WO  WO 99/15657  4/1999

(Continued)

OTHER PUBLICATIONS

Ambrosini et al., Induction of Apoptosis and Inhibition of Cell Proliferation by survivin Gene Targeting, 1998, J. Biol. Chem. 273(18):11177-11182. Ashhab et al., two splicing variants of a new inhibitor of apoptosis gene with different biological properties and tissue distribution pattern, 2001, FEBS Lett. 495:56-60.
Brunger, X-PLOR, a System for Crystallography and NMR, Yale University Press, New Haven, CT, 1991.
Craig et al., Modern Pharmacology with Clinical Applications, 6th Ed., Lippincott Williams & Wilkins, Philadelphia, pp. 639-656, 2004.
Chawla-Sarkar, Preferential Induction of Apoptosis by Interferon (IFN)-p Compared with IFN-432: Correlation with TRAIUApo2L Induction in Melanoma Cell Lines, 2001, Clin. Can. Res. 7:1821-1831.
Chai et al., Structural and biochemical basis of apoptotic activation by Smac/DIABLO, 2000, Nature 406:855-862.

(Continued)

Primary Examiner — Rei-tsang Shiao
(74) Attorney, Agent, or Firm — Banner & Witcoff, Ltd.

(57) ABSTRACT

Molecular mimics of Smac are capable of modulating apoptosis through their interaction with cellular IAPs (inhibitor of apoptosis proteins). The mimetics are based on a monomer or dimer of the N-terminal tetrapeptide of IAP-binding proteins, such as Smac/DIABLO, Hid, Grim and Reaper, which interact with a specific surface groove of IAP. Also disclosed are methods of using these peptidomimetics for therapeutic purposes. In various embodiments of the invention the Smac mimetics of the invention are combined with chemotherapeutic agents, including, but not limited to topoisomerase inhibitors, kinase inhibitors, NSAIDs, taxanes and platinum containing compounds use broader language.

1 Claim, 4 Drawing Sheets

FOREIGN PATENT DOCUMENTS

| WO | WO 02/16418 | 2/2002 |
|---|---|---|
| WO | WO 02/26775 | 4/2002 |
| WO | WO 02/30959 | 4/2002 |
| WO | WO 02/096930 | 12/2002 |
| WO | WO 03/018014 | 3/2003 |
| WO | WO 2004/005248 | 1/2004 |
| WO | WO 2004/007529 | 1/2004 |
| WO | WO 2004/072105 | 8/2004 |
| WO | WO 2005/069888 | 8/2005 |
| WO | WO 2005/069894 | 8/2005 |
| WO | WO 2005/078989 | 8/2005 |
| WO | WO 2005069888 | 8/2005 |
| WO | WO 2005074989 | 8/2005 |
| WO | WO 2005/084317 | 9/2005 |
| WO | WO 2005/094818 | 10/2005 |
| WO | WO 2005/097791 | 10/2005 |
| WO | WO 2006/010118 | 1/2006 |
| WO | 2006017295 | 2/2006 |
| WO | WO 2006/014361 | 2/2006 |
| WO | WO 2006/020060 | 2/2006 |
| WO | WO 2006/069063 | 6/2006 |
| WO | WO 2006/091972 | 8/2006 |
| WO | WO 2006/122408 | 11/2006 |
| WO | WO 2006/128455 | 12/2006 |
| WO | WO 2006/133147 | 12/2006 |
| WO | WO 2007/101347 | 9/2007 |
| WO | WO 2007/106192 | 9/2007 |
| WO | WO 2007/130626 | 11/2007 |
| WO | WO 2008016893 | 2/2008 |
| WO | WO 2008057172 | 5/2008 |
| WO | WO 2008134679 | 11/2008 |

OTHER PUBLICATIONS

Boxrud et al., Streptokinase Binds to Human Plasmin with High Affinity, Perturbs the Plasmin Active Site, and Induces Expression of a Substrate Recognition Exosite for Plasminogen, 2000, *J. Biol. Chem.* 275(19):14579-14589.

Chan et al., Fmoc Solid Phase Peptide Synthesis: A Practical Approach, 2000, Oxford University Press (TOC).

Chen et al., Grim, a novel cell death gene in drospohila, 1996, Genes & Devel. 10:1773-1782.

Chantalat et al., Crystal Structure of Human Survivin Reveals a Bow Tie-Shaped Dimer with Two Unusual a-Helical Extensions, 2000, *Mol. Cell.* 6:183-189.

Deveraux et al., IAP family proteins-suppressors of apoptosis, 1999, *Genes & Devel.* 13:239-252.

Du et al., Smac, a mitochondrial Protein that Promotes Cytochrome c-Dependent Caspase Activation by Eliminating IAP Inhibitiion, 2000, *Cell* 102:33-42.

Deveraux et al., Cleavage of human inhibitor of apoptosis protein XIAP results in fragments with distinct specificities for caspases, 1999, *EMBO J.* 18(19):5242-5251.

Fulda et al., Smac agonists sensitize for Apon/TRAIL-or anticancer drug-induced apoptosis and induce regression of malignant glioma in vivo, 2002, *Nat. Med.* 8(8):808-815.

Freidinger et al., Synthesis of 9pflourenylmethyloxycarbobyl-protected n-alkyl amino acids by reduction of oxazolidinones, 1983, *J. Org. Chem.* 48:77-81.

Hruby et al., Synthesis of oligopeptide and peptidomimetic libraries, 1997, Curr. Op. in Chem. Biol. 1:114-119.

Hruby et al., Conformational and Topographical Considerations in Designing Agonist Peptidomimetics from Peptide Leads, 2000, *Curr. Med. Chem.* 7(9):945-970.

Hay, Understanding IAP function and regulation: a view from Drosophila, 2000, Cell Death and Diff. 7:1045-1056.

Hiratsuka, ATP-induced Opposite Changes in the Local Environments around $Cys^{697}$(SH2) and Cys707(SH1) of the Myosin Motor Domain Revealed by the Prodan Fluorescence, 1999, *J. Biol. Chem.* 274(41):29156-29163.

Goyal et al., Induction of apoptosis by drosophila reaper, hid and grim through inhibition of IAP function, 2000, *EMBO J.* 19(4):589-597.

Hengartner, Programmed cell death in invertebrates, 1996, Curr. Opin. Genet. Dev. 6:34-38.

Horvitz, Genetic Control of Programmed Cell Death in the Nematode Caenorhabditis elegans, 1999, *Can. Res.* 59:1701s-1706s.

Hirel et al., Extent of N-terminal methionine excision from *Escherichia coli* proteins is governed by the side-chain length of the penultimate amino acid, 1989, *Proc. Natl. Acad. Sci. USA* 86:8247-8251.

Kohli et al., SMAC/Diablo-dependent apoptosis induced by nonsteroidal antiinflammatory drugs (NSAIDs) in colon cancer cells, 2004, PNAS 101(48):16897-16902.

Jacobson et al., Programmed Cell Death in Animal Development, 1997, *Cell* 88:347-354.

Jones et al., Improved methods for building protein models in electron density maps and the location of errors in these models, 1991, *Acta Crystallogr.* A47:110-119.

Kraulis, Molscript: a program to produce both detailed and schematic plots of protein structures, 1991, *J. Appl. Crystallogr.* 24:946-950.

Macor et al., The Synthesis of a Conformationally Restricted Analog of the Anti-Migraine Drug Sumatriptan, 1992, Tetrahedron Lett. 33(52):8011-8014.

Lang's Handbook of Chemistry, Dean ed., Table 7-2, 1985.

Lisi et al., Diverse Domains of THREAD/DIAPI are Required to Inhibit Apoptosis Induced by REAPER and HID in Drosophila, 1999, *Genetics Soc. Am.* 154:669-678.

Liu, Structural basis for binding of Smac/DIABLO to the XIAP BIR3 domain, Dec. 2000, *Nature*, pp. 1004-1008.

McCarthy et al., Apoptosis induced by drosophila reaper and grim in a human system, 1999, *J. Biol. Chem.* 273(37):24009-24015.

Morgan et al., Approaches to the Discovery of Non-Peptide Ligands for Peptide Receptors and Peptidases, 1989, *Ann. Rep. Med. Chem.* 243-252.

Miller, An exegesis of IAPs: salvation and surprises from BIR motifs, 1999, Cell Biol. 9:323-328.

Owenius et al., Properties of Spin and Fluorescent Labels at a Receptor-Ligand Interface, 1999, *Biophys. J.* 77:2237-2250.

Navaza, AmoRe: an Automated Package for Molecular Replacement, 1994, Acta Cryst. A50:157-163.

Nicholls et al., Protein folding and association: insights from the interfacial and thermodynamic properties of hydrocarbons, 1991, Proteins: Struct. Funct. & Genet. 11:281-296.

Oost et al., Discovery of Potent Antagonists of the Antiapoptotic Protein XIAP for the Treatment of Cancer, 2004.

Park et al., Non-peptide small molecule inhibitors of XIAP, 2004, *Bioorganic & Med. Chem. Lett.* 15:771-775.

Ripka et al., Peptidomimetic design, 1998, *Curr. Op. Chem. Biol.* 2:441-452.

Nikolovska-Coleska et al., Development and optimization of a binding assay for the XIAP BIR3 domain using fluorescence polarization, 2004, *Anal. Biochem.* 332:261-273.

Sun et al., Structure-based Design of Potent, Conformationally Constrained Smac Mimetics, 2004, *J. Am. Chem. Soc.* 126:16686-16687.

Srinivasula et al., A conserved XIAP-interaction motif in caspase-9 and Smac/DIABLO regulates caspase activity and apoptosis, 2001, *Nature* 410:112-116.

Sun et al., NMR Structure and Mutagenesis of the Third Bir Domain of the Inhibitor of Apoptosis Protein XIAP, 2000, *J. Biol. Chem.* 275(43):33777-33781.

Stellar, Mechanisms and Genes of Cellular Suicide, 1995, *Science* 267:1445-1449.

Sun et al., NMR structure and mutagenesis of the inhibitor-of-apoptosis protein XIAP, 1999, *Nature* 40:818-822.

Shi, Survivin structure: crystal unclear, 2000, *Nat. Str. Biol.* 7(8):620-623.

Srinivasula et al., Molecular Determinants of the Caspase-promoting activity of Smac/DIABLO and its role in the death receptor pathway, 2000, *J. Biol. Chem.* 275(46):36152-36157.

Terwilliger et al., The CCP4 suite: Programs for protein crystallography, 1994, Acta Crystallogr. D50:760-763.

Terwilliger et al., Correlated Phasing of Multiple Isomorphous Replacement Data, 1996, Acta Cnystallogr. D52:749-757.

Takahashi et al., A Single BIR Domain XIAP Sufficient for Inhibiting Caspases, 1998, *J. Biol. Chem.* 273(14):7787-7790.

Weinstein ed., Chemistry and Biochemistry of Amino Acids, Peptides, and Proteins, 1983, Marcel Dekker, Inc., New York, New York (TOC).

Wyllie et al., Cell Death: the significance of apoptosis, 1980, Int. Rev. Cytol. 68:251-306.

Vvyllie, Glucocorticoid-induced thymocyte apoptosis is associated with endogenous endonuclease activation, 1981, Nature 284:555-556.

Wu et al., Structural basis of IAP recognition by Smac/DIABLO, 2000, Nature 408:1008-1012.

Wu et al., Structural Analysis of a Functional DIAP1 Fragment Bound to Grim and Hid Peptides, 2001, Mol. Cell 8:95-104.

Vucic et al., ML-IAP, a novel inhibitor of apoptosis that is preferentially expressed in human melanomas, 2000, Curr. Biol. 10:1359-1366.

Verhagen et al., Identification of DIABLO, a Mammalian Protein that Promotes Apoptosis by Binding to and Antagonizing IAP Proteins, 2000, Cell 102:43-53.

Vucic et al., Inhibition of Reaper-induced apoptosis by interaction with inhibitor of apoptosis proteins (IAPS), 1997, Proc. Natl. Acad. Sci. USA 94:10183-10188.

Verdecia et al. Structure of the human anti-apoptotic protein surviving reveals a dimeric arrangement, 2000, Nat. Struc. Biol. 7(7):602-608.

Wang et al., The Drosphila Caspase Inhibitor DIAP1 is Essential for Cell Survival and Is Negatively Regulated by HID, 1999, Cell 98:453-463.

Vucic et al., Engineering ML-IAP to produce an extraordinarily potent caspase 9 inhibitor: implications for Smac-dependent anti-apoptotic activity of ML-IAP, 2005, Biochem. J. 385(1):11-20.

Zuckerman et al., Efficient Method for the Preparation of Peptoids [Oligo(N-substituted glycines)] by Submonomer Solid-Phase Synthesis, 1992, J. Am. Chem. Soc. 114:10646-10647.

Kasof et al., Livin, a Novel Inhibitor of Apoptosis Protein Family Member, 2001, J. Biol. Chem. 276(5):3238-3246.

Hansen et al., Re-examination and further development of a precise and rapid dye method for measuring cell growth/cell kill, 1989, J. Immunol. Methods, 119:203-210.

Bockbrader et al., "A small molecule Smac-mimic compound induces apoptosis and sensitizes TRAIL-and etoposide-induced apoptosis in breast cancer cells," Oncogene, 2005, vol. 24, No. 49, pp. 7381-7388.

Fotin-Mleczek et al., "Cationic cell-penetrating peptides interfere with TNF signalling by induction of TNF receptor internalization," Journal of Cell Science, 2005, vol. 118, No. 15, pp. 3339-3351.

* cited by examiner

DIMERIC IAP INHIBITORS

CROSS REFERENCES AND RELATED APPLICATIONS

This application is a continuation application of U.S. application Ser. No. 11/363,387 entitled DIMERIC IAP INHIBITORS filed on Feb. 27, 2006 now U.S. Pat. No. 7,517,906, which claims priority from U.S. Provisional Application No. 60/656,201 entitled "PEPTIDOMIMETICS" filed on Feb. 25, 2005, U.S. Provisional Application No. 60/668,344 entitled "IMMUNOTHERAPEUTIC USES OF SMAC MIMETICS" filed on Apr. 5, 2005, U.S. Provisional Application No. 60/692,111 entitled "PEPTIDOMIMETICS OF SMAC ALONE OR IN COMBINATION WITH TOPOISOMERASE INHIBITORS" filed on Jun. 20, 2005, U.S. Provisional Application No. 60/706,649 entitled "PEPTIDOMIMETICS OF SMAC AS CAP INHIBITORS" filed on Aug. 9, 2005 and U.S. Provisional Application No. 60/729,853 entitled "PEPTIDOMIMETICS OF SMAC ALONE OR IN COMBINATION WITH PLATINUM CONTAINING COMPOUNDS AND TAXANES" filed on Oct. 25, 2005 all of which are herein incorporated by reference in their entireties.

BACKGROUND

Apoptosis (programmed cell death) plays a central role in the development and homeostasis of all multi-cellular organisms. Apoptosis can be initiated within a cell from an external factor such as a chemokine (an extrinsic pathway) or via an intracellular event such as DNA damage (an intrinsic pathway). Alterations in apoptotic pathways have been implicated in many types of human pathologies, including developmental disorders, cancer, autoimmune diseases, as well as neurodegenerative disorders. One mode of action of chemotherapeutic drugs is cell death via apoptosis.

Apoptosis is conserved across species and executed primarily by activated caspases, a family of cysteine proteases with aspartate specificity in their substrates. These cysteine containing aspartate specific proteases) ("caspases") are produced in cells as catalytically inactive zymogens and are proteolytically processed to become active proteases during apoptosis. Once activated, effector caspases are responsible for proteolytic cleavage of a broad spectrum of cellular targets that ultimately lead to cell death. In normal surviving cells that have not received an apoptotic stimulus, most caspases remain inactive. If caspases are aberrantly activated, their proteolytic activity can be inhibited by a family of evolutionarily conserved proteins called IAPs (inhibitors of apoptosis proteins).

The IAP family of proteins suppresses apoptosis by preventing the activation of procaspases and inhibiting the enzymatic activity of mature caspases. Several distinct mammalian IAPs including XIAP, c-IAP1, c-IAP2, ML-IAP, NAIP (neuronal apoptosis inhibiting protein), Bruce, and survivin, have been identified, and they all exhibit anti-apoptotic activity in cell culture. IAPs were originally discovered in baculovirus by their functional ability to substitute for P35 protein, an anti-apoptotic gene. IAPs have been described in organisms ranging from Drosophila to human, and are known to be overexpressed in many human cancers. Generally speaking, IAPs comprise one to three Baculovirus LAP IAP repeat (BIR) domains, and most of them also possess a carboxyl-terminal RING finger motif. The BIR domain itself is a zinc binding domain of about 70 residues comprising 4 alpha-helices and 3 beta strands, with cysteine and histidine residues that coordinate the zinc ion. It is the BIR domain that is believed to cause the anti-apoptotic effect by inhibiting the caspases and thus inhibiting apoptosis. XIAP is expressed ubiquitously in most adult and fetal tissues. Overexpression of XIAP in tumor cells has been demonstrated to confer protection against a variety of pro-apoptotic stimuli and promotes resistance to chemotherapy. Consistent with this, a strong correlation between XIAP protein levels and survival has been demonstrated for patients with acute myelogenous leukemia. Down-regulation of XIAP expression by antisense oligonucleotides has been shown to sensitize tumor cells to death induced by a wide range of pro-apoptotic agents, both in vitro and in vivo. Smac/DIABLO-derived peptides have also been demonstrated to sensitize a number of different tumor cell lines to apoptosis induced by a variety of pro-apoptotic drugs.

In normal cells signaled to undergo apoptosis, however, the IAP-mediated inhibitory effect must be removed, a process at least in part performed by a mitochondrial protein named Smac (second mitochondrial activator of caspases). Smac (or, DIABLO), is synthesized as a precursor molecule of 239 amino acids; the N-terminal 55 residues serve as the mitochondria targeting sequence that is removed after import. The mature form of Smac contains 184 amino acids and behaves as an oligomer in solution. Smac and various fragments thereof have been proposed for use as targets for identification of therapeutic agents.

Smac is synthesized in the cytoplasm with an N-terminal mitochondrial targeting sequence that is proteolytically removed during maturation to the mature polypeptide and is then targeted to the inter-membrane space of mitochondria. At the time of apoptosis induction, Smac is released from mitochondria into the cytosol, together with cytochrome c, where it binds to IAPs, and enables caspase activation, therein eliminating the inhibitory effect of IAPs on apoptosis. Whereas cytochrome c induces multimerization of Apaf-1 to activate procaspase-9 and -3, Smac eliminates the inhibitory effect of multiple IAPs. Smac interacts with essentially all IAPs that have been examined to date including XIAP, c-IAP1, c-IAP2, and ML-IAP. Thus, Smac appears to be a master regulator of apoptosis in mammals.

It has been shown that Smac acts as an IAP antagonist promoting not only the proteolytic activation of procaspases, but also the enzymatic activity of mature caspase, both of which depend upon its ability to interact physically with IAPs. X-ray crystallography has shown that the first four amino acids (AVPI) of mature Smac bind to a portion of IAPs. This N-terminal sequence is essential for binding IAPs and blocking their anti-apoptotic effects.

The basic biology IAP antagonists suggest that they may complement or synergize other chemotherapeutic/anti-neoplastic agents and/or radiation. Chemotherapeutic/anti-neoplastic agents and radiation would be expected to induce apoptosis as a result of DNA damage and/or the disruption of cellular metabolism.

Current trends in cancer drug design focus on selective activation of apoptotic signaling pathways within tumors while sparing normal cells. The tumor specific properties of specific antitumor agents, such as TRAIL have been reported. The tumor necrosis factor-related apoptosis-inducing ligand (TRAIL) is one of several members of the tumor necrosis factor (TNF) superfamily that induce apoptosis through the engagement of death receptors. TRAIL interacts with an unusually complex receptor system, which in humans comprises two death receptors and three decoy receptors. TRAIL has been used as an anti-cancer agent alone and in combination with other agents including chemotherapeutic drugs and ionizing radiation. TRAIL can initiate apoptosis in cells that overexpress the survival factors Bcl-2 and Bcl-XL, and may represent a treatment strategy for tumors that have acquired resistance to chemotherapeutic drugs. TRAIL binds its cognate receptors and activates the caspase cascade utilizing adapter molecules such as FADD. Currently, five TRAIL receptors have been identified. Two receptors TRAIL-R1 (DR4) and TRAIL-R2 (DR5) mediate apoptotic signaling, and three non-functional receptors, DcR1, DcR2, and osteoprotegerin (OPG) may act as decoy receptors. Agents that increase expression of DR4 and DR5 may exhibit synergistic anti-tumor activity when combined with TRAIL.

The beneficial effects of TRAIL production have been shown in several types of cancer. For example, intravesical instillation of the BCG vaccine induces a Th1 immune response, resulting in the production of anti-tumor cytokines, including TRAIL, and the infiltration of the lesion with immune cell and is the first line of therapy for the treatment of superficial bladder cancer. In vitro studies indicate that interferon alpha (INF-α), which in currently being tested in clinical studies for efficacy in bladder cancer, causes apoptosis mediated by the autocrine production of TRAIL in human bladder cancer cell lines. The circulating level of osteoprotegerin, a decoy receptor for TRAIL, is also increased in patients with bladder cancer and negatively correlate with tumor stage, grade and prognosis.

Moreover, it has been shown that TRAIL expression by NK (Natural Killer) cells is enhanced by IL-2 (Interleukin 2) treatment, and the expression of TRAIL is required for full tumor cell cytotoxic effects. IL-2, a cytokine, is currently approved for the treatment of both melanoma and renal cell carcinoma.

Inhibition of cancer cell replication and/or DNA damage repair will enhance nuclear DNA fragmentation, thus inducing the cell to enter the apoptotic pathway. Topoisomerases, a class of enzymes that reduce supercoiling in DNA by breaking and rejoining one or both strands of the DNA molecule, are vital to cellular processes, such as DNA replication and repair. Inhibition of this class of enzymes impairs the cells ability to replicate as well as to repair damaged DNA and activates the intrinsic apoptotic pathway.

The main pathways leading from topoisomerase-mediated DNA damage to cell death involve activation of caspases in the cytoplasm by proapoptotic molecules released from mitochondria, such as Smac. The engagement of these apoptotic effector pathways is tightly controlled by upstream regulatory pathways that respond to DNA lesions-induced by topoisomerase inhibitors in cells undergoing apoptosis. Initiation of cellular responses to DNA lesions-induced by topoisomerase inhibitors is ensured by protein kinases that bind to DNA breaks. These kinases (non-limiting examples of which include Akt, JNK and P38) commonly called "DNA sensors" mediate DNA repair, cell cycle arrest and/or apoptosis by phosphorylating a large number of substrates, including several downstream kinases.

Platinum chemotherapy drugs belong to a general group of DNA modifying agents. DNA modifying agents may be any highly reactive chemical compound that bonds with various nucleophilic groups in nucleic acids and proteins and cause mutagenic, carcinogenic, or cytotoxic effects. DNA modifying agents work by different mechanisms, disruption of DNA function and cell death; DNA damage/the formation of crossbridges or bonds between atoms in the DNA; and induction of mispairing of the nucleotides leading to mutations, to achieve the same end result. Three non-limiting examples of platinum containing DNA modifying agents are cisplatin, carboplatin and oxaliplatin.

Cisplatin is believed to kill cancer cells by binding to DNA and interfering with its repair mechanism, eventually leading to cell death. Carboplatin and oxaliplatin are cisplatin derivatives that share the same mechanism of action. Highly reactive platinum complexes are formed intracellularly and inhibit DNA synthesis by covalently binding DNA molecules to form intrastrand and interstrand DNA crosslinks.

Non-steroidal anti-inflammatory drugs (NSAIDs) have been shown to induce apoptosis in colorectal cells. NSAIDS appear to induce apoptosis via the release of Smac from the mitochondria (PNAS, Nov. 30, 2004, vol. 101:16897-16902). Therefore, the use of NSAIDs in combination with Smac mimetics would be expected to increase the activity each drug over the activity of either drug independently.

U.S. Pat. No. 6,992,063 to Shi et al. entitled "Compositions and method for Regulating Apoptosis" filed on Sep. 28, 2001 and issued on Jan. 31, 2006, herein incorporated by reference in its entirety, teaches that mimetics of the N terminal portion of Smac provide viable drug candidates.

Additionally, it has been shown in U.S. application Ser. No. 10/777,946 to McLendon et al. entitled "IAP-Binding Cargo Molecules and Peptidomimetics For Use In Diagnostic and Therapeutic Methods" filed on Feb. 12, 2004, herein incorporated by reference in its entirety, that a cargo molecule can be attached to a N-terminal Smac tetrapeptide peptidomimetic.

SUMMARY OF THE INVENTION

The present invention provides compounds which mimic the tertiary binding structure of Smac to IAPs or activity of the N-terminal portion of Smac. Stereoisomers of the mimetic compounds described herein are also encompassed in the present invention. The invention also provides methods of using these mimetics to modulate apoptosis and further for therapeutic purposes. The invention also provides intermediates and methods for using these intermediates for the preparation of compounds which modulate apoptosis by mimicking the tertiary binding structure of Smac to IAPs or activity of the N-terminal portion of Smac.

A compound of the present invention having the general formula (I):

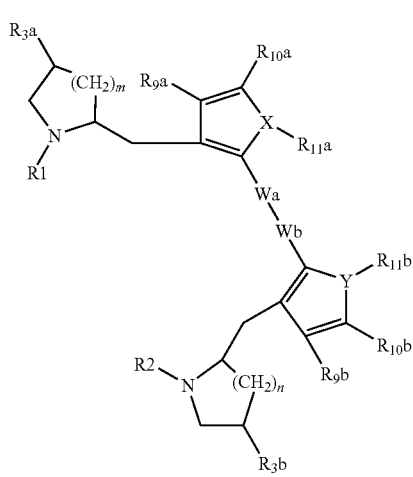

wherein R1 and R2 are independently H, tert-butoxycarbonyl, benzyloxycarbonyl, acetyl, trifluoroacetyl, alkyl, optionally-substituted alkyl, or

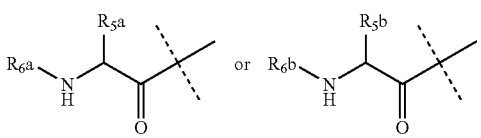

where R5a and R5b are independently H, alkyl, cycloalkyl, cycloalkylalkyl, heterocycloalkyl, aryl, arylalkyl, heteroaryl, heteroarylalkyl; or each optionally-substituted with hydroxyl, mercapto, halogen, amino, carboxyl, alkyl, haloalkyl, alkoxy, or alkylthio or R5a and R5b are independently optionally-substituted with hydroxyl, mercapto, halogen, amino, carboxyl, alkyl, haloalkyl, alkoxy, or alkylthio; or, optionally, R5a and R5b are connected by an alkylene, alkenylene, alkynylene bridge of 2 to 12 carbon atoms or an optionally-substituted alkylene, alkenylene, alkynylene bridge of 2 to 12 carbon atoms where one or more carbon atoms are replaced with N, O, or S;

R6a and R6b are independently H, tert-butoxycarbonyl, benzyloxycarbonyl, acetyl, trifluoroacetyl, alkyl, lower alkyl, optionally-substituted alkyl, or

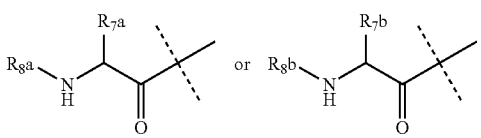

where R7a and R7b are independently H, alkyl, cycloalkyl, haloalkyl; or R8a and R7a and R8b and R7b can independently or together form a ring such as an aziridine or azetidine ring;

R8a and R8b are independently H, hydroxyl, alkyl, aryl, arylalkyl, cycloalkyl, cycloalkylalkyl, heteroaryl, or heteroarylalkyl wherein each alkyl, aryl, arylalkyl, cycloalkyl, cycloalkylalkyl, heteroaryl, and heteroarylalkyl is optionally-substituted with halogen, hydroxyl, mercapto, carboxyl, alkyl, alkoxy, amino, and nitro; or R8a and R7a and R8b and R7b can independently or together form a ring such as an aziridine or azetidine ring;

R3a and R3b are independently H, halogen, alkyl, aryl, arylalkyl, amino, arylamino, arylalkylamino, hydroxy, alkyloxy, aryloxy, arylalkylhydroxy, dialkylamino, amido, sulfonamido, or amidino;

m and n are independently 0, 1, 2, or 3;

X and Y are independently O, N, S, or C=C; and

R9a, R9b, R10a, R10b are independently H, alkyl, optionally-substituted alkyl, aryl, heteroaryl, optionally-substituted aryl, heteroaryl, or R9a and R10a, independently or in parallel with R9b and R10b, can be linked by 4 to 8 optionally-substituted atoms such as C, N, O, or S, to form an aromatic or non-aromatic ring; and when Wa and Wb are covalently bound, Wa and Wb are a bond, alkylene, alkenylene, alkynylene, aryl, arylalkylene, arylalkylalkylene, heteroaryl, heteroarylalkylene, or an optionally-substituted alkylene, alkenylene, alkynylene chain of 2 to 12 carbon atoms where one or more carbon atoms are replaced with N, O, or S; and R11a and R11b are independently absent, H, alkyl, optionally-substituted alkyl, hydroxyalkyl, alkoxyalkyl; or R11a and R11b together form an alkylene, alkenylene, alkynlyene, or alkyloxyalkylene chain of 2 to 12 carbon atoms where one or more carbon atoms are optionally replaced with N, O, or S;

When Wa and Wb are not covalently bound, Wa and Wb are independently be H, Cl, Br, F, alkyl, CN, $CO_2H$; and R11a and R11b together form an alkylene, alkenylene, alkynylene, or alkyloxyalkylene chain of 2 to 12 carbon atoms or an optionally substituted alkylene, alkenylene, alkynylene, or alkyloxyalkylene chain of 2 to 12 carbon atoms where one or more carbon atoms are optionally replaced with N, O, or S; or Wa is H, Cl, Br, F, alkyl, CN, $CO_2H$ and Wb and R11a together are a bond, alkylene, alkenylene, alkynylene, aryl, arylalkylene, arylalkylalkylene, heteroaryl, heteroarylalkylene, or an optionally-substituted alkylene, alkenylene, alkynylene chain of 2 to 12 carbon atoms where one or more carbon atoms can be replaced with N, O, or S, and R11b is absent or H, alkyl, optionally-substituted alkyl, hydroxyalkyl, alkoxyalkyl.

Another embodiment of the present invention is the therapeutic combination of compounds of the present invention with TRAIL or other chemical or biological agents which bind to and activate the TRAIL receptor(s). TRAIL has received considerable attention recently because of the finding that many cancer cell types are sensitive to TRAIL-induced apoptosis, while most normal cells appear to be resistant to this action of TRAIL. TRAIL-resistant cells may arise by a variety of different mechanisms including loss of the receptor, presence of decoy receptors, or overexpression of FLIP which competes for zymogen caspase-8 binding during DISC formation. In TRAIL resistance, Smac mimetics increase tumor cell sensitivity to TRAIL leading to enhanced cell death, the clinical correlations of which are expected to be increased apoptotic activity in TRAIL resistant tumors, improved clinical response, increased response duration, and ultimately, enhanced patient survival rate. In support of this, reduction in XIAP levels by in vitro antisense treatment has been shown to cause sensitization of resistant melanoma cells and renal carcinoma cells to TRAIL (Chawla-Sarkar, et al., 2004). The Smac mimetics disclosed herein bind to IAPs and inhibit their interaction with caspases, therein potentiating TRAIL-induced apoptosis.

In another embodiment of the invention, Smac mimetics are used in combination with BCG vaccine treatment of bladder cancer. XIAP, the nominal target of Smac mimetics, is overexpressed in a high proportion of bladder cancers. In studies using antisense XIAP, bladder cancer cells were sensitized to chemotherapeutic agents inducing apoptosis of effected cells through the TRAIL pathway. The present invention provides Smac mimetics for use with BCG therapy in superficial bladder cancer/carcinoma in situ. The Smac mimetics disclosed herein will enhance the effects of BCG vaccine by enhancing the effects if TRAIL generated in response to the vaccine.

Similarly, Smac mimetics will augment the TRAIL induced apoptosis observed in melanoma and renal cell carcinoma patients being treated with IL-2. Since IL-2 induces NK cell activity enhancing TRAIL expression, the addition of treatment with a caspase-9 activator, such as Smac mimetic, will lead to a more efficious clinical response.

Another embodiment of the present invention provides Smac mimetics which act synergistically with topoismerase inhibitors to potentiate their apoptotic inducing effect. Topoisomerase inhibitors inhibit DNA replication and repair, thereby promoting apoptosis and have been used as chemothemotherapeutic agents. Topoisomerase inhibitors promote DNA damage by inhibiting the enzymes that are required in the DNA repair process. Therefore, export of cytochrome c and Smac from the mitochondria into the cell cytosol is induced by the DNA damage caused by topoisomerase inhibitors.

Topoisomerase inhibitors of both the Type I class (camptothecin, topotecan, SN-38, irinotecan, topotecan, BNP 1350, 9-amino-camptothecan, lurtotecan, grimatecan, exatecan, amsacrine, and diflomotecan) and the Type II class (etoposide, anthracycyline, anthraquinone, and podophyllotoxin) show potent synergy with the Smac mimetics of the invention in a multi-resistant glioblastoma cell line (T98G), breast cancer line (MDA-MB-231), and ovarian cancer line (OVCAR-3) among others. Other topoisomerase inhibitors include, for example, Aclacinomycin A, camptothecin, daunorubicin, doxorubicin, ellipticine, epirubicin, and mitaxantrone.

In another embodiment of the invention, the chemotherapeutic/anti-neoplastic agent may be a platinum containing compound. In one embodiment of the invention the platinum containing compound is cisplatin. Cisplatin can synergize with a Smac peptidomimetic and potentiate the inhibition of an IAP, such as but not limited to XIAP, cIAP-1, c-IAP-2, ML-IAP, etc. In another embodiment a platinum containing compound is carboplatin. Carboplatin can synergize with a Smac peptidomimetic and potentiate the inhibition of an IAP, including, but not limited to, XIAP, cIAP-1, c-IAP-2, ML-IAP, etc. In another embodiment a platinum containing compound is oxaliplatin. The oxaliplatin can synergize with a Smac peptidomimetic and potentiate the inhibition of an IAP, including, but not limited to, XIAP, cIAP-1, c-IAP-2, ML-IAP, etc.

In another embodiment of the invention, the chemotherapeutic/anti-neoplastic agent that synergizes with a compound according to the present invention is a taxane. Taxanes are anti-mitotic, mitotic inhibitors or microtubule polymerization agents. Taxanes include but are not limited to, docetaxel and paclitaxel.

Taxanes are characterized as compounds that promote assembly of microtubules by inhibiting tubulin depolymerization, thereby blocking cell cycle progression through centrosomal impairment, induction of abnormal spindles and suppression of spindle microtubule dynamics. The unique mechanism of action of taxane is in contrast to other microtubule poisons, such as Vinca alkaloids, colchicine, and cryptophycines, which inhibit tubulin polymerization. Microtubules are highly dynamic cellular polymers made of $\alpha\beta$-tubulin and associated proteins that play key roles during mitosis by participating in the organization and function of the spindle, assuring the integrity of the segregated DNA. Therefore, they represent an effective target for cancer therapy.

In another embodiment, any agent that activates the intrinsic apoptotic pathway and/or causes the release of Smac or cytochrome c from the mitochondria has the potential to act synergistically with a Smac mimetic.

A combination of a Smac peptidomimetic and a chemotherapeutic/anti neoplastic agent and/or radiation therapy of any type that activates the intrinsic or extrinsic pathways or the release of Smac may provide a more effective approach to destroying tumor cells. Smac peptidomimetics interact with IAP's, such as XIAP, cIAP-1, cIAP-2, ML-IAP, etc., and block the IAP mediated inhibition of apoptosis while chemotherapeutics/anti neoplastic agents and/or radiation therapy kills actively dividing cells by activating the intrinsic apoptotic pathway leading to apoptosis and cell death. As is described in more detail below, embodiments of the invention provide combinations of a Smac pepidomimetc and a chemotherapeutic/anti-neoplastic agent and/or radiation which provide a synergistic action against unwanted cell proliferation. This synergistic action between a Smac peptidomimetic and a chemotherapeutic/anti-neoplastic agent and/or radiation therapy can improve the efficiency of the chemotherapeutic/anti-neoplastic agent and/or radiation therapy. This will allow for an increase in the effectiveness of current chemotherapeutic/anti-neoplastic agents or radiation treatment allowing the dose of the chemotherapeutic/anti-neoplastic agent to be lowered, therein providing both a more effective dosing schedule as well as a more tolerable dose of chemotherapeutic/anti-neoplastic agent and/or radiation therapy.

For simplicity and illustrative purposes, the principles of the invention are described by referring mainly to an embodiment thereof. In addition, in the following description, numerous specific details are set forth in order to provide a thorough understanding of the invention. It will be apparent however, to one of ordinary skill in the art, that the invention may be practiced without limitation to these specific details. In other instances, well known methods and structures have not been described in detail so as not to unnecessarily obscure the invention.

DETAILED DESCRIPTION

Figure 1:
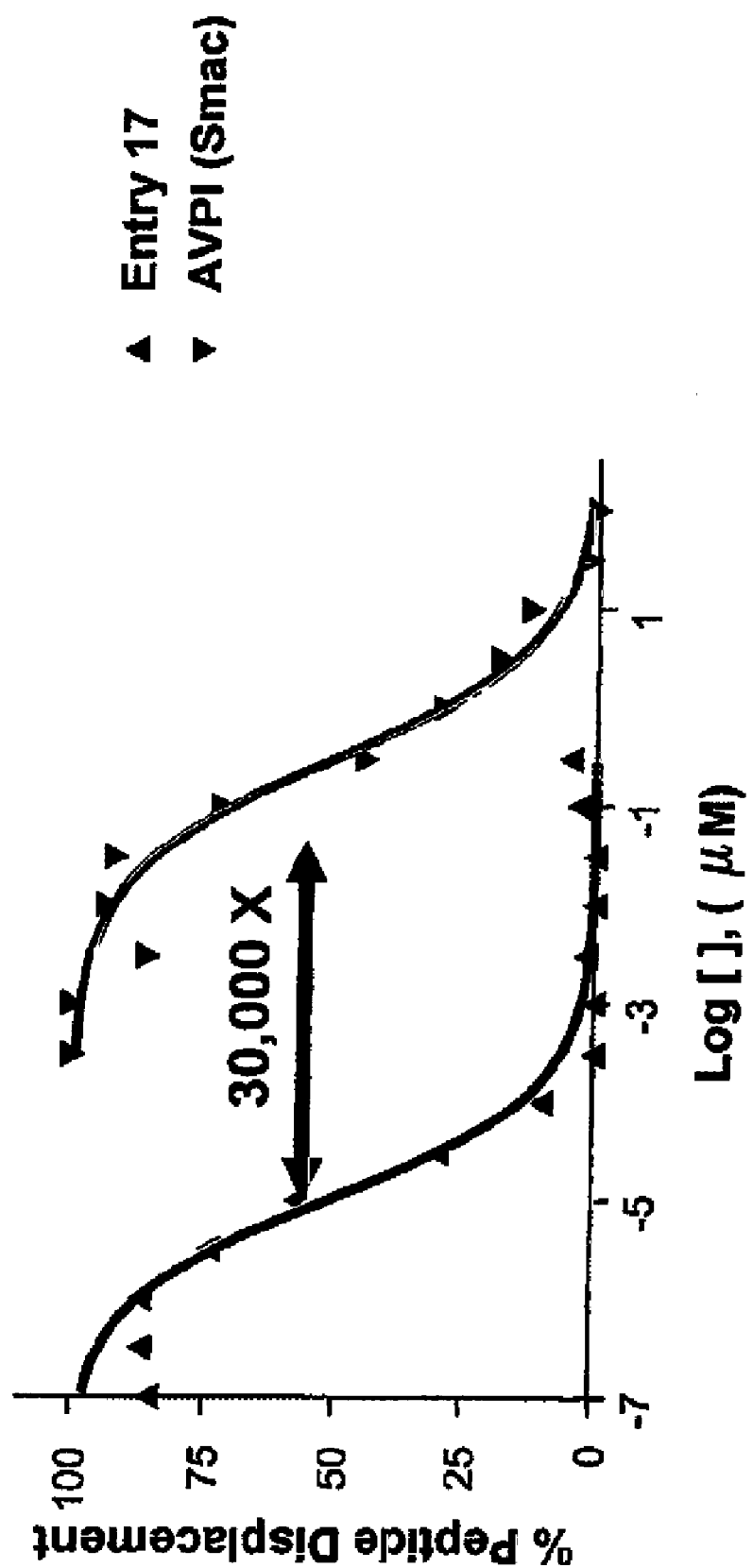
FIG. 1 is a graph depicting the relative binding affinity of a Smac tetrapeptide (AVPI) and a potent Smac mimetic of the present invention to XIAP BIR-3 using a fluorescence polarization assay. Results showed a 30,000 fold increase in binding affinity of the Smac mimetic relative to the Smac tetrapeptide.

It must also be noted that as used herein and in the appended claims, the singular forms "a", "an", and "the" include plural reference unless the context clearly dictates otherwise. Unless defined otherwise, all technical and scientific terms used herein have the same meanings as commonly understood by one of ordinary skill in the art. Although any methods similar or equivalent to those described herein can be used in the practice or testing of embodiments of the present invention, the preferred methods are now described. All publications and references mentioned herein are incorporated by reference. Nothing herein is to be construed as an admission that the invention is not entitled to antedate such disclosure by virtue of prior invention.

As used herein, the term "about" means plus or minus 10% of the numerical value of the number with which it is being used. Therefore, about 50% means in the range of 45%-55%.

"Alkyl" means a branched or unbranched, saturated or unsaturated (i.e. alkenyl, alkynyl)aliphatic hydrocarbon group, having up to 12 carbon atoms unless otherwise specified. When used as part of another term, for example "alkylamino", the alkyl portion may be a saturated hydrocarbon chain, however also includes unsaturated hydrocarbon carbon chains such as "alkenylamino" and "alkynylamino". Examples of particular alkyl groups include methyl, ethyl, n-propyl, isopropyl, n-butyl, iso-butyl, sec-butyl, tert-butyl, n-pentyl, 2-methylbutyl, 2,2-dimethylpropyl, n-hexyl, 2-methylpentyl, 2,2-dimethylbutyl, n-heptyl, 3-heptyl, 2-methylhexyl, and the like. The terms "lower alkyl" "C1-C4 alkyl" and "alkyl of 1 to 4 carbon atoms" are synonymous and used interchangeably to mean methyl, ethyl, 1-propyl, isopropyl, cyclopropyl, 1-butyl, sec-butyl or t-butyl. Unless specified, substituted, alkyl groups may contain one, two, three or four substituents which may be the same or different. Examples of the above substituted alkyl groups include, but are not limited to: cyanomethyl, nitromethyl, hydroxymethyl, trityloxymethyl, propionyloxymethyl, aminomethyl, carboxymethyl, carboxyethyl, carboxypropyl, alkyloxycarbonylmethyl, allyloxycarbonylaminomethyl, carbamoyloxymethyl, methoxymethyl, ethoxymethyl, t-butoxymethyl, acetoxymethyl, chloromethyl, bromomethyl, iodomethyl, trifluoromethyl, 6-hydroxyhexyl, 2,4-dichloro (n-butyl), 2-amino (iso-propyl), 2-carbamoyloxyethyl and the like. The alkyl group may also be substituted with a carbocycle group. Examples include cyclopropylmethyl, cyclobutylmethyl, cyclopentylmethyl, and cyclohexylmethyl groups, as well as the corresponding-ethyl, -propyl, -butyl, -pentyl, -hexyl groups, etc. Particular substituted alkyls are substituted methyls e.g. a methyl group substituted by the same substituents as the "substituted Cn-Cm alkyl" group. Examples of the substituted methyl group include groups such as hydroxymethyl, protected hydroxymethyl (e.g. tetrahydropyranyloxymethyl), acetoxymethyl, carbamoyloxymethyl, trifluoromethyl, chloromethyl, carboxymethyl, bromomethyl and iodomethyl.

"Amino" denotes primary (i.e. $-NH_2$), secondary (i.e. $-NRH$) and tertiary (i.e. $-NRR$) amines. Particular secondary and tertiary amines are alkylamine, dialkylamine, arylamine, diarylamine, arylalkylamine and diarylalkylamine. Particular secondary and tertiary amines are methylamine, ethylamine, propylamine, isopropylamine, phenylamine, benzylamine dimethylamine, diethylamine, dipropylamine and disopropylamine.

"Aryl" when used alone or as part of another term means a carbocyclic aromatic group whether or not fused having the number of carbon atoms designated or if no number is designated, up to 14 carbon atoms. Particular aryl groups include phenyl, naphthyl, biphenyl, phenanthrenyl, naphthacenyl, and the like (see e.g. Lang's Handbook of Chemistry (Dean, J. A., ed) 13$^{th}$ ed. Table 7-2 [1985]). In a particular embodiment an aryl group is phenyl. Substituted phenyl or substituted aryl denotes a phenyl group or aryl group substituted with one, two, three, four or five substituents chosen, unless otherwise specified, from halogen (F, Cl, Br, I), hydroxy, protected hydroxy, cyano, nitro, alkyl (such as C1-C6 alkyl), alkoxy (such as C1-C6 alkoxy), benzyloxy, carboxy, protected carboxy, carboxymethyl, protected carboxymethyl, hydroxymethyl, protected hydroxymethyl, aminomethyl, protected aminomethyl, trifluoromethyl, alkylsulfonylamino, arylsulfonylamino, heterocyclylsulfonylamino, heterocyclyl, aryl, or other groups specified. One or more methyne (CH) and/or methylene (CH2) groups in these substituents may in turn be substituted with a similar group as those denoted above. Examples of the term"substituted phenyl" includes but is not limited to a mono- or di(halo)phenyl group such as 2-chlorophenyl, 2-bromophenyl, 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono- or di(hydroxy)phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono- or di(lower alkyl)phenyl group such as 4-methylphenyl, 2,4-dimethylphenyl, 2-methylphenyl, 4-(iso-propyl)phenyl, 4-ethylphenyl, 3-(n-propyl) phenyl and the like; a mono or di(alkoxy)phenyl group, for example, 3,4-dimethoxyphenyl, 3-methoxy-4-benzyloxyphenyl, 3-methoxy-4-(1-chloromethyl)benzyloxy-phenyl, 3-ethoxyphenyl, 4-(isopropoxy)phenyl, 4-(t-butoxy)phenyl, 3-ethoxy-4-methoxyphenyl and the like; 3- or 4-trifluoromethylphenyl; a mono- or dicarboxyphenyl or (protected carboxy)phenyl group such 4-carboxyphenyl, a mono- or di(hydroxymethyl)phenyl or (protected hydroxymethyl)phenyl such as 3-(protected hydroxymethyl)phenyl or 3,4-di(hydroxymethyl)phenyl; a mono- or di (aminomethyl)phenyl or (protected aminomethyl)phenyl such as 2-(aminomethyl) phenyl or 2, 4-(protected aminomethyl)phenyl; or a mono- or di(N-(methylsulfonylamino))phenyl such as 3-(N-methylsulfonylamino))phenyl. Also, the term "substituted phenyl" represents disubstituted phenyl groups where the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, and the like, as well as trisubstituted phenyl groups where the substituents are different, for example 3-methoxy-4-benzyloxy-6-methyl sulfonylamino, 3-methoxy-4-benzyloxy-6-phenyl sulfonylamino, and tetra-substituted phenyl groups where the substituents are different such as 3-methoxy-4-benzyloxy-5-methyl-6-phenyl sulfonylamino. Particular substituted phenyl groups are 2-chlorophenyl, 2-aminophenyl, 2-bromophenyl, 3-methoxyphenyl, 3-ethoxy-phenyl, 4-benzyloxyphenyl, 4-methoxyphenyl, 3-ethoxy-4-benzyloxyphenyl, 3,4-diethoxyphenyl, 3-methoxy-4-benzyloxyphenyl, 3-methoxy-4-(1-chloromethyl) benzyloxy-phenyl, 3-methoxy-4-(1-chloromethyl)benzyloxy-6-methyl sulfonyl aminophenyl groups. Fused aryl rings may also be substituted with the substituents specified herein, for example with 1, 2 or 3 substituents, in the same manner as substituted alkyl groups.

The term alkylene radical as used herein includes reference to a di-functional saturated branched or unbranched hydrocarbon radical containing from 1 to 30 carbon atoms, and includes, for example, methylene ($CH_2$), ethylene ($CH_2CH_2$), propylene ($CH_2CH_2CH_2$), 2-methylpropylene ($CH_2CH$ ($CH_3$)$CH_2$), hexylene (($CH_2$)$_6$), and the like. Lower alkylene includes an alkylene group of 1 to 10, more preferably 1 to 5, carbon atoms.

Substituted alkylene radicals includes reference to a di-functional saturated branched or unbranched alkylene radical or group having 1-30 carbon atoms and having from 1 to 5 substituents. Lower substituted alkylene radicals refer to a substituted alkylene radical group, having 1-10 carbon atoms, preferably having 1-5 carbon atoms, and having from 1 to 5 substituents. Substituents can include but are not limited to those for the alkyl groups.

The term alkenyl radical as used herein includes reference to a branched, cyclic hydrocarbon, or unbranched hydrocarbon radical of 2 to 30 carbon atoms containing at least one carbon-carbon double bond, such as ethenyl, n-propenyl, iso-propenyl, n-butenyl, isobutenyl, t-butenyl, octenyl, decenyl, tetradecenyl, hexadecenyl, eicosenyl, tetracosenyl and the like. The term lower alkenyl includes an alkenyl group of 2 to 10 carbon atoms, preferably 2 to 5 carbon atoms, containing at least one carbon-carbon double bond. The one or more carbon-carbon double bonds may independently have a cis or trans configuration. Substituted alkenyl radical refers to an alkenyl radical or lower alkenyl group having from 1 to 5 substituents that can include but are not limited to those for the alkyl groups.

The term alkenylene radical includes reference to a difunctional branched or unbranched hydrocarbon radical or group containing from 2 to 30 carbon atoms and at least one carbon-carbon double bond. "Lower alkenylene" includes an alkenylene group of 2 to 10, more preferably 2 to 5, carbon atoms, containing one carbon-carbon double bond. Substituted alkenylene radical refers to an alkenylene radical or lower alkenyl group having from 1 to 5 substituents that can include but are not limited to those for the alkyl groups.

The term alkynyl radical or group refers to straight or branched chain hydrocarbon radical having 2 to 12 carbon atoms and at least one triple bond, some embodiments include alkynyl groups of 2 to 6 carbon atoms that have one triple bond. A substituted alkynyl will contain one, two, or three substituents as defined for substituted alkyl groups. Alkynylene includes reference to a difunctional branched or unbranched hydrocarbon chain containing from 2 to 12 carbon atoms and at least one carbon-carbon triple bond; some embodiments include an alkynylene groups of 2 to 6 carbon atoms with one triple bond. A substituted alkynylene will contain one, two, or three substituents as defined for substituted alkyl groups.

"Heterocyclic group", "heterocyclic", "heterocycle", "heterocyclyl", or "heterocyclo" alone and when used as a moiety in a complex group such as a heterocycloalkyl group, are used interchangeably and refer to any mono-, bi-, or tricyclic, saturated or unsaturated, aromatic (heteroaryl) or non-aromatic ring having the number of atoms designated, generally from 5 to about 14 ring atoms, where the ring atoms are carbon and at least one heteroatom (nitrogen, sulfur or oxygen). In a particular embodiment the group incorporates 1 to 4 heteroatoms. Typically, a 5-membered ring has 0 to 2 double bonds and 6- or 7-membered ring has 0 to 3 double bonds and the nitrogen or sulfur heteroatoms may optionally be oxidized (e.g. SO, $SO_2$), and any nitrogen heteroatom may optionally be quaternized. Particular non-aromatic heterocycles include morpholinyl (morpholino), pyrrolidinyl, oxiranyl, oxetanyl, tetrahydrofuranyl, 2,3-dihydrofuranyl, 2H-pyranyl, tetrahydropyranyl, thiiranyl, thietanyl, tetrahydrothietanyl, aziridinyl, azetidinyl, 1-methyl-2-pyrrolyl, piperazinyl and piperidinyl. A "heterocycloalkyl" group is a heterocycle group as defined above covalently bonded to an alkyl group as defined above.

Particular 5-membered heterocycles containing a sulfur or oxygen atom and one to three nitrogen atoms include thiazolyl, such as thiazol-2-yl and thiazol-2-yl N-oxide, thiadiazolyl such as 1,3,4-thiadiazol-5-yl and 1,2,4-thiadiazol-5-yl, oxazolyl such as oxazol-2-yl, and oxadiazolyl such as 1,3,4-oxadiazol-5-yl, and 1,2,4-oxadiazol-5-yl. Particular 5-membered ring heterocycles containing 2 to 4 nitrogen atoms include imidazolyl such as imidazol-2-yl; triazolyl such as 1,3,4-triazol-5-yl, 1,2,3-triazol-5-yl, and 1,2,4-triazol-5-yl, and tetrazolyl such as 1H-tetrazol-5-yl. Particular benzo-fused 5-membered heterocycles are benzoxazol-2-yl, benzthiazol-2-yl and benzimidazol-2-yl. Particular 6-membered heterocycles contain one to three nitrogen atoms and optionally a sulfur or oxygen atom, for example pyridyl, such as pyrid-2-yl, pyrid-3-yl, and pyrid-4-yl; pyrimidyl such as pyrimid-2-yl and pyrimid-4-yl; triazinyl such as 1,3,4-triazin-2-yl and 1,3,5-triazin-4-yl; pyridazinyl such as pyridazin-3-yl, and pyrazinyl. Substituents for optionally substituted heterocycles, and further examples of the 5- and 6-membered ring systems discussed above can be found in U.S. Pat. No. 4,278,793 to W. Druckheimer et al. Arylalkyl radical refers to alkyl radicals bearing an aryl substituent and have from about 6 to about 20 carbon atoms (and all combinations and subcombinations of ranges and specific numbers of carbon atoms therein), with from about 6 to about 12 carbon atoms being preferred. Arylalkyl groups can be optionally substituted. Non-limiting examples include, for example, benzyl, naphthylmethyl, diphenylmethyl, triphenylmethyl, phenylethyl, and diphenylethyl. A substituted arylalkyl group will contain one or more substituents on the aryl or alkyl group as defined for substituted alkyl groups.

Cycloalkylaryl radical or group refers to a cycloalkyl radical fused to an aryl group, including all combinations of independently substituted alkyl cycloalkylaryls, the cycloalkyl and aryl group having two atoms in common.

Cycloalkyl radical or group more specifically includes reference to a monovalent saturated carbocyclic alkyl radical consisting of one or more rings in their structures and having from about 3 to about 14 carbon atoms (and all combinations and subcombinations of ranges and specific numbers of carbon atoms therein), with from about 3 to about 7 carbon atoms being preferred. Multi-ring structures may be bridged or fused ring structures. The rings can optionally be substituted with one or more of the substituents for the alkyl groups. Examples of cycloalkyl groups include, but are not limited to, cyclopropyl, cyclobutyl, cyclopentyl, cyclohexyl, cyclooctyl, and adamantyl. A substituted cycloalkyl group will contain one or more substituents as defined for substituted alkyl groups.

Cycloalkylalkyl radical more specifically refers to alkyl radicals bearing an cycloalkyl substituent and having from about 4 to about 20 carbon atoms (and all combinations and subcombinations of ranges and specific numbers of carbon atoms therein), with from about 6 to about 12 carbon atoms being preferred and can include but are not limited to methylcyclopropyl, methylcyclohexyl, isopropylcyclohexyl, and butyl-cyclohexyl groups. Cycloalkylalkyl radical or group can be optionally substituted with one or more substituents for the alkyl groups including but not limited to hydroxy, cyano, alkyl, alkoxy, thioalkyl, halo, haloalkyl, hydroxyalkyl, nitro, amino, alkylamino and dialkylamino.

"Heteroaryl" alone and when used as a moiety in a complex group such as a heteroarylalkyl group, refers to any mono-, bi-, or tricyclic aromatic ring system having the number of atoms designated where at least one ring is a 5-, 6- or 7-membered ring containing from one to four heteroatoms selected from the group nitrogen, oxygen, and sulfur (Lang's Haltdbook of Chemistry, supra). Included in the definition are any bicyclic groups where any of the above heteroaryl rings are fused to a benzene ring. The following ring systems are examples of the heteroaryl (whether substituted or unsubstituted) groups denoted by the term "heteroaryl": thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo[1,5-b]pyridazinyl and purinyl, as well as benzo-fused derivatives, for example benzoxazolyl, benzofuryl, benzothiazolyl, benzothiadiazolyl, benzotriazolyl, benzoimidazolyl and indolyl. Particularly"heteroaryls" include; 1,3-thiazol-2-yl, 4-(carboxymethyl)-5-methyl-1,3-thiazol-2-yl, 4-(carboxymethyl)-

5-methyl-1,3-thiazol-2-yl sodium salt, 1,2,4-thiadiazol-5-yl, 3-methyl-1,2,4-thiadiazol-5-yl, 1,3,4-triazol-5-yl, 2-methyl-1, 3,4-triazol-5-yl, 2-hydroxy-1,3,4-triazol-5-yl, 2-carboxy-4-methyl-1,3,4-triazol-5-yl sodium salt, 2-carboxy-4-methyl-1,3,4-triazol-5-yl, 1,3-oxazol-2-yl, 1,3,4-oxadiazol-5-yl, 2-methyl-1,3,4-oxadiazol-5-yl, 2-(hydroxymethyl)-1,3,4-oxadiazol-5-yl, 1,2,4-oxadiazol-5-yl, 1,3,4-thiadiazol-5-yl, 2-thiol-1,3,4-thiadiazol-5-yl, 2-(methylthio)-1,3,4-thiadiazol-5-yl, 2-amino-1,3,4-thiadiazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 2-methyl-1H-tetrazol-5-yl, 1,2,3-triazol-5-yl, 1-methyl-1,2,3-triazol-5-yl, 2-methyl-1,2,3-triazol-5-yl, 4-methyl-1,2,3-triazol-5-yl, pyrid-2-yl N-oxide, 6-methoxy-2-(n-oxide)-pyridaz-3-yl, 6-hydroxypyridaz-3-yl, 1-methylpyrid-2-yl, 1-methylpyrid-4-yl, 2-hydroxypyrimid-4-yl, 1,4,5,6-tetrahydro-5,6-dioxo-4-methyl-as-triazin-3-yl, 1,4,5,6-tetrahydro-4-(formylmethyl)-5,6-dioxo-as-triazin-3-yl, 2,5-dihydro-5-oxo-6-hydroxy-astriazin-3-yl, 2,5-dihydro-5-oxo-6-hydroxy-as-triazin-3-yl sodium salt, 2,5-dihydro-5-oxo-6-hydroxy-2-methyl-astriazin-3-yl sodium salt, 2,5-dihydro-5-oxo-6-hydroxy-2-methyl-as-triazin-3-yl, 2,5-dihydro-5-oxo-6-methoxy-2-methyl-as-triazin-3-yl, 2,5-dihydro-5-oxo-as-triazin-3-yl, 2,5-dihydro-5-oxo-2-methyl-as-triazin-3-yl, 2,5-dihydro-5-oxo-2,6-dimethyl-as-triazin-3-yl, tetrazolo[1,5-b]pyridazin-6-yl and 8-aminotetrazolo[1,5-b]-pyridazin-6-yl. An alternative group of "heteroaryl" includes; 4-(carboxymethyl)-5-methyl-1,3-thiazol-2-yl, 4-(carboxymethyl)-5-methyl-1,3-thiazol-2-yl sodium salt, 1,3,4-triazol-5-yl, 2-methyl-1,3,4-triazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 1,2,3-triazol-5-yl, 1,4,5,6-tetrahydro-5,6-dioxo-4-methyl-as-triazin-3-yl, 1,4,5, 6-tetrahydro-4-(2-formylmethyl)-5,6-dioxo-as-triazin-3-yl, 2,5-dihydro-5-oxo-6-hydroxy-2-methyl-as-triazin-3-yl sodium salt, 2,5-dihydro-5-oxo-6-hydroxy-2-methyl-as-triazin-3-yl, tetrazolo[1,5-b]pyridazin-6-yl, and 8-aminotetrazolo[1,5-b]pyridazin-6-yl.

"Inhibitor" means a compound which reduces or prevents the binding of IAP proteins to caspase proteins or which reduces or prevents the inhibition of apoptosis by an IAP protein, or which binds to an IAP BIR domain in a manner similar to the amino terminal portion of Smac, thereby freeing Smac to inhibit the action of an IAP.

"Pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, salicyclic acid and the like.

The terms "mimetic," "peptide mimetic" and "peptidomimetic" are used interchangeably herein, and generally refer to a peptide, partial peptide or non-peptide molecule that mimics the tertiary binding structure or activity of a selected native peptide or protein functional domain (e.g., binding motif or active site). These peptide mimetics include recombinantly or chemically modified peptides, as well as non-peptide agents such as small molecule drug mimetics, as further described below.

As used herein, the terms "pharmaceutically acceptable", "physiologically tolerable" and grammatical variations thereof, as they refer to compositions, carriers, diluents and reagents, are used interchangeably and represent that the materials are capable of administration upon a mammal without the production of undesirable physiological effects such as nausea, dizziness, rash, or gastric upset.

"Providing" when used in conjunction with a therapeutic means to administer a therapeutic directly into or onto a target tissue or to administer a therapeutic to a patient whereby the therapeutic positively impacts the tissue to which it is targeted.

As used herein "subject" or "patient" refers to an animal or mammal including, but not limited to, human, dog, cat, horse, cow, pig, sheep, goat, chicken, monkey, rabbit, rat, mouse, etc.

As used herein, the term "therapeutic" means an agent utilized to treat, combat, ameliorate, prevent or improve an unwanted condition or disease of a patient. Embodiments of the present invention are directed to promote apoptosis, and thus cell death.

The terms "therapeutically effective amount" or "effective amount", as used herein, may be used interchangeably and refer to an amount of a therapeutic compound component of the present invention. For example, a therapeutically effective amount of a therapeutic compound is a predetermined amount calculated to achieve the desired effect, i.e., to effectively promote apoptosis, or to sensitize a cell to apoptosis preferably by eliminating an IAP inhibition of apoptosis, more preferably by inhibiting an IAP binding to a caspase.

"Mimetics" or "peptidomimetics" are synthetic compounds having a three-dimensional structure (i.e. a "core peptide motif") based upon the three-dimensional structure of a selected peptide. The peptide motif provides the mimetic compound with the desired biological activity, i.e., binding to IAP, wherein the binding activity of the mimetic compound is not substantially reduced, and is often the same as or greater than the binding affinity of the native peptide on which the mimetic is modeled. For example, in the mimetics of the present invention, we have found that $X_3$ and $X_4$ can be quite non-peptide like. Peptidomimetic compounds can have additional characteristics that enhance their therapeutic application, such as increased cell permeability, greater affinity and/or avidity and prolonged biological half-life.

Mimetic, specifically, peptidomimetic design strategies are readily available in the art and can be easily adapted for use in the present invention (see, e.g., Ripka & Rich, Curr. Op. Chem. Biol. 2, 441-452, 1998; Hruby et al., Curr. Op. Chem. Biol. 1, 114-119, 1997; Hruby & Balse, Curr. Med. Chem. 9, 945-970, 2000). One class of mimetic mimics a backbone that is partially or completely non-peptide, but mimics the peptide backbone atom-for-atom and comprises side groups that likewise mimic the functionality of the side groups of the native amino acid residues. Several types of chemical bonds, e.g. ester, thioester, thioamide, retroamide, reduced carbonyl, dimethylene and ketomethylene bonds, are known in the art to be generally useful substitutes for peptide bonds in the construction of protease-resistant peptidomimetics. Another class of peptidomimetics comprises a small non-peptide molecule that binds to another peptide or protein, but which is not necessarily a structural mimetic of the native peptide. Yet another class of peptidomimetics has arisen from combinatorial chemistry and the generation of massive chemical libraries. These generally comprise novel templates which, though structurally unrelated to the native peptide, possess necessary functional groups positioned on a nonpeptide scaffold to serve as "topographical" mimetics of the original peptide (Ripka & Rich, 1998, supra). Tetrapeptidomimetics of the invention are of the type disclosed and claimed in U.S. Pat. No. 6,992,063 to Shi et al.

It has been demonstrated in accordance with the present invention that the IAP-binding peptides or mimetics thereof are capable of potentiating apoptosis of cells.

Mimetics of the core IAP-binding portions are preferred. The mimetics described herein are suitably small, and since structural features in relation to the IAP binding groove are well-characterized, a wide variety of mimetic compounds may be synthesized. Added advantages of compounds of this size include improved solubility in aqueous solution and ease of delivery to selected targets in vivo.

In one embodiment, the IAP-binding peptides of the invention are modified to produce peptide mimetics by replacement of one or more naturally occurring side chains of the 20 genetically encoded amino acids, or D amino acids with other side chains, for instance with groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, to 7-membered heterocyclics. For example, proline analogs can be made in which the ring size of the proline residue is changed from 5 members to 4, 6, or 7 members. Cyclic groups can be saturated or unsaturated, and if unsaturated, can be aromatic or non-aromatic. Heterocyclic groups can contain one or more nitrogen, oxygen, and/or sulphur heteroatoms. Examples of such groups include the furazanyl, imidazolidinyl, imidazolyl, imidazolinyl, isothiazolyl, isoxazolyl, morpholinyl (e.g. morpholino), oxazolyl, piperazinyl (e.g. 1-piperazinyl), piperidyl (e.g. 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g. 1-pyrrolidinyl), pyrrolinyl, pyrrolyl, thiadiazolyl, thiazolyl, thienyl, thiomorpholinyl (e.g. thiomorpholino), and triazolyl. These heterocyclic groups can be substituted or unsubstituted. Where a group is substituted, the substituent can be alkyl, alkoxy, halogen, oxygen, or substituted or unsubstituted phenyl. Peptidomimetics may also have amino acid residues that have been chemically modified by phosphorylation, sulfonation, biotinylation, or the addition or removal of other moieties.

The present invention provides compounds which mimic the tertiary binding structure of Smac to IAPs or activity of the N-terminal portion of Smac. Stereoisomers of the mimetic compounds described herein are also encompassed in the present invention. The invention also provides methods of using these mimetics to modulate apoptosis and further for therapeutic purposes. The invention also provides intermediates and methods for using these intermediates for the preparation of compounds which modulate apoptosis by mimicking the tertiary binding structure of Smac to IAPs or activity of the N-terminal portion of Smac.

In accordance with the present invention, a compound of the present invention having the general formula (I) is provided:

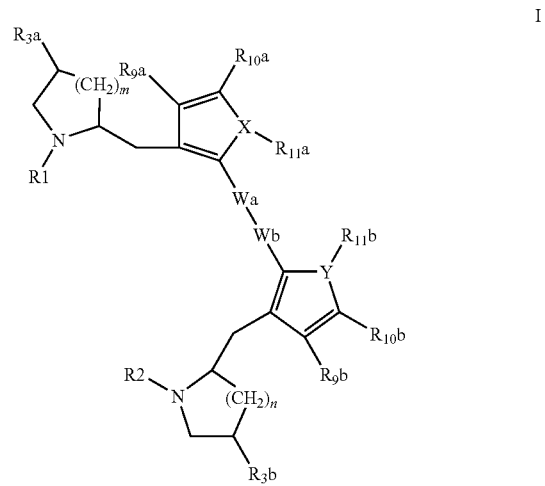

wherein R1 and R2 are independently H, tert-butoxycarbonyl, benzyloxycarbonyl, acetyl, trifluoroacetyl, alkyl, optionally-substituted alkyl, or

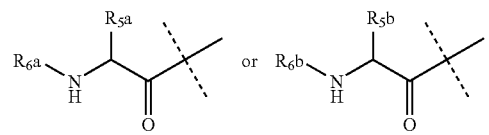

where R5a and R5b are independently H, alkyl, cycloalkyl, cycloalkylalkyl, heterocycloalkyl, aryl, arylalkyl, heteroaryl, heteroarylalkyl or each optionally-substituted with hydroxyl, mercapto, halogen, amino, carboxyl, alkyl, haloalkyl, alkoxy, or alkylthio; or R5a and R5b are independently optionally-substituted with hydroxyl, mercapto, halogen, amino, carboxyl, alkyl, haloalkyl, alkoxy, or alkylthio; or, optionally, R5a and R5b are connected by an alkylene, alkenylene, alkynylene bridge of 2 to 12 carbon atoms or optionally-substituted alkylene, alkenylene, alkynylene bridge of 2 to 12 carbon atoms where one or more carbon atoms are replaced with N, O, or S;

R6a and R6b are independently H, tert-butoxycarbonyl, benzyloxycarbonyl, acetyl, trifluoroacetyl, alkyl, lower alkyl, optionally-substituted alkyl, or

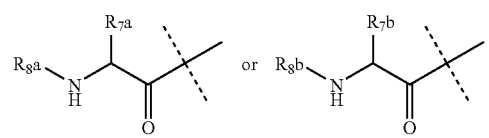

where R7a and R7b are independently H, alkyl, cycloalkyl, haloalkyl; or R8a and R7a and R8b and R7b can independently or together form a ring such as an aziridine or azetidine ring;

R8a and R8b are independently H, hydroxyl, alkyl, aryl, arylalkyl, cycloalkyl, cycloalkylalkyl, heteroaryl, or heteroarylalkyl wherein each alkyl, aryl, arylalkyl, cycloalkyl, cycloalkylalkyl, heteroaryl, and heteroarylalkyl is optionally-substituted with halogen, hydroxyl, mercapto, carboxyl, alkyl, alkoxy, amino, and nitro; or R8a and R7a and R8b and R7b can independently or together form a ring such as an aziridine or azetidine ring;

R3a and R3b are independently H, halogen, alkyl, aryl, arylalkyl, amino, arylamino, arylalkylamino, hydroxy, alkyloxy, aryloxy, arylalkylhydroxy, dialkylamino, amido, sulfonamido, or amidino;

m and n are independently 0, 1, 2, or 3;

X and Y are independently O, N, S, or C=C;

R9a, R9b, R10a, R10b are independently H, alkyl, optionally-substituted alkyl, aryl, heteroaryl, optionally-substituted aryl, heteroaryl, or R9a and R10a, independently or in parallel with R9b and R10b, can be linked by 4 to 8 optionally-substituted atoms such as C, N, O, or S, to form an aromatic or non-aromatic ring;

When Wa and Wb are covalently bound, Wa and Wb are a bond, alkylene, alkenylene, alkynylene, aryl, arylalkylene, arylalkylalkylene, heteroaryl, heteroarylalkylene, or an optionally-substituted alkylene, alkenylene, alkynylene chain of 2 to 12 carbon atoms where one or more carbon atoms can be replaced with N, O, or S; and R11a and R11b are independently absent, H, alkyl, optionally-substituted alkyl, hydroxyalkyl, alkoxyalkyl; or R11a and R11b together form an alkylene, alkenylene, alkynlyene, or alkyloxyalkylene chain of 2 to 12 carbon atoms where one or more carbon atoms are, optionally, replaced with N, O, or S;

When Wa and Wb are not covalently bound, Wa and Wb are independently be H, Cl, Br, F, alkyl, CN, CO2H; and R11a and R11b together form an alkylene, alkenylene, alkynylene, or alkyloxyalkylene chain of 2 to 12 carbon atoms or optionally substituted alkylene, alkenylene, alkynylene, or alkyloxyalkylene chain of 2 to 12 carbon atoms where one or more carbon atoms can be replaced with N, O, or S; or Wa can be H, Cl, Br, F, alkyl, CN, CO$_2$H and Wb and R11a together are a bond, alkylene, alkenylene, alkynylene, aryl, arylalkylene, arylalkylalkylene, heteroaryl, heteroarylalkylene, or an optionally-substituted alkylene, alkenylene, alkynylene chain of 2 to 12 carbon atoms where one or more carbon atoms can be replaced with N, O, or S; and R11b is absent or H, alkyl, optionally-substituted alkyl, hydroxyalkyl, alkoxyalkyl.

The compounds encompassed in the present invention include both Smac mimetics and intermediates therefor. The present invention includes stereoisomers of each disclosed compound. Generally, the compounds of the present invention include tertrapeptide mimetics of Smac, covelently attached dimers of tetrapeptide mimetics of Smac and covelently attached homodimers of tetrapeptide mimetics of Smac. Homodimers are those mimetics wherein the substantially identical tetrapeptide mimetics are covelently bound.

The experimental schemes below are related to the schemes used to produce the compounds first disclosed in PCT Publication No. WO 2004/007529, herein incorporated by reference in its entirety. Suitable peptides and peptidomimetics are also described in U.S. application Ser. No. 11/184,503 filed Jul. 15, 2005, entitled "IAP Binding Compounds" based upon U.S. Provisional Application No. 60/588,050 filed Jul. 15, 2004, the disclosures of which are herein incorporated by reference in their entireties.

The binding affinity of compounds embodies in the present invention to the XIAP was determined as described by Nikolovska-Coleska, Z. et. al. (Analytical Biochemistry (2004), vol. 332:261-273) using a variety of fluorogenic substrates and is reported as a $K_D$ value. Briefly, various concentrations of test peptides were mixed with 5 nM fluorescently labeled peptide (AbuRPF-K(5-Fam)-NH2) and 40 nM of XIAP-BIR3 for 15 min at RT in 100 μL of 0.1M Potassium Phosphate buffer, pH 7.5 containing 100 μg/ml bovine γ-globulin. Following incubation, the polarization values (mP) were measured on a Victor$^2$V using a 485 nm excitation filter and a 520 nm emission filter. IC$_{50}$ values were determined from the plot using nonlinear least-squares analysis using GraphPad Prism. The compounds described herein afford $K_D$ values in the ranges of: $K_D$<0.1 μM (A), $K_D$= 0.1-1 μM (B), $K_D$=1-10 μM (C), and $K_D$>10 μM (D).

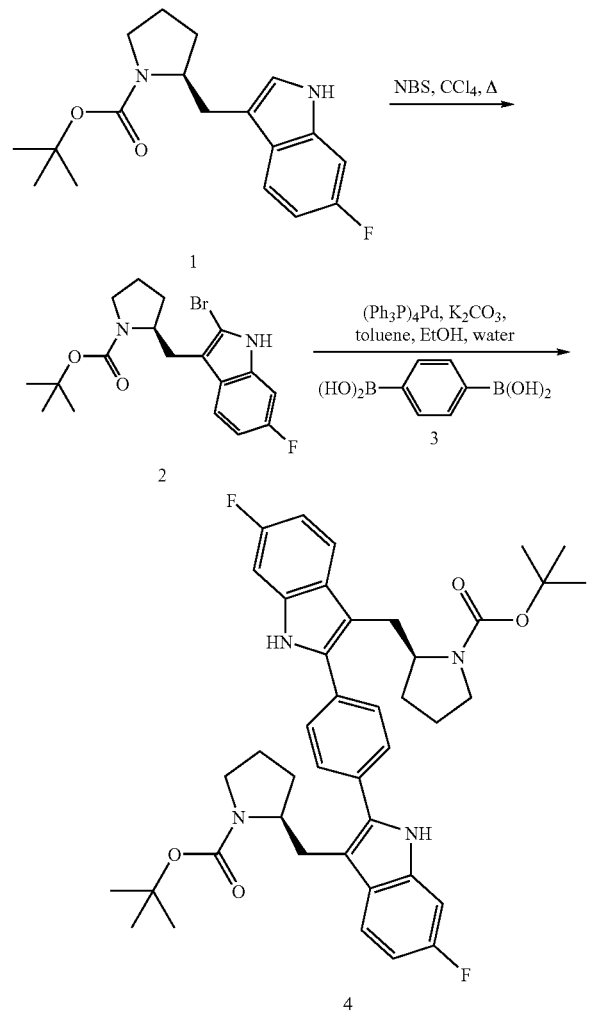

2-(2-Bromo-6-fluoro-1H-indol-3-ylmethyl)-pyrrolidine-1-carboxylic acid tert-butyl ester (2)

NBS (3.2 g, 17.9 mmol) was added to a solution containing 1 (5.4 g, 17.0 mmol) in CCl$_4$ (50 mL). The heterogeneous reaction mixture was heated to reflux (80-85° C.) for 2 h at which point TLC analysis revealed complete consumption of 1. [TLC analysis, 4:1 hexane/EtOAc, R$_f$(8)=0.4; R$_f$(2)=0.5]. The reaction mixture was cooled to ambient temperature then poured onto a column of silica gel. The product was eluted with 10-15% EtOAc/hexane to afford 4.4 g (65%) of 2 as a white solid. $^1$H NMR (DMSO, 300 MHz) δ 11.74 (s, 1H), 7.56

(m, 1H), 7.02 (d, J=9.3 Hz, 1H), 6.88 (m, 1H), 3.99 (m, 1H), 3.22 (m, 2H), 2.97 (m, 1H), 2.58 (dd, J=13.5, 9.3 Hz, 1H), 1.9-1.5 (4H), 1.40 (s, 9H) ppm.

1,4-Bis-[2-(6-Fluoro-1H-indol-3-ylmethyl)-pyrrolidine-1-carboxylic acid tert-butyl ester]benzene (4)

A solution containing 2 (3.3 g, 8.3 mmol) in toluene (25 mL), EtOH (25 mL), and water (1 mL) was degassed under high vacuum. $K_2CO_3$ (4.5 g, 32.5 mmol), 3 (0.97 g, 5.8 mmol), and $(Ph_3P)_4Pd$ (0.29 g, 0.25 mmol) were added and the resulting mixture was stirred at 100° C. for 5 h. [TLC analysis, 4:1 hexane/EtOAc, $R_f(2)$=0.5; $R_f(4)$=0.3]. The reaction mixture was filtered through a short pad of silica gel and washed with 5% EtOAc/hexane. The filtrate was concentrated and the crude product was purified by flash silica gel chromatography (20% EtOAc/hexane) to afford 3.0 g (98%) of 4 as an off-white, highly-fluorescent solid. $^1$H NMR ($CDCl_3$, 300 MHz) δ8.6-8.4 (m, 2H), 7.65 (m, 2H), 7.57 (br s, 4H), 7.05 (m, 2H), 7.90 (m, 2H), 4.22 (br s, 2H), 3.4-3.1 (m, 6H), 2.90 (m, 2H), 1.8-1.3 (m, 26H) ppm.

1,4-Bis-{2-[1-(2-Acetoxy-ethyl)-6-fluoro-1H-indol-3-ylmethyl]-pyrrolidine-1-carboxylic acid tert-butyl ester}benzene (6)

To a suspension of 60% NaH (0.67 g, 17.0 mmol) in anhydrous DMF (10 mL) was added a solution of 4 (3.0 g, 4.2 mmol) in DMF (10 mL) at 0° C. The reaction mixture was allowed to stir at ambient temperature for 1 h then re-cooled to 0° C. A solution containing 5 (2.8 g, 16.8 mmol) in DMF (5 mL) was added to the reaction mixture and the ice bath was removed following addition. After 2 h at ambient temperature, LC/MS and TLC analyses revealed complete consumption of 4. [TLC analysis, 2:1 hexane/EtOAc, $R_f(4)$=0.4; $R_f(6)$= 0.8]. The reaction mixture was cooled to 0° C. and saturated aqueous $NH_4Cl$ was added. The product was extracted with diethyl ether. The ether extracts were washed with water, brine, dried over anhydrous $Na_2SO_4$, filtered, and concentrated. The crude product was purified by NP—HPLC (silica gel, 10-100% EtOAc/hexane over 30 min) to afford 1.4 g of 6 as an off-white solid. $^1$H NMR ($CDCl_3$, 300 MHz) δ7.68 (m, 2H), 7.54 (s, 4H), 7.12 (m, 2H), 6.94 (m, 2H), 4.25 (m, 4H), 4.14 (m, 6H), 3.4-3.1 (6H), 2.60 (dd, J=9.6, 13.8 Hz, 2H), 1.90 (s, 6H), 1.83 (m, 2H), 1.7-1.3 (m, 24H) ppm.

Scheme II

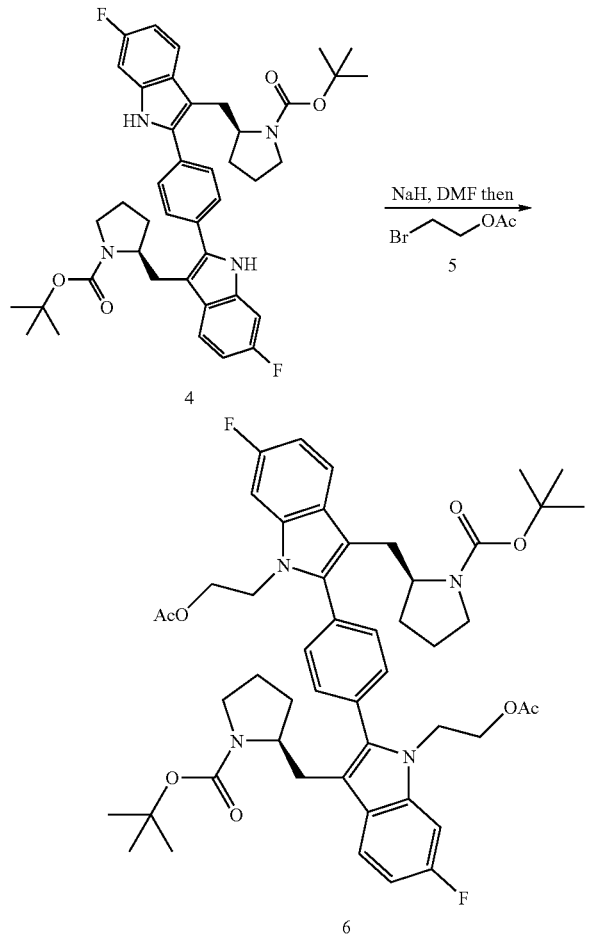

Scheme III

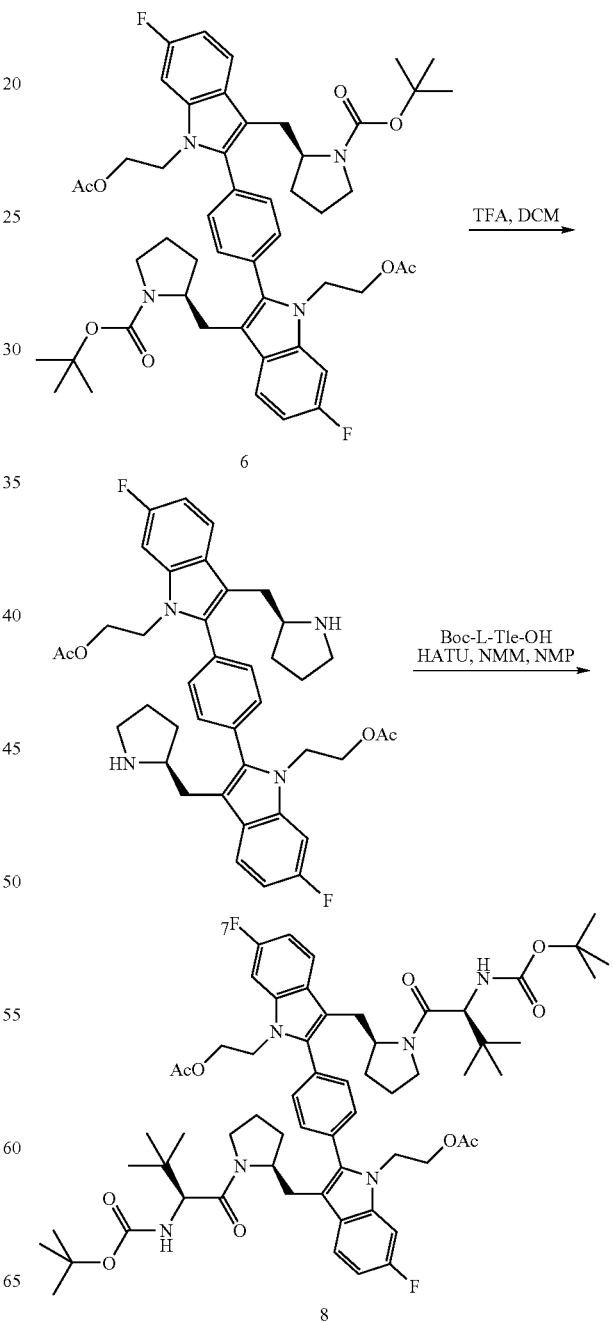

Acetic acid 2-(2-{4-[1-(2-acetoxy-ethyl)-6-fluoro-3-pyrrolidin-2-ylmethyl-1H-indol-2-yl]-phenyl}-6-fluoro-3-pyrrolidin-2-ylmethyl-indol-1-yl)-ethyl ester (7)

A solution containing 6 (1.4 g, 1.58 mmol) in DCM (20 mL) was cooled to 0° C. TFA (5 mL) was added via pipette and the reaction was allowed to warm to ambient temperature and monitored until TLC analysis revealed complete consumption of 6 (~2 h). TLC analysis, 10% MeOH/DCM, Rf(6)= 0.7; Rf(7)=0.2. The solvent was removed on a rotary evaporator and the residue was dissolved in EtOAc. The EtOAc solution was washed twice with saturated aqueous NaHCO3 and once with brine. The combined aqueous washes were back-extracted with EtOAc and the organic extracts were dried over anhydrous Na2SO4, filtered, and concentrated to afford 1.2 g (quant.) of 7 as a yellow solid which was used without further purification. $^1$H NMR (CDCl$_3$, 300 MHz) δ8.05 (dd, J=8.4, 5.4 Hz, 2H), 7.56 (s, 4H), 7.13 (dd, J=9.9, 2.4 Hz, 2H), 6.99 (m, 2H), 4.60 (d, J=9.9 Hz, 2H), 4.51 (m, 2H), 4.26 (m, 4H), 4.15 (m, 4H), 3.63 (m, 2H), 3.54 (m, 2H), 3.5-3.3 (m, 4H), 2.41 (m, 2H), 1.89 (s, 6H), 1.8-1.5 (m, 6H), 1.43 (s, 18H), 1.09 (s, 18H) ppm.

1,4-Bis-{Acetic acid 2-{3-[1-(2-tert-butoxycarbonylamino-3,3-dimethyl-butyryl)-pyrrolidin-2-ylmethyl]-6-fluoro-indol-1-yl}-ethyl ester}benzene (8)

A solution containing Boc-L-tert-Leu-OH (0.82 g, 3.54 mmol) and HATU (1.41 g, 3.70 mmol) in anhydrous NMP (15 mL) was cooled to 0° C. After 15 min, N-methylmorpholine (0.46 g, 0.5 mL, 4.54 mmol) was added via syringe. After 15 min, a solution containing 7 (1.10 g, 1.61 mmol) in DCM (10 mL) was added and the reaction mixture was allowed to warm to ambient temperature over 16 h at which point TLC analysis revealed complete consumption of 7 [TLC analysis, 2:1 hexane/EtOAc, R$_f$(7)=0.01; R$_f$(8)=0.8]. The reaction mixture was diluted with diethyl ether and washed once with dilute aqueous HCl, five times with water to remove excess NMP, once with saturated aqueous NaHCO$_3$ and brine, dried over anhydrous Na$_2$SO$_4$, filtered, and concentrated. The crude product was purified by NP—HPLC (silica gel, 10-100% EtOAc/hexane over 30 min) to afford 1.3 g (73%) of 8 as an off-white solid. $^1$H NMR (CDCl$_3$, 300 MHz) δ8.05 (dd, J=5.4, 8.4 Hz, 2H), 7.56 (s, 4H), 7.11 (dd, J=2.4, 9.9 Hz, 2H), 6.98 (m, 2H), 5.43 (d, J=9.9 Hz, 2H), 4.51 (m, 2H), 4.26 (m, 6H), 4.17 (m, 6H), 3.2-3.7 (m, 8H), 2.41 (dd, J=12, 13 Hz, 2H), 1.88 (s, 6H), 1.7-1.5 (m, 4H), 1.43 (s, 18H), 1.04 (s, 18H) ppm.

Scheme IV

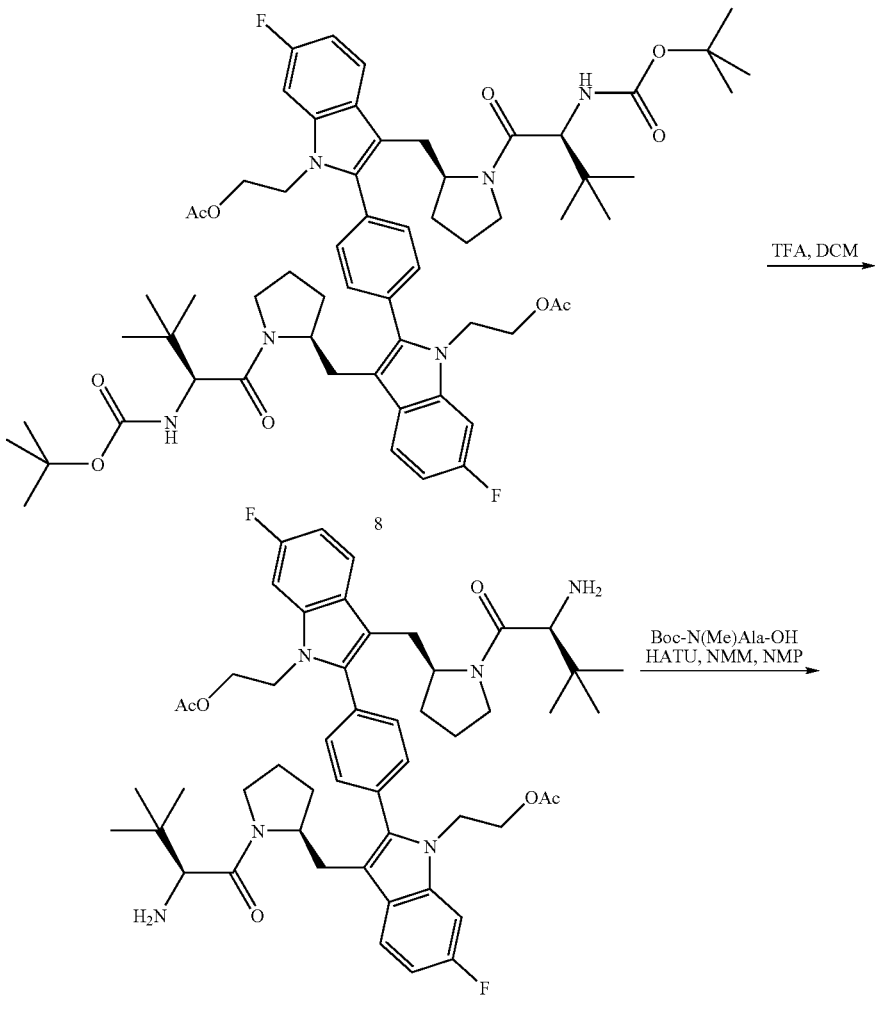

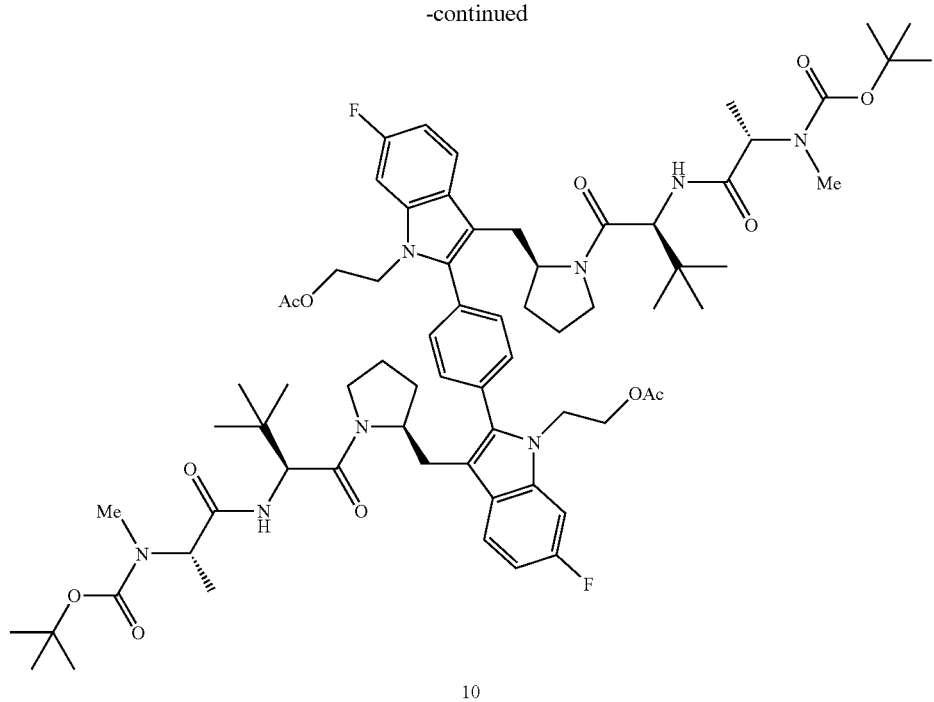

10

Acetic acid 2-{2-(4-{1-(2-acetoxy-ethyl)-3-[1-(2-amino-3,3-dimethyl-butyryl)-pyrrolidin-2-ylmethyl]-6-fluoro-1H-indol-2-yl}-phenyl)-3-[1-(2-amino-3,3-dimethyl-butyryl)-pyrrolidin-2-ylmethyl]-6-fluoro-indol-1-yl}-ethyl ester (9)

A solution containing 8 (1.3 g, 1.17 mmol) in DCM (5 mL) was cooled to 0° C. 20% TFA in DCM (25 mL) was added via pipette and the reaction was allowed to warm to ambient temperature and monitored until TLC analysis revealed complete consumption of 8 (~2 h). TLC analysis, 10% MeOH/DCM, $R_f$(8)=0.7; $R_f$(9)=0.3. The solvent was removed on a rotary evaporator and the residue was purified by RP-HPLC (Method: Solvent A: water w/0.1% v/v HOAc, Solvent B: ACN w/0.1% v/v HOAc. Dynamax Microsorb C18 60 Å 8μ, 41.4 mm×25 cm; Flow: 40 mL/min; Detector: 254 nm). The product-containing fractions were pooled and neutralized with saturated aqueous NaHCO$_3$. The product was extracted with EtOAc and the organic extract was washed with brine, dried over anhydrous Na$_2$SO$_4$, filtered, and concentrated to afford 0.80 g (75%) of 9 as an off-white solid. $^1$H NMR (CDCl$_3$, 300 MHz) δ 8.09 (dd, J=5.1, 8.7 Hz, 2H), 7.51 (s, 4H), 7.13 (m, 2H), 7.0 (m, 2H), 4.41 (m, 2H), 4.25 (m, 4H), 4.16 (m, 4H), 3.6-3.0 (m, 6H), 2.86 (m, 2H), 2.39 (m, 2H), 1.91 (s, 6H), 1.8-1.4 (m, 12H), 1.04 (s, 18H) ppm.

1,4-Bis-{Acetic acid 2-[3-(1-{2-[2-(tert-butoxycarbonyl-methyl-amino)-propionylamino]-3,3-dimethyl-butyryl}-pyrrolidin-2-ylmethyl)-6-fluoro-indol-1-yl]-ethyl ester}benzene (10)

A solution containing Boc-L-N(Me)Ala-OH (0.27 g, 1.32 mmol) and HATU (0.54 g, 1.43 mmol) in anhydrous NMP (15 mL) was cooled to 0° C. After 15 min, N-methylmorpholine (0.17 g, 0.2 mL, 1.68 mmol) was added via syringe. After 15 min, a solution containing 9 (0.50 g, 0.55 mmol) in DCM (10 mL) was added and the reaction mixture was allowed to warm to ambient temperature over 16 h at which point TLC analysis revealed complete consumption of 9 [TLC analysis, 3:2 hexane/EtOAc, $R_f$(9)=0.01; $R_f$(10)=0.5]. The reaction mixture was diluted with diethyl ether and washed once with dilute aqueous HCl, five times with water to remove excess NMP, once with saturated aqueous NaHCO$_3$ and brine, dried over anhydrous Na$_2$SO$_4$, filtered, and concentrated. The crude product was purified by NP—HPLC (silica gel, 10-100% EtOAc/hexane over 30 min) to afford 0.64 g (91%) of 10 as an off-white solid. $^1$H NMR (CDCl$_3$, 300 MHz) δ 8.05 (m, 2H), 7.58 (br s, 4H), 7.13 (m, 2H), 6.97 (m, 2H), 4.75 (m, 2H), 4.60 (d, J=9.3 Hz, 2H), 4.50 (m, 2H), 4.25 (m, 4H), 4.16 (m, 4H), 3.70 (m, 2H), 3.57 (m, 4H), 3.5-3.2 (m, 4H), 2.85 (br s, 6H), 2.42 (m, 2H), 1.88 (s, 6H), 1.8-1.4 (m, 8H), 1.52 (s, 18H), 1.33 (m, 6H), 1.04 (br s, 18H) ppm.

Scheme V
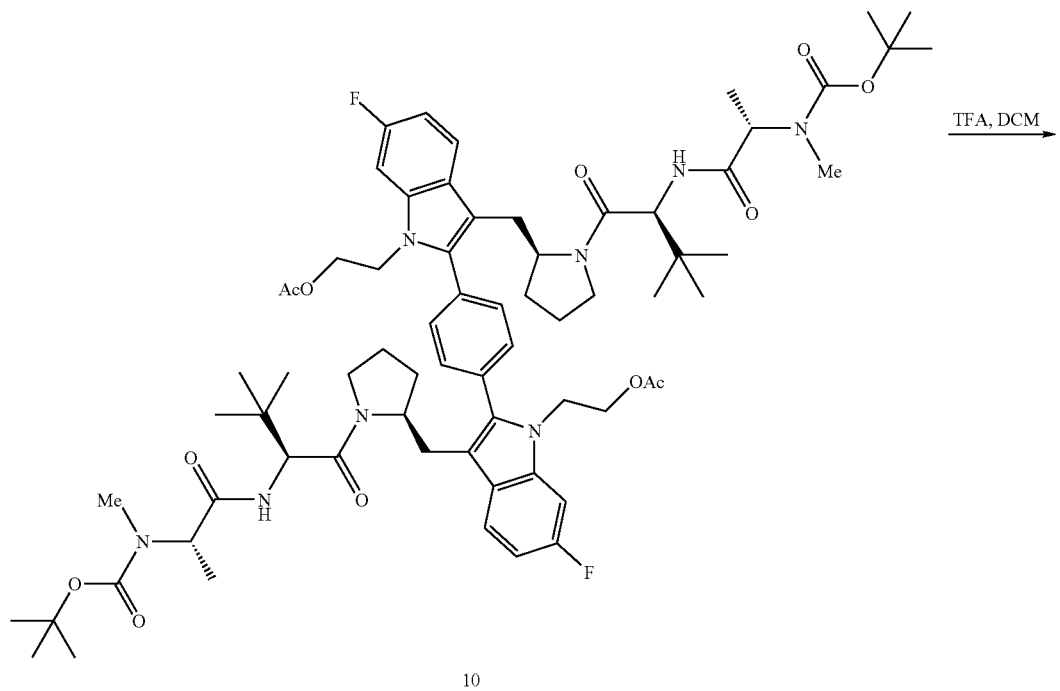
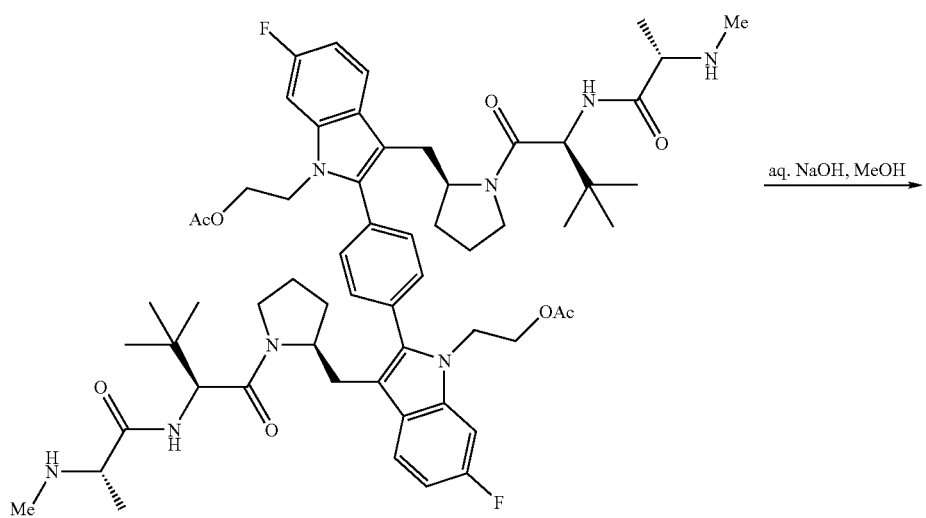

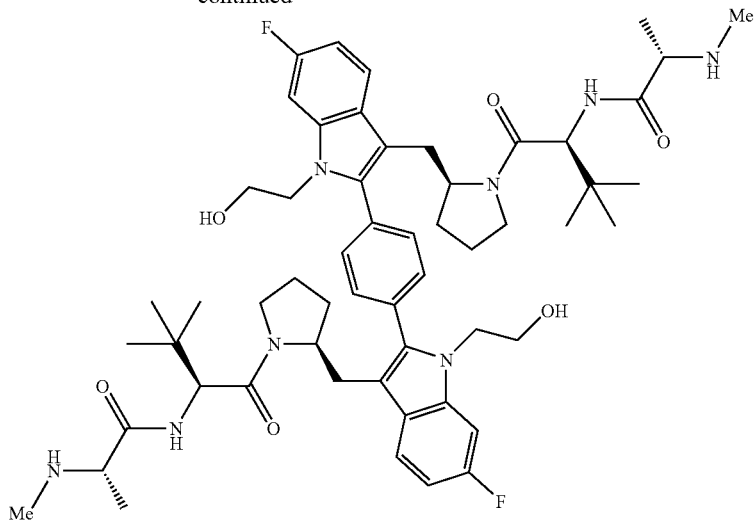

12

1,4-Bis-{Acetic acid 2-(3-{1-[3,3-dimethyl-2-(2-methylamino-propionylamino)-butyryl]-pyrrolidin-2-ylmethyl}-6-fluoro-indol-1-yl)-ethyl ester}benzene (11)

A solution containing 10 (0.64 g, 0.5 mmol) in DCM (20 mL) was cooled to 0° C. TFA (5 mL) was added via pipette and the reaction was allowed to warm to ambient temperature and monitored until TLC analysis revealed complete consumption of 10 (~2 h). The solvent was removed on a rotary evaporator and the residue was purified by RP-HPLC (Method: Solvent A: water w/0.1% v/v HOAc, Solvent B: ACN w/0.1% v/v HOAc. Dynamax Microsorb C18 60 Å 8 μ, 41.4 mm×25 cm; Flow: 40 mL/min; Detector: 254 nm). The product-containing fractions were pooled and neutralized with saturated aqueous NaHCO$_3$. The product was extracted with EtOAc and the organic extract was washed with brine, dried over anhydrous Na$_2$SO$_4$, filtered, and concentrated to afford 0.50 g (93%) of 11 as an off-white solid. $^1$H NMR (CDCl$_3$, 300 MHz) δ8.04 (m, 2H), 7.83 (d, J=9.3 Hz, 2H), 7.55 (m, 4H), 7.12 (m, 2H), 6.99 (m, 2H), 4.60 (d, J=9.3 Hz, 2H), 4.57 (m, 2H), 4.24 (m, 4H), 3.73 (m, 2H), 3.55 (m, 2H), 3.41 (m, 2H), 3.30 (m, 2H), 3.08 (m, 2H), 2.40 (s, 6H), 2.38 (m, 2H), 1.87 (s, 6H), 1.8-1.3 (m, 16H), 1.04 (br s, 18H) ppm.

1,4-Bis-{N-(1-{2-[6-Fluoro-1-(2-hydroxy-ethyl)-1H-indol-3-ylmethyl]-pyrrolidine-1-carbonyl}-2,2-dimethyl-propyl)-2-methylamino-propionamide}benzene (12)

Aqueous NaOH (1 M, 5 mL, excess) was added at 0° C. to a solution containing 11 (0.48 g, 0.44 mmol) in MeOH (5 mL). Following the addition, the ice bath was removed and the reaction mixture was stirred at ambient temperature for 1 h. The reaction mixture was diluted with water/EtOAc and the layers were separated. The organic phase was washed with brine, dried over anhydrous Na$_2$SO$_4$, filtered, and concentrated. The residue was purified by RP-HPLC (Method: Solvent A: water w/0.1% v/v HOAc, Solvent B: ACN w/0.1% v/v HOAc. Dynamax Microsorb C18 60 Å 8μ, 41.4 mm×25 cm; Flow: 40 mL/min; Detector: 254 nm). The product-containing fractions were pooled, frozen, and lyophilized to afford 0.19 g of 12 as a flocculent, white solid. $^1$H NMR (CDCl$_3$, 300 MHz) δ ppm. $^{13}$C NMR (CDCl$_3$, 75 MHz) δ7.8-7.4 (m, 8H), 7.11 (m, 2H), 6.95 (m, 2H), 4.57 (d, J=9.3 Hz, 2H), 4.4-4.0 (m, 6H), 3.8-3.4 (m, 8H), 3.2-3.0 (m, 3H), 2.6-2.4 (m, 14H), 2.38 (m, 6H), 2.2-1.5 (m, 12H), 1.29 (d, J=6.9 Hz, 6H), 1.00 (s, 18H) ppm.

EXAMPLES

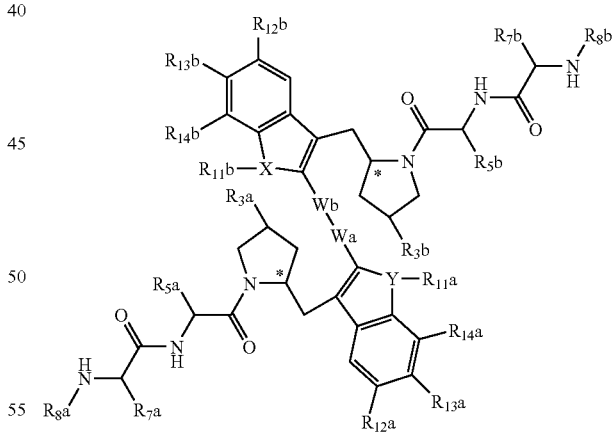

Example 1 where R7a and R7b are independently H, alkyl, cycloalkyl, haloalkyl; or R8a and R7a and R8b and R7b can independently or together form a ring such as an aziridine or azetidine ring;

R8a and R8b are independently H, hydroxyl, alkyl, aryl, arylalkyl, cycloalkyl, cycloalkylalkyl, heteroaryl, or heteroarylalkyl wherein each alkyl, aryl, arylalkyl, cycloalkyl, cycloalkylalkyl, heteroaryl, and heteroarylalkyl is optionally-substituted with halogen, hydroxyl, mercapto, carboxyl, alkyl, alkoxy, amino, and nitro; or R8a and R7a and R8b and R7b can independently or together form a ring such as an aziridine or azetidine ring;

where R5a and R5b are independently H, alkyl, cycloalkyl, cycloalkylalkyl, heterocycloalkyl, aryl, arylalkyl, heteroaryl, heteroarylalkyl; or each optionally-substituted with hydroxyl, mercapto, halogen, amino, carboxyl, alkyl, haloalkyl, alkoxy, or alkylthio; or, in some instances, the R5a and R5b residues are connected by an alkylene, alkenylene, alkynylene bridge of 2 to 12 carbon atoms or optionally-substituted alkylene, alkenylene, alkynylene bridge of 2 to 12 carbon atoms where one or more carbon atoms can be replaced with N, O, or S;

R12a, R12b, R13a, R13b, R14a, and R14b are independently H, Cl, Br, F, alkyl, cycloalkyl, hydroxy, alkoxy, amino, alkylamino, cyano, or $CO_2H$;

R3a and R3b are independently H, halogen, alkyl, aryl, arylalkyl, amino, arylamino, arylalkylamino, hydroxy, alkyloxy, aryloxy, arylalkylhydroxy, dialkylamino, amido, sulfonamido, or amidino;

X and Y are independently O, N, S, or C=C;

R11a and R11b are absent or independently H, alkyl, optionally-substituted alkyl, hydroxyalkyl, alkoxyalkyl; or R11a and R11b together form an alkylene, alkenylene, alkynlyene, or alkyloxyalkylene chain of 2 to 12 carbon atoms where one or more carbon atoms can be replaced with N, O, or S;

Wa and Wb together are a bond, alkylene, alkenylene, alkynylene, aryl, heteroaryl, or an optionally-substituted alkylene, alkenylene, alkynylene chain of 2 to 12 carbon atoms where one or more carbon atoms can be replaced with N, O, or S.

| Entry | R8a | R7a | R5a | Stereochem at Position (*) | X | Y | R11 | Wa-Wb |
|---|---|---|---|---|---|---|---|---|
| 1 | H | S-Me | S-iPr | S | O | O | na | 1,4-phenyl |
| 2 | H | S-Me | S-iPr | S | O | O | na | trans-(CH=CH) |
| 3 | H | S-Me | S-iPr | S | O | O | na | $CH_2CH_2$ |
| 4 | H | S-Me | S-iPr | S | O | O | na | 1,4-phenyl |
| 6 | H | S-Me | S-iPr | S | N | N | NH | 1,4-phenyl |
| 7 | H | S-Me | S-tBu | S | O | O | na | 1,4-phenyl |
| 8 | Me | S-Me | S-tBu | S | O | O | na | 1,4-phenyl |
| 9 | H | S-Et | S-tBu | S | O | O | na | 1,4-phenyl |
| 10 | Me | S-Me | S-iPr | S | O | O | na | 1,4-phenyl |
| 11 | H | S-Et | S-iPr | S | O | O | na | 1,4-phenyl |
| 12 | H | S-Me | S-cHex | S | O | O | na | 1,4-phenyl |
| 13 | Me | S-Me | S-cHex | S | O | O | na | 1,4-phenyl |
| 14 | H | S-Et | S-cHex | S | O | O | na | 1,4-phenyl |
| 15 | Me | S-Me | S-(2R-EtOH) | S | O | O | na | 1,4-phenyl |
| 16 | Me | S-Me | S-iPr | S | N | N | H | 1,4-phenyl |
| 17 | H | S-Me | S-iPr | S | N | N | H | 2,5-thiophenyl |
| 18 | Me | S-Me | S-cHex | S | N | N | H | 2,5-thiophenyl |
| 19 | H | S-Me | S-cHex | S | N | N | H | 1,4-phenyl |
| 20 | Me | S-Me | S-cHex | S | N | N | H | 1,4-phenyl |
| 21 | Me | S-Me | S-iPr | R | N | N | H | 1,4-phenyl |
| 22 | Me | S-Me | S-tBu | R | N | N | H | 1,4-phenyl |
| 23 | Me | S-Me | S-iPr | S | N | N | H | 1,4-phenyl |
| 24 | Me | S-Me | S-tBu | R | N | N | H | 1,4-phenyl |
| 25 | Me | S-Me | S-(2R-EtOBn) | S | N | N | H | 1,4-phenyl |
| 26 | Me | S-Me | S-(2R-EtOH) | S | N | N | H | 1,4-phenyl |
| 27 | Me | S-Me | S-(2R-EtOH) | S | N | N | H | 1,4-phenyl |
| 28 | Me | S-Me | S-(2R-EtOH) | R | N | N | H | 1,4-phenyl |
| 29 | Me | S-Me | S-iPr | R | N | N | H | 1,4-phenyl |
| 30 | Me | S-Me | S-tBu | R | N | N | H | 1,4-phenyl |
| 31 | Me | S-Me | S-(2R-EtOH) | S | N | N | H | 1,4-phenyl |
| 32 | Me | S-Me | S-(2R-EtOH) | S | N | N | H | 1,4-phenyl |
| 33 | Me | S-Me | S-(2R-EtOBn) | S | N | N | H | 1,4-phenyl |
| 34 | Me | S-Me | S-tBu | R | N | N | H | 1,4-phenyl |
| 35 | Me | S-Me | S-iPr | S | N | N | H | 1,4-phenyl |
| 36 | Me | S-Me | S-tBu | R | N | N | H | 1,4-phenyl |
| 37 | Me | S-Me | S-iPr | R | N | N | H | 1,4-phenyl |
| 38 | Me | S-Me | S-cHex | S | N | N | H | 1,4-phenyl |
| 39 | H | S-Me | S-cHex | S | N | N | H | 1,4-phenyl |
| 40 | Me | S-Me | S-iPr | R | N | N | H | 1,4-phenyl |
| 41 | Me | S-Me | S-tBu | R | N | N | H | 1,4-phenyl |
| 42 | H | S-Me | S-(2R-EtOH) | S | N | N | $CH_2CH_2OH$ | 1,4-phenyl |
| 43 | H | S-Me | S-(2R-EtOH) | S | N | N | $CH_2CH_2OH$ | 1,4-phenyl |

-continued

| | | | | | | | | |
|---|---|---|---|---|---|---|---|---|
| 44 | Me | S-Me | S-(2R-EtOH) | S | N | N | CH$_2$CH$_2$OH | 1,4-phenyl |
| 45 | H | S-Me | S-(2R-EtOH) | S | N | N | CH$_2$CH$_2$OAc | 1,4-phenyl |
| 46 | Me | S-Me | S-iPr | S | N | N | CH$_2$CH$_2$OH | 1,4-phenyl |
| 47 | Me | S-Me | S-iPr | S | N | N | CH$_2$CH$_2$OAc | 1,4-phenyl |
| 487 | Me | S-Me | S-tBu | S | N | N | CH$_2$CH$_2$OH | 1,4-phenyl |
| 49 | Me | S-Me | S-tBu | S | N | N | CH$_2$CH$_2$OAc | 1,4-phenyl |
| 50 | Me | S-Me | S-(2R-EtOH) | S | N | N | CH$_2$CH$_2$OMe | 1,4-phenyl |
| 51 | Me | S-Me | S-tBu | S | N | N | CH$_2$CH$_2$OMe | 1,4-phenyl |
| 52 | Me | S-Me | S-iPr | S | N | N | CH$_2$CH$_2$OMe | 1,4-phenyl |
| 53 | H | S-Me | S-iPr | S | N | N | CH$_2$CH$_2$OMe | 1,4-phenyl |
| 54 | Me | S-Me | S-tBu | S | N | N | CH$_2$CH$_2$OH | 1,4-phenyl |
| 55 | Me | S-Me | S-iPr | S | N | N | CH$_2$CH$_2$OH | 1,4-phenyl |
| 56 | Me | S-Me | S-(2R-EtOH) | S | N | N | CH$_2$CH$_2$OH | 1,4-phenyl |
| 57 | Me | S-Me | S-iPr | S | N | N | Me | 1,4-phenyl |
| 58 | Me | S-Me | S-(2R-EtOH) | S | N | N | Me | 1,4-phenyl |
| 59 | Me | S-Me | S-tBu | S | N | N | Me | 1,4-phenyl |
| 60 | Me | R-Me | R-tBu | R | N | N | CH$_2$CH$_2$OH | 1,4-phenyl |
| 61 | H | R-Me | R-iPr | R | O | O | na | 1,4-phenyl |

| Entry | R3a | R3b | R5b | R7b | R8b | R12 | R13 | R14 | K$_D$ Range, |
|---|---|---|---|---|---|---|---|---|---|
| 1 | H | H | S-iPr | S-Me | H | H | H | H | A |
| 2 | H | H | S-iPr | S-Me | H | H | H | H | A |
| 3 | H | H | S-iPr | S-Me | H | H | H | H | A |
| 4 | H | H | S-iPr | H | H | H | H | H | A |
| 6 | H | H | S-iPr | S-Me | H | H | H | H | A |
| 7 | H | H | S-tBu | S-Me | H | H | H | H | A |
| 8 | H | H | S-tBu | S-Me | Me | H | H | H | A |
| 9 | H | H | S-tBu | S-Et | H | H | H | H | B |
| 10 | H | H | S-iPr | S-Me | Me | H | H | H | A |
| 11 | H | H | S-iPr | S-Et | H | H | H | H | A |
| 12 | H | H | S-cHex | S-Me | H | H | H | H | A |
| 13 | H | H | S-cHex | S-Me | Me | H | H | H | A |
| 14 | H | H | S-cHex | S-Et | H | H | H | H | B |
| 15 | H | H | S-(2R-EtOH) | S-Me | Me | H | H | H | A |
| 16 | H | H | S-iPr | S-Me | Me | H | F | H | A |
| 17 | H | H | S-iPr | S-Me | H | H | F | H | A |
| 18 | H | H | S-cHex | S-Me | Me | H | F | H | A |
| 19 | H | H | S-cHex | S-Me | H | H | F | H | A |
| 20 | H | H | S-cHex | S-Me | Me | H | F | H | A |
| 21 | R—OH | R—OH | S-iPr | S-Me | Me | H | H | H | B |
| 22 | R—OH | R—OH | S-tBu | S-Me | Me | H | H | H | B |
| 23 | H | H | S-iPr | S-Me | Me | F | H | H | A |
| 24 | S—OH | S—OH | S-tBu | S-Me | Me | H | H | H | A |
| 25 | H | H | S-(2R-EtOBn) | S-Me | Me | H | F | H | A |
| 26 | H | H | S-(2R-EtOBn) | S-Me | Me | H | F | H | A |
| 27 | H | H | S-(2R-EtOH) | S-Me | Me | H | F | H | A |
| 28 | S—OH | S—OH | S-(2R-EtOH) | S-Me | Me | H | F | H | A |
| 29 | S—OH | S—OH | S-iPr | S-Me | Me | H | F | H | A |
| 30 | S—OH | S—OH | S-tBu | S-Me | Me | H | F | H | A |
| 31 | H | H | S-(2R-EtOH) | S-Me | Me | H | F | H | A |
| 32 | H | H | S-(2R-EtOBn) | S-Me | Me | H | F | H | A |
| 33 | H | H | S-(2R-EtOBn) | S-Me | Me | H | F | H | A |
| 34 | S—OH | S—OH | S-tBu | S-Me | Me | H | H | H | A |
| 35 | H | H | S-iPr | S-Me | Me | F | H | H | A |
| 36 | R—OH | R—OH | S-tBu | S-Me | Me | H | H | H | B |

| | | | | | | | | | |
|---|---|---|---|---|---|---|---|---|---|
| 37 | R—OH | R—OH | S-iPr | S-Me | Me | H | H | H | B |
| 38 | H | H | S-cHex | S-Me | Me | H | F | H | A |
| 39 | H | H | S-cHex | S-Me | H | H | F | H | A |
| 40 | S—OH | S—OH | S-iPr | S-Me | Me | F | H | H | B |
| 41 | S—OH | S—OH | S-tBu | S-Me | Me | F | H | H | A |
| 42 | H | H | S-(2R-EtOBn) | S-Me | Me | H | F | H | A |
| 43 | H | H | S-(2R-EtOH) | S-Me | Me | H | F | H | A |
| 44 | H | H | S-(2R-EtOH) | S-Me | Me | H | F | H | A |
| 45 | H | H | S-(2R-EtOH) | S-Me | Me | H | F | H | A |
| 46 | H | H | S-iPr | S-Me | Me | H | F | H | A |
| 47 | H | H | S-iPr | S-Me | Me | H | F | H | A |
| 487 | H | H | S-tBu | S-Me | Me | H | F | H | A |
| 49 | H | H | S-tBu | S-Me | Me | H | F | H | A |
| 50 | H | H | S-(2R-EtOH) | S-Me | Me | H | F | H | A |
| 51 | H | H | S-tBu | S-Me | Me | H | F | H | A |
| 52 | H | H | S-iPr | S-Me | Me | H | F | H | A |
| 53 | H | H | S-iPr | S-Me | H | H | F | H | A |
| 54 | H | H | S-tBu | S-Me | Me | F | H | H | A |
| 55 | H | H | S-iPr | S-Me | Me | F | H | H | A |
| 56 | H | H | S-(2R-EtOH) | S-Me | Me | F | H | H | A |
| 57 | H | H | S-iPr | S-Me | Me | H | F | H | A |
| 58 | H | H | S-(2R-EtOH) | S-Me | Me | H | F | H | A |
| 59 | H | H | S-tBu | S-Me | Me | H | F | H | A |
| 60 | H | H | R-tBu | R-Me | Me | H | F | H | C |
| 61 | H | H | R-iPr | R-Me | H | H | H | H | D |

Further Examples

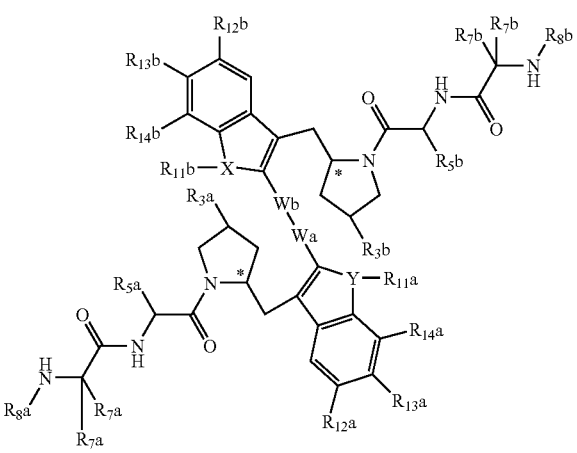

Example 2

Wherein R7a and R7b are independently H, alkyl, cycloalkyl, haloalkyl; or R8a and R7a and R8b and R7b can independently or together form a ring such as an aziridine or azetidine ring;

R8a and R8b are independently H, hydroxyl, alkyl, aryl, arylalkyl, cycloalkyl, cycloalkylalkyl, heteroaryl, or heteroarylalkyl wherein each alkyl, aryl, arylalkyl, cycloalkyl, cycloalkylalkyl, heteroaryl, and heteroarylalkyl is optionally-substituted with halogen, hydroxyl, mercapto, carboxyl, alkyl, alkoxy, amino, and nitro; or R8a and R7a and R8b and R7b can independently or together form a ring such as an aziridine or azetidine ring;

where R5a and R5b are independently H, alkyl, cycloalkyl, cycloalkylalkyl, heterocycloalkyl, aryl, arylalkyl, heteroaryl, heteroarylalkyl; or each optionally-substituted with hydroxyl, mercapto, halogen, amino, carboxyl, alkyl, haloalkyl, alkoxy, or alkylthio; or, in some instances, the R5a and R5b residues are connected by an alkylene, alkenylene, alkynylene of 2 to 12 carbon atoms or optionally-substituted alkylene, alkenylene, alkynylene bridge of 2 to 12 carbon atoms where one or more carbon atoms can be replaced with N, O, or S;

R12a, R12b, R13a, R13b, R14a, and R14b are independently H, Cl, Br, F, alkyl, cycloalkyl, hydroxy, alkoxy, amino, alkylamino, cyano, or CO$_2$H;

R3a and R3b are independently H, halogen, alkyl, aryl, arylalkyl, amino, arylamino, arylalkylamino, hydroxy, alkyloxy, aryloxy, arylalkylhydroxy, dialkylamino, amido, sulfonamido, or amidino;

X and Y are independently O, N, S, or C=C;

R11a and R11b are independently absent, H, alkyl, optionally-substituted alkyl, hydroxyalkyl, alkoxyalkyl; or R11a and R11b together form an alkylene, alkenylene, alkynlyene, or alkyloxyalkylene chain of 2 to 12 carbon atoms where one or more carbon atoms can be replaced with N, O, or S;

Wa and Wb together are a bond, alkylene, alkenylene, alkynylene, aryl, heteroaryl, or an optionally-substituted alkylene, alkenylene, alkynylene chain of 2 to 12 carbon atoms where one or more carbon atoms can be replaced with N, O, or S.

| Entry | R8a | R7a | R5a | Stereochem at Position (*) | X | Y | R11 | Wa-Wb | R3a | R3b | R5b | R7b | R8b | R12 | R13 | R14 | $K_D$ Range |
|---|---|---|---|---|---|---|---|---|---|---|---|---|---|---|---|---|---|
| 62 | H | H | S-iPr | S | O | O | na | 1,4-phenyl | H | H | S-iPr | H | H | H | H | H | B |
| 62 | H | H | S-tBu | S | N | N | CH$_2$CH$_2$OH | 1,4-phenyl | H | H | S-tBu | H | H | H | F | H | B |
| 63 | H | Me | S-tBu | S | N | N | CH$_2$CH$_2$OAc | 1,4-phenyl | H | H | S-tBu | Me | H | H | F | H | B |

Further Examples

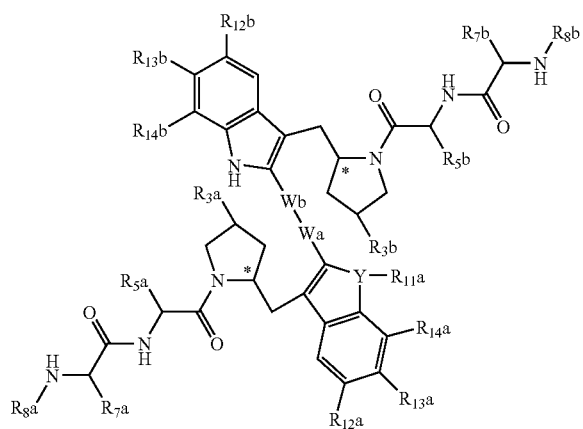

Example 3

Wherein R7a and R7b are independently H, alkyl, cycloalkyl, haloalkyl; or R8a and R7a and R8b and R7b can independently or together form a ring such as an aziridine or azetidine ring;

R8a and R8b are independently H, hydroxyl, alkyl, aryl, arylalkyl, cycloalkyl, cycloalkylalkyl, heteroaryl, or heteroarylalkyl wherein each alkyl, aryl, arylalkyl, cycloalkyl, cycloalkylalkyl, heteroaryl, and heteroarylalkyl is optionally-substituted with halogen, hydroxyl, mercapto, carboxyl, alkyl, alkoxy, amino, and nitro; or R8a and R7a and R8b and R7b can independently or together form a ring such as an aziridine or azetidine ring;

R5a and R5b are independently H, alkyl, cycloalkyl, cycloalkylalkyl, heterocycloalkyl, aryl, arylalkyl, heteroaryl, heteroarylalkyl; or each optionally-substituted with hydroxyl, mercapto, halogen, amino, carboxyl, alkyl, haloalkyl, alkoxy, or alkylthio; or, in some instances, the R5a and R5b residues are connected by an alkylene, alkenylene, alkynylene bridge of 2 to 12 carbon atoms or optionally-substituted alkylene, alkenylene, alkynylene bridge of 2 to 12 carbon atoms where one or more carbon atoms can be replaced with N, O, or S;

R12a, R12b, R13a, R13b, R14a, and R14b are independently H, Cl, Br, F, alkyl, cycloalkyl, hydroxy, alkoxy, amino, alkylamino, cyano, or CO$_2$H;

R3a and R3b are independently H, halogen, alkyl, aryl, arylalkyl, amino, arylamino, arylalkylamino, hydroxy, alkyloxy, aryloxy, arylalkylhydroxy, dialkylamino, amido, sulfonamido, or amidino;

X is O, N, S, or C=C;

R11a and R11b are independently absent, H, alkyl, optionally-substituted alkyl, hydroxyalkyl, alkoxyalkyl; or R11a and R11b together form an alkylene, alkenylene, alkynlyene, or alkyloxyalkylene chain of 2 to 12 carbon atoms where one or more carbon atoms can be replaced with N, O, or S;

Wa and Wb together are a bond, alkylene, alkenylene, alkynylene, aryl, heteroaryl, or an optionally-substituted alkylene, alkenylene, alkynylene chain of 2 to 12 carbon atoms where one or more carbon atoms can be replaced with N, O, or S.

| Entry | R8a | R7a | R5a | Stereochem at Position (*) | X | R11a | Wa-Wb | R3a | R3b | R5b | R7b | R8b | R12 | R13 | R14 | $K_D$ Range |
|---|---|---|---|---|---|---|---|---|---|---|---|---|---|---|---|---|
| 64 | Me | S-Me | S-iPr | S | N | CH$_2$CH$_2$OAc | 1,4-phenyl | H | H | S-iPr | S-Me | Me | H | F | H | A |
| 65 | H | H | S-iPr | S | N | CH$_2$CH$_2$OAc | 1,4-phenyl | H | H | S-iPr | H | H | H | F | H | B |
| 66 | Me | S-Me | S-tBu | S | N | CH$_2$CH$_2$OAc | 1,4-phenyl | H | H | S-tBu | S-Me | Me | H | F | H | A |
| 67 | Me | S-Me | S-iPr | S | N | CH$_2$CH$_2$OH | 1,4-phenyl | H | H | S-iPr | S-Me | Me | H | F | H | A |
| 68 | H | H | S-iPr | S | N | CH$_2$CH$_2$OH | 1,4-phenyl | H | H | S-iPr | H | H | H | F | H | C |
| 69 | Me | S-Me | S-tBu | S | N | CH$_2$CH$_2$OH | 1,4-phenyl | H | H | S-tBu | S-Me | Me | H | F | H | A |
| 70 | Me | R-Me | S-iPr | S | N | CH$_2$CH$_2$OAc | 1,4-phenyl | H | H | S-iPr | R-Me | Me | H | F | H | A |
| 71 | Me | R-Me | S-tBu | S | N | CH$_2$CH$_2$OH | 1,4-phenyl | H | H | S-tBu | R-Me | Me | H | F | H | B |

Scheme VI

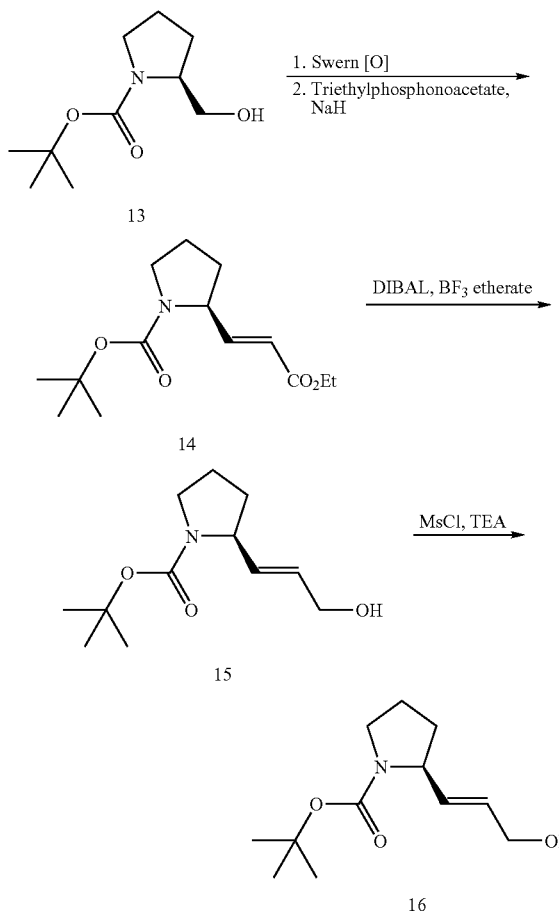

See: Macor, J. E.; Blank, D. H.; Post, R. J.; Ryan, K. *Tetrahedron Lett.* 1992, 33(52), 8011-8014.

2-(2-Ethoxycarbonyl-vinyl)-pyrrolidine-1-carboxylic acid tert-butyl ester (14)

A 2 L, 3-necked round bottomed flask equipped with an overhead stirred and a nitrogen inlet was charged with a solution of oxalyl chloride (130 mL g, 0.26 mol) in DCM (250 mL). The solution was cooled to −78° C. A solution of DMSO (20 mL, 0.28 mol) in DCM (30 mL) was added dropwise. After 30 min, a solution of alcohol 13 (40 g, 0.20 mol) in DCM (200 mL) was added dropwise. After 30 min, TEA (140 mL, 1.00 mol) was added to the solution. The solution was transferred to an ice/water bath (0° C.). and stirring was continued for 30 min [NB: reaction mixture was a thick, white slurry]. TLC analysis revealed no remaining starting material [1:1 hexane/EtOAc, $R_f(13)$=0.4; $R_f$(aldehyde)=0.6]. The reaction mixture was diluted with DCM (200 mL) and washed successively with $H_2O$, 1 M HCl, saturated $NaHCO_3$, and brine. The DCM layer was dried over $Na_2SO_4$, filtered, and concentrated to afford crude 2-formyl-pyrrolidine-1-carboxylic acid tert-butyl ester (40 g) as an oil which was used without further purification. $^1$H NMR ($CDCl_3$, 300 MHz) δ9.50 (d, J=24 Hz, 1H), 4.20-4.03 (m, 1H), 3.60-3.40 (m, 2H), 2.20-1.87 (m, 4H), 1.43 (s, 9H) ppm.

A 2 L, 3-necked round bottomed flask equipped with an overhead stirred and nitrogen inlet was charged with NaH (60%, 10.0 g, 0.25 mol) and anhydrous THF (200 mL). To the stirred mixture was slowly added triethylphosphonoacetate (53.8 g, 0.24 mol) over 20 minutes. A solution of crude 2-formyl-pyrrolidine-1-carboxylic acid tert-butyl ester (40 g, 0.20 mol) in THF (75 mL) was added dropwise. The solution turned orange and the stirring was continued for 1 h until no aldehyde remained by TLC analysis [1:1 hexane/EtOAc, $R_f$(aldehyde)=0.6; $R_f$(14)=0.8]. The solution was diluted with EtOAc and brine and the layers were separated. The EtOAc layer was washed with 1M HCl, brine, dried over anhydrous $Na_2SO_4$, filtered, and concentrated to afford 14 (67 g) as a yellow oil which was used without further purification. $^1$H NMR ($CDCl_3$, 300 MHz) δ6.92-6.76 (m, 1H), 5.82 (d, 1H), 4.56-4.32 (m, 1H), 4.25-4.12 (m, 2H), 3.48-3.27 (m, 2H), 2.20-1.98 (m, 1H), 1.91-1.72 (m, 2H), 1.43 (s, 9H), 1.25 (t, 3H) ppm.

2-(3-Hydroxy-propenyl)-pyrrolidine-1-carboxylic acid tert-butyl ester (15)

A 2 L, 3-necked round bottomed flask equipped with an overhead stirred was charged with 14 (67 g, 0.20 mol) and DCM (400 mL). The solution was cooled to −78° C. To this solution was slowly added boron trifluoride etherate (30 mL, 0.20 mol). The reaction mixture was stirred for 30 min. DIBAL (1 M in DCM, 600 mL, 0.6 mol) was added at a moderate rate. The solution was stirred at −78° C. for 2 h and then treated with EtOAc (100 mL) over 30 min to discharge remaining reagent. The reaction mixture was allowed to warm to −5° C. The reaction mixture was CAREFULLY quenched by the dropwise addition of 1 M HCl. The reaction mixture was diluted with DCM and $H_2O$ and made acidic to dissolve aluminum salts. The layers were separated and the organic phase was washed successively with dilute aqueous HCl, water, and brine. The DCM layer was dried over $Na_2SO_4$, filtered, and concentrated. The residue was purified by flash chromatography ($SiO_2$, 25% to 80% EtOAc/hexane) to afford 15 as a yellow oil (36 g, 79%). [TLC analysis, 1:1 hexane/EtOAc, $R_f$(14)=0.8; $R_f$(15)=0.2]. $^1$H NMR ($CDCl_3$, 300 MHz) δ5.73-5.52 (m, 2H), 4.39-4.16 (m, 1H), 4.15-4.04 (m, 2H), 3.46-3.25 (m, 2H), 2.92 (br s, 1H), 2.08-1.93 (m, 1H), 1.92-1.79 (m, 2H), 1.78-1.62 (m, 1H), 1.42 (s, 9H) ppm.

trans-2S-(3-Methanesulfonyloxy-propenyl)-pyrrolidine-1-carboxylic acid tert-butyl ester (16)

To a solution of 15 (19 g, 84 mmol) in DCM (100 mL) was added triethylamine (10 g, 13.9 mL, 100 mmol). The solution was cooled to 0° C. and methanesulfonyl chloride (9.6 g, 6.5 mL, 84 mmol) in DCM (20 mL) was added dropwise. After 1 h, TLC analysis revealed complete consumption of 15 [1:1 hexane/EtOAc, $R_f$(15)=0.2; $R_f$(16)=0.6]. Brine was added and the product was extracted with DCM (3×50 mL). The organic extracts were combined and washed with 1 N HCl, water, brine, dried over anhydrous $Na_2SO_4$, filtered, and concentrated to afford 21.4 g of 16 which was used without purification. $^1$H NMR ($CDCl_3$, 300 MHz) δ4.4-4.0 (m, 2H), 3.42-3.21 (m, 3H), 3.0 (s, 3H), 2.00-1.6 (m, 4H), 1.42 (s, 9H) ppm.

Scheme VII

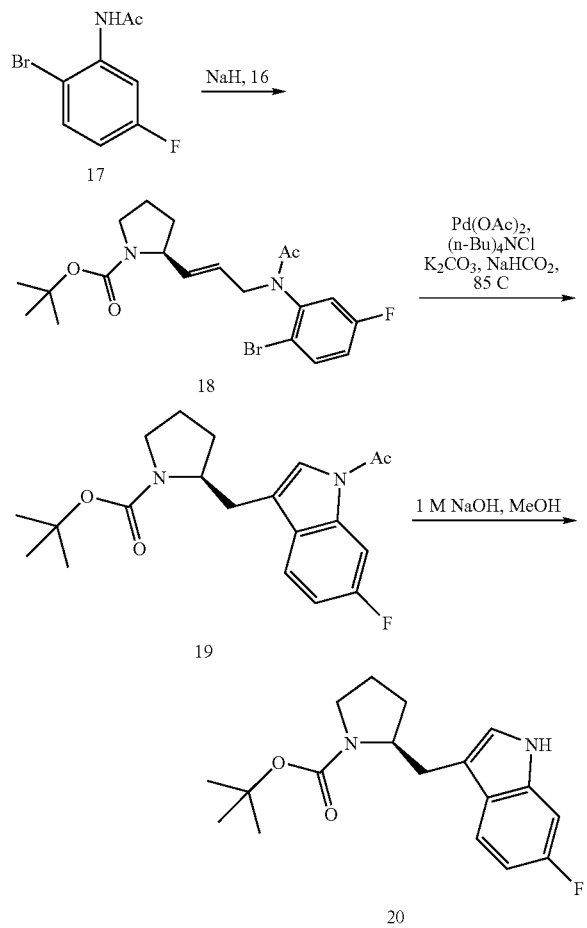

2-{3-[Acetyl-(2-bromo-5-fluoro-phenyl)-amino]-propenyl}-pyrrolidine-1-carboxylic acid tert-butyl ester (18)

To a suspension of 60% NaH (9.2 g, 0.23 mol) in anhydrous DMF (150 mL) at 0° C. was added 2-bromo-5-fluoroacetanilide (17, 53.4 g, 0.23 mol) in small portions. After 1 h, a solution of crude mesylate 16 (approx. 0.19 mol) in DMF (20 mL) was added in a dropwise fashion from an addition funnel. The reaction mixture was allowed to warm to ambient temperature overnight. The reaction mixture was recooled to 0° C. and carefully quenched by the addition of brine and neutralized by the addition of dilute aqueous HCl until pH=7. The mixture was diluted with diethyl ether and water and the layers were separated. The organic phase was washed several times with water to remove DMF followed by washing with brine, dried over anhydrous $Na_2SO_4$, filtered, and concentrated. The crude product was purified by flash silica gel chromatography (0.5% to 2% MeOH/DCM) to afford 66 g of 18 as an oil. [TLC analysis, 1:1 hexane/EtOAc, $R_f(16)$=0.5; $R_f(17)$=0.6; $R_f(18)$=0.4]. $^1$H NMR (CDCl$_3$, 300 MHz) δ7.64 (m, 1H), 7.01 (m, 2H), 5.52 (m, 1H), 5.39 (app dd, J=6.0, 15.3 Hz, 1H), 4.77 (app dd, J=4.5, 13.8 Hz, 1H), 4.24 (m, 1H), 3.67 (app dd, J=7.5, 13.8 Hz, 1H), 3.32 (m, 2H), 1.90 (m, 1H), 1.81 (m, 3H), 1.75 (m, 2H), 1.57 (m, 1H), 1.43 (m, 9H) ppm.

2-(1-Acetyl-6-fluoro-1H-indol-3-ylmethyl)-pyrrolidine-1-carboxylic acid tert-butyl ester (19)

Under a nitrogen atmosphere, a solution of 18 (66 g, 0.15 mol) in anhydrous DMF (350 mL) was charged with (n-Bu)$_4$NCl (41.5 g, 0.15 mol), $K_2CO_3$ (20.6 g, 0.15 mol), NaHCO$_2$ (10.2 g, 0.15 mol), and Pd(OAc)$_2$ (3.35 g, 0.015 mol) at ambient temperature. The heterogeneous mixture was immersed in a pre-heated (85° C.) oil bath. After 1 h, TLC analysis revealed some 18 remained therefore more catalyst (1 g) was added. After 1.5 h, another charge of catalyst (0.6 g) was added. After an additional 1.5 h of heating, 18 had been completely consumed by TLC analysis [TLC analysis, 2% MeOH/DCM, $R_f(18)$=0.7; $R_f(19)$=0.8]. The warm reaction mixture was transferred to an ice water bath to cool then diluted with diethyl ether and filtered through a pad of celite. The solids were washed with diethyl ether and the filtrate was washed several times with water to remove DMF then once with brine, dried over anhydrous $Na_2SO_4$, filtered, and concentrated to afford 52.5 g of crude 19 which was used without further purification. $^1$H NMR (CDCl$_3$, 300 MHz) δ8.18 (m, 1H), 7.60 (m, 1H), 7.18 (m, 1H), 7.05 (dt, J=2.4, 8.7 Hz, 1H), 4.13 (m, 1H), 3.41 (m, 1H), 3.33 (m, 2H), 3.17 (app dd, J=14.1, 38.1 Hz, 1H), 2.61 (s, 3H), 1.83 (m, 3H), 1.69 (m, 1H), 1.49 (s, 9H) ppm.

2-(6-Fluoro-1H-indol-3-ylmethyl)-pyrrolidine-1-carboxylic acid tert-butyl ester (20)

A solution containing crude 19 (48 g) in reagent grade MeOH (480 mL) was cooled to 0° C. Aqueous NaOH (1 M, 144 mL) was added in one portion. After 30 min, TLC analysis revealed complete consumption of starting material [TLC analysis, 3:2 hexane/EtOAc, $R_f(19)$=0.7; $R_f(20)$=0.8]. The reaction mixture was neutralized with 1 N HCl and the product was extracted with DCM. The DCM extracts were washed with water, brine, dried over anhydrous $Na_2SO_4$, filtered, and concentrated. The crude product was absorbed onto 200 mL of silica gel and chromatographed (80% to 65% hexane/EtOAc) to afford 31.7 g of 20 as a thick oil. $^1$H NMR (CDCl$_3$, 300 MHz) δ8.11 (br s, 1H), 7.65-7.57 (m, 1H), 7.04 (m, 1H), 6.96 (s, 1H), 6.87 (t, J=2.8 Hz, 1H), 4.16-4.09 (m, 1H), 3.45-3.14 (m, 3H), 2.76-2.63 (m, 1H), 1.75 (br s, 4H), 1.58 (s, 9H) ppm.

Scheme VIII

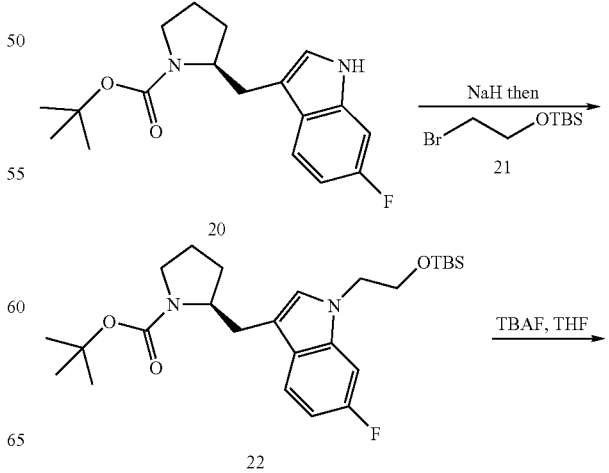

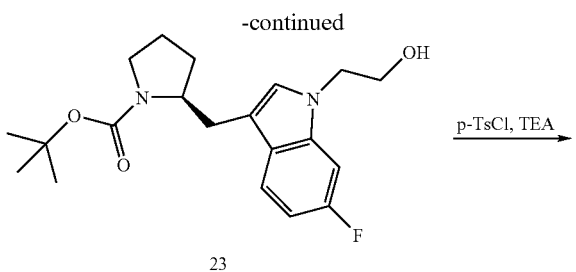

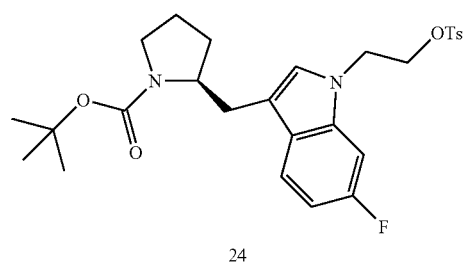

2-{1-[2-(tert-Butyl-dimethyl-silanyloxy)-ethyl]-6-fluoro-1H-indol-3-ylmethyl}-pyrrolidine-1-carboxylic acid tert-butyl ester (22)

Under a nitrogen atmosphere, a solution of 20 (3.0 g, 9.42 mmol) in anhydrous DMF (40 mL) was added via addition funnel to a mixture of 60% NaH (0.45 g, 11.3 mmol) in DMF (10 mL) at 0° C. After 1 h, bromide 21 (2.47 g, 2.22 mL, 10.3 mmol) in DMF (5 mL) was added via syringe. After 30 min, the reaction mixture was warmed to ambient temperature and stirred for an additional 30 min. The reaction was quenched by the addition of saturated aqueous $NH_4Cl$ and diluted with water. The product was extracted with diethyl ether and the combined ether extracts were washed several times with water to remove DMF, brine, dried over anhydrous $Na_2SO_4$, filtered, and concentrated to afford 4.49 g (quant.) of 22 as a yellow oil which was used without further purification. TLC analysis [3:1 hexane/EtOAc, $R_f(20)$=0.4; $R_f(22)$=0.7]. $^1$H NMR ($CDCl_3$, 300 MHz) δ7.68 (m, 1H), 7.12 (d, J=3.3 Hz, 1H), 7.03 (s, 1H), 6.98 (t, J=3.2 Hz, 1H), 4.26-4.23 (m, 3H), 4.05-3.99 (m, 2H), 3.55-3.27 (m, 3H), 2.75 (m, 1H), 1.88 (br s, 4H), 1.67 (s, 9H), 1.33 (m, 1H), 1.06-1.00 (m, 3H), 0.95 (s, 9H), 0.23-0.14 (m, 2H) ppm.

2-[6-Fluoro-1-(2-hydroxy-ethyl)-1H-indol-3-ylmethyl]-pyrrolidine-1-carboxylic acid tert-butyl ester (23)

A solution containing 22 (4.49 g, 9.42 mmol) in anhydrous THF (50 mL) was cooled to 0° C. Tetra-n-butylammonium fluoride (1 M in THF, 14 mL, 14 mmol) was added via syringe. After 1 h, reaction complete by TLC analysis [3:1 hexane/EtOAc, $R_f(22)$=0.7; $R_f(23)$=0.1] therefore diluted with EtOAc. The EtOAc solution was washed twice with 1 M HCl, water, brine, dried over anhydrous $Na_2SO_4$, filtered, and concentrated to afford 3.9 g of 23 (>100%; contaminated with some TBS-containing impurities) as a tan-colored oil which was used without further purification. $^1$H NMR ($CDCl_3$, 300 MHz) δ7.59 (br s, 1H), 7.01-6.85 (m, 3H), 4.19-4.10 (m, 3H), 3.90 (br s, 2H), 3.38-3.31 (m, 2H), 3.15 (dd, J=1.4, 4.6 Hz, 1H), 2.68 (m, 1H), 1.79-1.72 (m, 4H), 1.47 (d, J=10.9 Hz, 9H) ppm.

2-{6-Fluoro-1-[2-(toluene-4-sulfonyloxy)-ethyl]-1H-indol-3-ylmethyl}-pyrrolidine-1-carboxylic acid tert-butyl ester (12)

Triethylamine (1.13 g, 1.56 mL, 11.2 mmol) was added to a solution of 23 (3.4 g, 9.38 mmol) in anhydrous DCM (50 mL) at 0° C. followed by the addition of p-TsCl (1.79 g, 9.38 mmol) and DMAP (0.12 g, 0.94 mmol). After 30 min, the reaction mixture was warmed to room temperature. Upon complete consumption of 23 (~30 min at ambient temperature), the reaction mixture was diluted with DCM and washed twice with 1 M HCl, brine, dried over anhydrous $Na_2SO_4$, filtered, and concentrated. The crude tosylate was purified by flash silica gel chromatography (3:1 hexane/EtOAc) to afford 3.67 g (76%) of 24 as a white foam which was homogeneous by TLC analysis [3:1 hexane/EtOAc, $R_f(23)$=0.1; $R_f(24)$=0.3]. $^1$H NMR ($CDCl_3$, 300 MHz) δ7.64-7.45 (m, 3H), 7.11 (t, J=2.5 Hz, 2H), 6.85 (dd, J=0.8, 3.3 Hz, 1H), 6.79 (s, 1H), 6.73 (t, J=3.6 Hz, 1H), 4.25 (s, 4H), 4.08 (br s, 1H), 3.34 (br d, J=9.6 Hz, 2H), 3.20-3.09 (m, 1H), 2.64-2.57 (m, 1H), 2.36 (s, 1H), 1.75 (br s, 4H), 1.53 (s, 9H) ppm.

Scheme IX

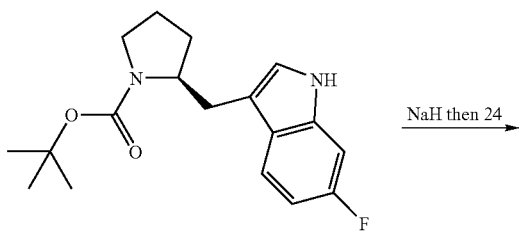

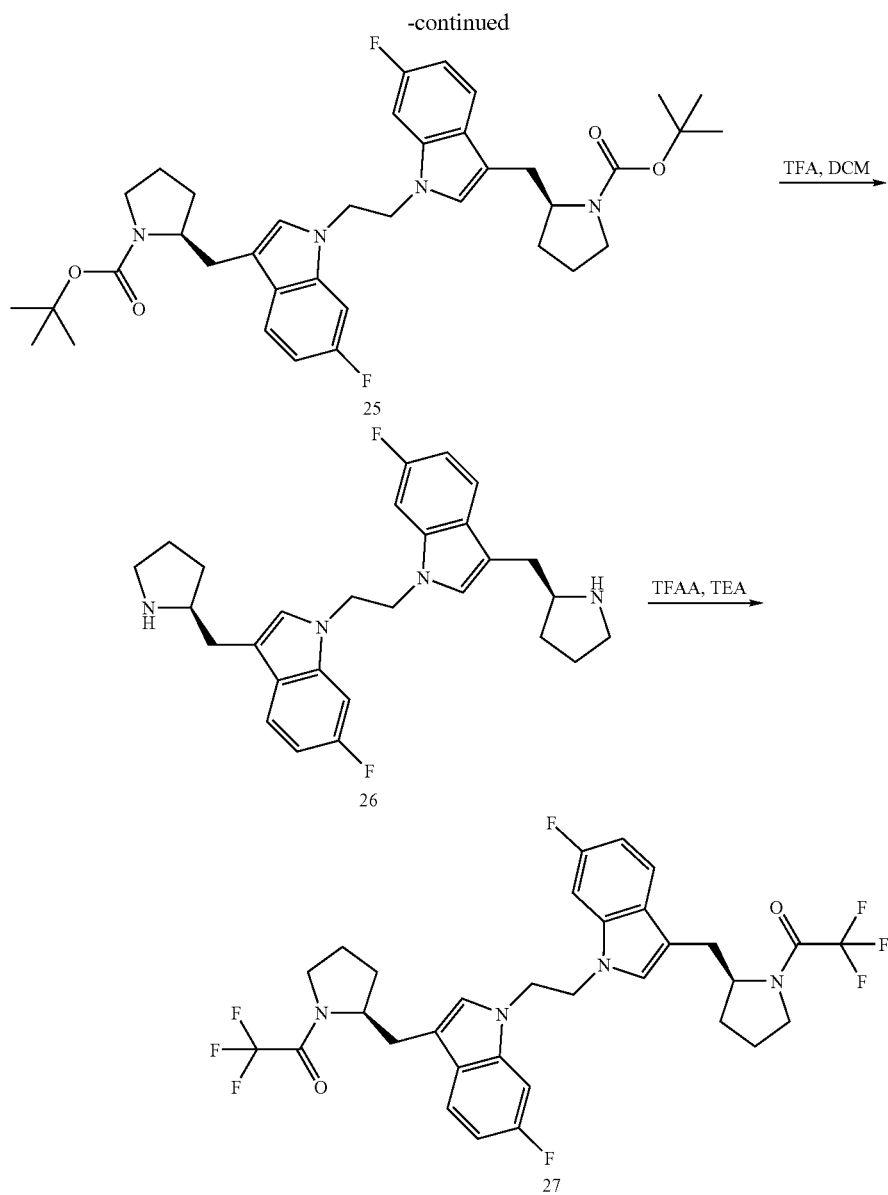

1,2-Bis[2-(6-Fluoro-1H-indol-3-ylmethyl)-pyrrolidine-1-carboxylic acid tert-butyl ester]ethane (25)

To a suspension of 60% NaH (0.34 g, 8.50 mmol) in anhydrous DMF (20 mL) at 0° C. was added a solution of 20 (2.47 g, 7.75 mmol) in DMF (30 mL) via addition funnel. After 1 h, the reaction mixture was transferred to a −40° C. bath (ACN/dry ice). At −40° C., a solution of tosylate 24 (3.65 g, 7.06 mmol) in DMF (20 mL) was added to the cold anion solution from an addition funnel. After 30 min, only starting materials observed by TLC analysis therefore slowly warmed to 0° C. over 2 h. After 2-3 h at 0° C., the reaction was quenched by the addition of saturated aqueous $NH_4Cl$. The mixture was diluted with diethyl ether and water and the layers were separated. The ether layer was washed several times with water to remove DMF then once with brine, dried over anhydrous $Na_2SO_4$, filtered, and concentrated. The crude product was purified by normal phase HPLC (10-100% EtOAc/hexane over 30 min) to afford 3.27 g (70%) of 25 as a white foam which was homogeneous by TLC analysis [3:1 hexane/EtOAc (two developments), $R_f(20)$=0.8; $R_f(24)$=0.55; $R_f(25)$= 0.5]. $^1$H NMR ($CDCl_3$, 300 MHz) δ7.61-7.52 (m, 1H), 6.82 (t, J=9.6 Hz, 1H), 6.68-6.61 (m, 1H), 6.48-6.46 (m, 1H), 4.34 (s, 2H), 3.93 (m, 1H), 3.34-3.26 (m, 2H), 3.17-3.01 (m, 1H), 2.05 (m, 1H), 1.70-1.58 (m, 4H), 1.50 (s, 9H) ppm.

1,2-Bis[2-(6-Fluoro-1H-indol-3-ylmethyl)-pyrrolidine]ethane (26)

Trifluoroacetic acid (2 mL) was added at 0° C. to a solution containing 25 (3.27 g, 4.93 mmol) in DCM (10 mL). After 3 h, an additional portion of TFA (2 mL) was added and the reaction was complete within 1 h. The solvent was removed on a rotary evaporator and the residue was dissolved in DCM and washed twice with saturated aqueous $NaHCO_3$, once with brine, dried over anhydrous $Na_2SO_4$, filtered, and concentrated to afford 26 as a yellow foam which was used without further purification. $^1$H NMR ($CDCl_3$, 300 MHz)

δ7.31 (dd, J=5.1, 8.7 Hz, 1H), 6.92 (s, 1H), 6.77 (ddd, J=2.4, 9.6, 11.1 Hz, 1H), 6.44 (dd, J=2.4, 9.9 Hz, 1H), 4.41 (s, 2H), 3.65-3.55 (m, 1H), 3.24-3.16 (m, 1H), 3.01-2.96 (m, 1H), 2.92 (d, J=7.8 Hz, 2H), 2.15-1.99 (m, 1H), 1.96-1.84 (m, 2H), 1.76-1.67 (m, 1H) ppm.

1,2-Bis{2,2,2-Trifluoro-1-[2-(6-fluoro-1H-indol-3-ylmethyl)-pyrrolidin-1-yl]-ethanone}ethane (27)

At 0° C., TFAA (2.17 g, 1.44 mL, 10.3 mmol) was added to a solution containing 26 (2.28 g, 4.93 mmol; based on theoretical yield from previous step) and TEA (2.49 g, 3.43 mL, 24.6 mmol) in DCM (50 mL). After 30 min, the reaction mixture is diluted with DCM and washed twice with saturated aqueous NaHCO$_3$, once with brine, dried over anhydrous Na$_2$SO$_4$, filtered, and concentrated. The crude product was purified by flash silica gel chromatography (4:1 to 1:1 hexane/EtOAc) to afford 2.66 g (82%, 2 steps) of 27 which was homogeneous by TLC analysis [2:1 hexane/EtOAc, R$_f$(26)= 0.01; R$_f$(27)=0.5]. $^1$H NMR (CDCl$_3$, 300 MHz) δ7.70 (dd, J=5.4, 9.0 Hz, 1H), 6.84 (ddd, J=1.8, 9.3, 10.5 Hz, 1H), 6.62 (dd, J=1.8, 10.2 Hz, 1H), 6.44 (s, 1H), 4.36 (s, 2H), 4.29-4.28 (m, 1H), 3.60 (app t, J=7.2 Hz, 2H), 3.23 (dd, J=2.4, 14.1 Hz, 1H), 2.51 (dd, J=9.9, 14.1 Hz, 1H), 1.92-1.84 (m, 2H), 1.72-1.66 (m, 1H), 1.57-1.56 (m, 1H) ppm.

Scheme X

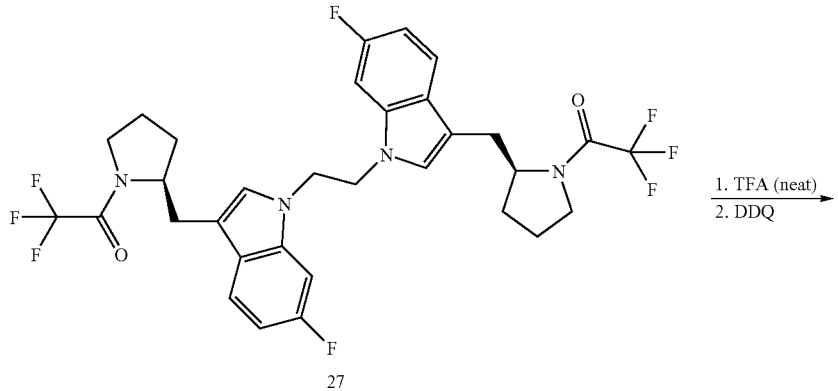

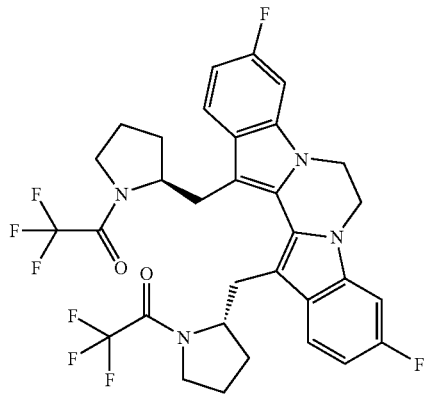

1-(2-{3,10-Difluoro-14-[1-(2,2,2-trifluoro-acetyl)-pyrrolidin-2-ylmethyl]-6,7-dihydro-pyrazino [1,2-a;4,3-a']diindol-13-ylmethyl}-pyrrolidin-1-yl)-2,2,2-trifluoro-ethanone (28)

Acyclic dimer 27 (2.66 g, 4.06 mmol) was dissolved in neat TFA (25 mL) at ambient temperature. After 3 h, the solvent was removed on a rotary evaporator and the resultant residue was dissolved in EtOAc, washed twice with saturated aqueous NaHCO$_3$, once with brine, dried over anhydrous Na$_2$SO$_4$, filtered, and concentrated to afford 2.65 g (quant.) of the diastereomeric indolylindolines as a yellow foam. [TLC analysis: 3:1 hexane/EtOAc, R$_f$(27)=0.3; R$_f$(indolylindolines)=0.6-0.7].

To a mixture of crude indolylindolines (2.65 g, 4.05 mmol) in 1,4-dioxane (50 mL) was added DDQ (1.10 g, 4.84 mmol) in one portion. After 2-3 h, the reaction mixture was diluted with EtOAc and filtered through a pad of celite. The solids were washed with EtOAc and the filtrate was washed five times with saturated aqueous NaHCO$_3$, then once with brine. The combined aqueous washes were re-extracted twice with EtOAc and the combined organic extracts were dried over anhydrous Na$_2$SO$_4$, filtered, and concentrated. The crude product was purified by flash silica gel chromatography (4:1 hexane/EtOAc) to afford 1.94 g (73%, 2 steps) of 28 as an off-white solid which was homogeneous by TLC analysis (2:1 hexane/EtOAc, R$_f$(indolylindolines)=0.6-0.7; R$_f$(28)=0.55]. NB: The product 2,2'-biindole (28) is quite fluorescent and is easily purified by trituration with reagent grade MeOH to afford a white solid. $^1$H NMR (CDCl$_3$, 300 MHz) δ8.06 (dd, J=5.1, 8.1 Hz, 1H), 7.03-6.93 (m, 2H), 4.49 (d, J=9.0 Hz, 1H), 4.40 (m, 1H), 4.12 (d, J=9.0 Hz, 1H), 3.75-3.69 (m, 2H), 3.57-3.51 (m, 2H), 2.85 (dd, J=10.5, 12.9 Hz, 1H), 1.78-1.74 (m, 2H), 1.51-1.45 (m, 1H) ppm.

Scheme XI

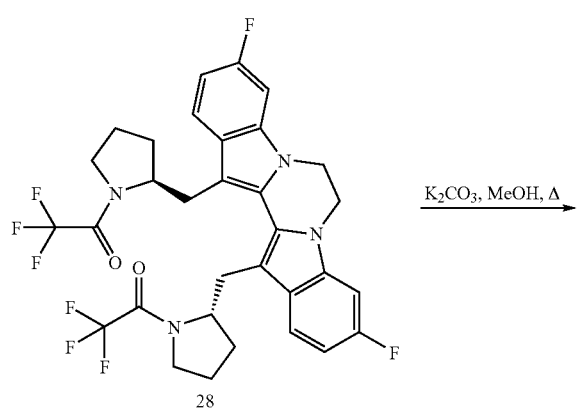

28

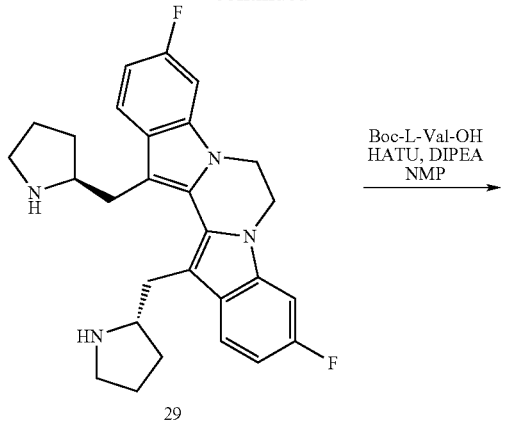

29

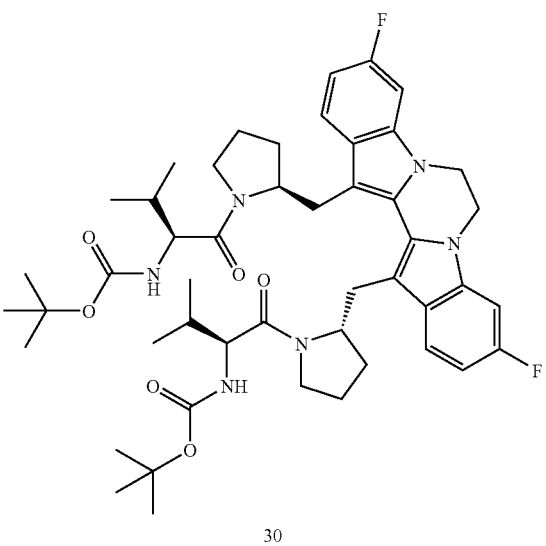

30

3,10-Difluoro-13,14-bis-pyrrolidin-2-ylmethyl-6,7-dihydro-pyrazino[1,2-a;4,3-a]diindole (29)

A mixture containing 28 (1.94 g, 2.97 mmol) and K$_2$CO$_3$ (2.05 g, 14.8 mmol) in MeOH (60 mL) was heated at 60° C. for 1.5 h. The reaction mixture was cooled to ambient temperature and diluted with EtOAc and water. The layers were separated and the aqueous phase was extracted three times with EtOAc. The combined organic extracts were washed with brine, dried over anhydrous Na$_2$SO$_4$, filtered, and concentrated to afford 1.57 g (quant.) of 29 as a yellow solid which was used without further purification. TLC analysis, 1:1 hexane/EtOAc, R$_f$(28)=0.9; R$_f$(29)=0.01. $^1$H NMR (CDCl$_3$, 300 MHz) δ7.65 (m, 1H), 6.98 (app d, J=8.2 Hz, 1H), 6.90 (app t, J=8.3 Hz, 1H), 4.31 (s, 2H), 3.97 (br s, 3H), 3.54 (m, 1H), 3.31 (m, 1H), 3.14 (m, 1H), 2.97 (m, 1H), 1.83 (m, 1H), 1.68 (m, 2H), 1.42 (m, 1H) ppm. $^{13}$C NMR (CDCl$_3$, 75 MHz) δ160.6 (d, J$_{C-F}$=238.7 Hz), 136.2 (d, J$_{C-F}$=12.0 Hz), 127.1, 125.4, 120.8 (d, J$_{C-F}$=10.2 Hz), 109.8, 108.9 (d, J$_{C-F}$=24.6 Hz), 95.3 (d, J$_{C-F}$=26.3 Hz), 59.6, 45.6, 41.6, 31.0, 30.7, 24.5 ppm.

[1-(2-{14-[1-(2-tert-Butoxycarbonylamino-3-methyl-butyryl)-pyrrolidin-2-ylmethyl]-3,10-difluoro-6,7-dihydro-pyrazino[1,2-a;4,3-a']diindol-13-ylmethyl}-pyrrolidine-1-carbonyl)-2-methyl-propyl]-carbamic acid tert-butyl ester (30)

A solution containing Boc-L-Val-OH (0.69 g, 3.18 mmol) and HATU (1.27 g, 3.34 mmol) in anhydrous NMP (4 mL) was cooled to 0° C. After 15 min, DIPEA (0.45 g, 0.61 mL, 3.50 mmol) was added via syringe. After 15 min, a solution containing 29 (0.70 g, 1.52 mmol) in NMP (4 mL) was added and the reaction mixture was allowed to warm to ambient temperature over 2 h at which point TLC analysis revealed complete consumption of 29 [TLC analysis, 2:1 hexane/EtOAc, $R_f$(29)=0.01; $R_f$(30)=0.5]. The reaction mixture was diluted with diethyl ether and washed once with dilute aqueous HCl, five times with water to remove excess NMP, once with saturated aqueous NaHCO$_3$ and brine, dried over anhydrous Na$_2$SO$_4$, filtered, and concentrated. The crude product was purified by flash silica gel chromatography (3:1 hexane/EtOAc) to afford 1.09 g (83%) of 30 as a pale yellow solid. $^1$H NMR (CDCl$_3$, 300 MHz) δ8.04 (dd, J=5.1, 8.7 Hz, 1H), 6.98 (m, 2H), 5.33 (d, J=9.3 Hz, 1H), 4.50 (m, 1H), 4.49 (d, J=8.1 Hz, 1H), 4.24 (dd, J=7.2, 9.3 Hz, 1H), 4.11 (m, 2H), 3.67 (dd, J=3.0, 13.5 Hz, 1H), 3.56 (m, 2H), 2.73 (app t, J=12.9 Hz, 1H), 1.99 (dd, J=7.2, 13.5 Hz, 1H), 1.70-1.17 (m, 2H), 1.43 (s, 9H), 1.01 (d, J=7.2 Hz, 3H), 0.98 (d, J=7.5 Hz, 3H) ppm. $^{13}$C NMR (CDCl$_3$, 75 MHz) δ171.2, 160.4 (d, $J_{C-F}$=238 Hz), 155.7, 136.6 (d, $J_{C-F}$=12.0 Hz), 127.2, 124.8, 122.0 (d, $J_{C-F}$=9.7 Hz), 109.2, 108.5 (d, $J_{C-F}$=24.0 Hz), 95.0 (d, $J_{C-F}$=26.3 Hz), 79.4, 57.7, 56.9, 47.3, 41.7, 31.8, 29.7, 28.4, 28.3, 23.8, 19.7, 17.7 ppm.

Scheme XII

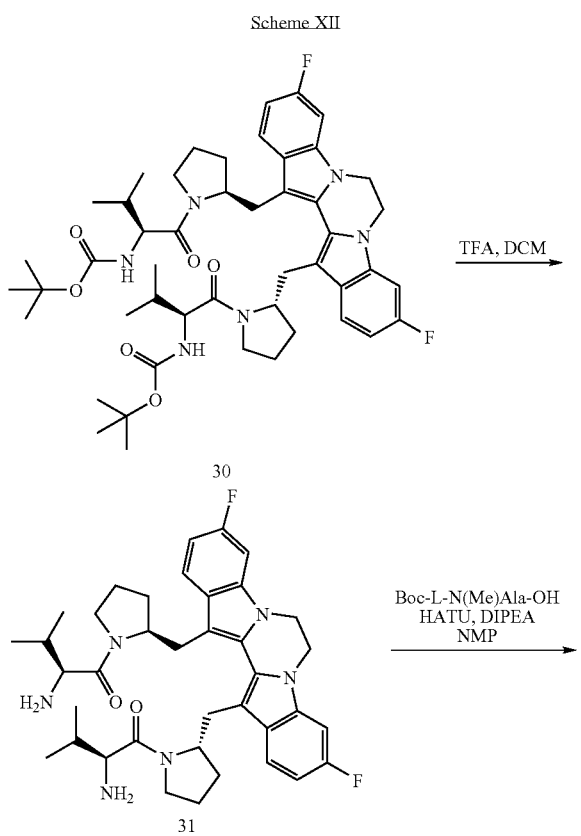

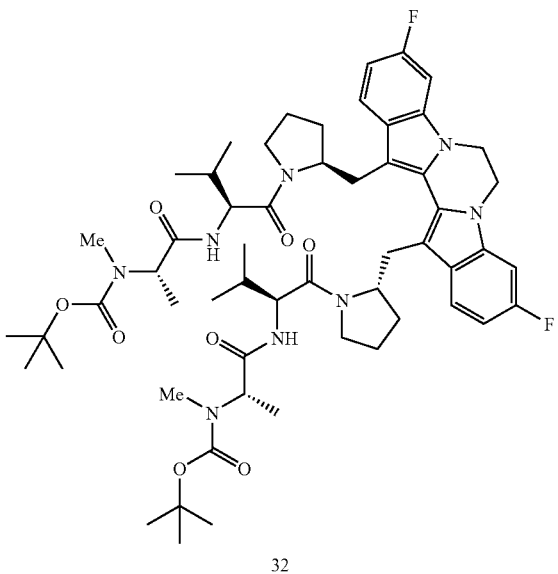

32

2-Amino-1-(2-{14-[1-(2-amino-3-methyl-butyryl)-pyrrolidin-2-ylmethyl]-3,10-difluoro-6,7-dihydro-pyrazino[1,2-a;4,3-a']diindol-13-ylmethyl}-pyrrolidin-1-yl)-3-methyl-butan-1-one (31)

A solution containing 30 (1.09 g, 1.27 mmol) in DCM (20 mL) was cooled to 0° C. TFA (4 mL) was added via pipette and the reaction was monitored until TLC analysis revealed complete consumption of 30 (~2 h). TLC analysis, 10% MeOH/DCM, $R_f$(30)=0.5; $R_f$(31)=0.4. The solvent was removed on a rotary evaporator and the residue was dissolved in EtOAc. The EtOAc solution was washed twice with saturated aqueous NaHCO$_3$ and once with brine. The combined aqueous washes were back-extracted with EtOAc and the organic extracts were dried over anhydrous Na$_2$SO$_4$, filtered, and concentrated to afford 0.83 g (quant.) of 31 as a yellow solid which was used without further purification. $^1$H NMR (CDCl$_3$, 300 MHz) δ8.09 (dd, J=5.1, 8.7 Hz, 1H), 6.97 (m, 2H), 4.52 (m, 1H), 4.50 (d, J=8.7 Hz, 1H), 4.11 (m, 1H), 3.71 (br d, J=11.1 Hz, 1H), 3.51-3.32 (m, 2H), 2.74 (app t, J=12.6 Hz, 1H), 2.30 (br s, 4H), 1.92 (m, 1H), 1.68 (m, 2H), 1.41 (m, 1H), 1.03 (m, 6H) ppm. $^{13}$C NMR (CDCl$_3$, 75 MHz) δ174.3, 171.4, 160.6 (d, $J_{C-F}$=232.5 Hz), 136.8 (d, $J_{C-F}$=7.5 Hz), 127.4 (d, $J_{C-F}$=3.7 Hz), 125.0, 122.4 (d, $J_{C-F}$=7.5 Hz), 109.6, 108.7 (d, $J_{C-F}$=22.5 Hz), 95.2 (d, $J_{C-F}$=22.5 Hz), 58.0, 47.3, 41.9, 30.0, 28.5, 28.5, 24.1, 19.9, 17.6 ppm.

Penultimate Intermediate (32)

A solution containing Boc-L-N(Me)Ala-OH (0.49 g, 2.45 mmol) and HATU (0.98 g, 2.56 mmol) in anhydrous NMP (4 mL) was cooled to 0° C. After 15 min, DIPEA (0.35 g, 0.47 mL, 2.69 mmol) was added via syringe. After 15 min, a solution containing 31 (0.77 g, 1.17 mmol) in NMP (4 mL) was added and the reaction mixture was allowed to warm to ambient temperature over 2 h at which point TLC analysis revealed complete consumption of 31 [TLC analysis, 1:1 hexane/EtOAc, $R_f$(31)=0.01; $R_f$(32)=0.5]. The reaction mixture was diluted with diethyl ether and washed once with dilute aqueous HCl, five times with water to remove excess NMP, once with saturated aqueous NaHCO$_3$ and brine, dried over anhydrous Na$_2$SO$_4$, filtered, and concentrated. The crude product was purified by flash silica gel chromatography (1:1 hexane/EtOAc) to afford 0.92 g (76%) of 32 as a pale yellow solid. $^1$H NMR (CDCl$_3$, 300 MHz) δ8.05 (m, 1H), 7.65-6.90 (m, 2H), 4.53 (m, 3H), 4.13 (m, 1H), 3.70-3.52 (m, 4H), 2.82 (m, 2H), 2.72 (app t, J=11.1 Hz, 1H), 1.70 (m, 1H), 1.64 (s, 3H), 1.53 (s, 9H), 1.45-1.25 (m, 2H), 1.34 (d, J=7.0 Hz, 3H), 1.05-0.88 (m, 6H) ppm. $^{13}$C NMR (CDCl$_3$, 75 MHz) δ171.3, 170.4, 160.4 (d, J$_{C-F}$=232.5 Hz), 136.6 (d, J$_{C-F}$=7.5 Hz), 127.2, 124.7, 122.1, 109.2, 108.5 (d, J$_{C-F}$=22.5 Hz), 95.0 (d, J$_{C-F}$=22.5 Hz), 57.8, 55.5, 47.4, 41.7, 31.6, 29.9, 29.7, 28.4, 23.8, 19.3, 18.0 ppm.

Scheme XIII

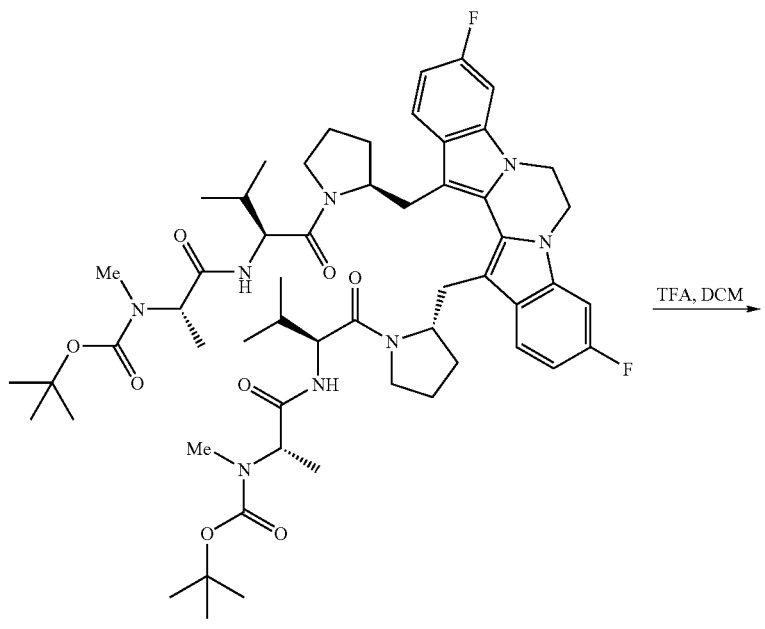

32

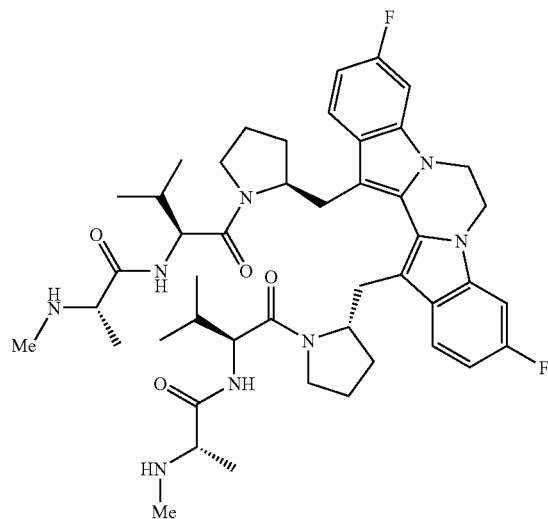

33

N-{1-[2-(3,10-Difluoro-14-{1-[3-methyl-2-(2-methylamino-propionylamino)-butyryl]-pyrrolidin-2-ylmethyl}-6,7-dihydro-pyrazino[1,2-a;4,3-a]diindol-13-ylmethyl)-pyrrolidine-1-carbonyl]-2-methyl-propyl}-2-methylamino-propionamide (33)

A solution containing 32 (0.92 g, 0.89 mmol) in DCM (15 mL) was cooled to 0° C. TFA (3 mL) was added via pipette and the reaction was monitored until TLC analysis revealed complete consumption of 32 (~3 h). TLC analysis, 10% MeOH/DCM, $R_f$(32)=0.4; $R_f$(33)=0.3. The solvent was removed on a rotary evaporator and the residue was dissolved in EtOAc. The EtOAc solution was washed twice with saturated aqueous NaHCO$_3$ and once with brine. The combined aqueous washes were back-extracted with EtOAc and the organic extracts were dried over anhydrous Na$_2$SO$_4$, filtered, and concentrated to afford 0.73 g of crude 33. The crude product was purified by RP-HPLC (Method: Solvent A: water w/0.1% v/v HOAc, Solvent B: ACN w/0.1% v/v HOAc. Dynamax Microsorb C18 60 Å 8 µ, 41.4 mm×25 cm; Flow: 40 mL/min; Detector: 272 nm). The product-containing fractions were diluted with saturated aqueous NaHCO$_3$ and extracted with EtOAc. The EtOAc extract was washed with brine, dried over anhydrous Na$_2$SO$_4$, filtered, and concentrated. The residue was dissolved in a minimum amount of ACN, diluted with water until cloudy, frozen, and lyophilized to afford 33 as a flocculent, white solid. $^1$H NMR (DMSO, 300 MHz) δ8.04-7.86 (m, 2H), 7.38 (app dd, J=2.3, 10.5 Hz, 1H), 6.90 (app dt, J=2.3, 9.9 Hz, 1H), 4.68 (app d, J=8.7 Hz, 1H), 4.34-4.23 (m, 2H), 3.98 (d, J=8.7 Hz, 1H), 3.46 (m, 2H), 2.94 (app q, J=6.4 Hz, 1H), 2.70 (t, J=12.8 Hz, 1H), 2.12 (s, 3H), 1.94 (m, 1H), 1.58 (m, 2H), 1.35 (m, 1H), 1.16-1.07 (m, 2H), 1.03 (d, J=7.0 Hz, 3H), 0.85 (m, 6H) ppm. $^{13}$C NMR (CDCl$_3$, 75 MHz) δ175.0, 170.8, 160.6 (d, $J_{C-F}$=232.5 Hz), 136.8 (d, $J_{C-F}$=7.5 Hz), 127.4 (d, $J_{C-F}$=3.7 Hz), 125.0, 122.3 (d, $J_{C-F}$=7.5 Hz), 109.5, 108.7 (d, $J_{C-F}$=22.5 Hz), 95.2 (d, $J_{C-F}$=22.5 Hz), 60.4, 57.9, 55.3, 47.6, 42.0, 35.2, 31.7, 30.0, 28.6, 24.0, 19.7, 19.6, 18.2 ppm. Mass spectrum, m/z=[415.6] (M+2)+/2.

Examples

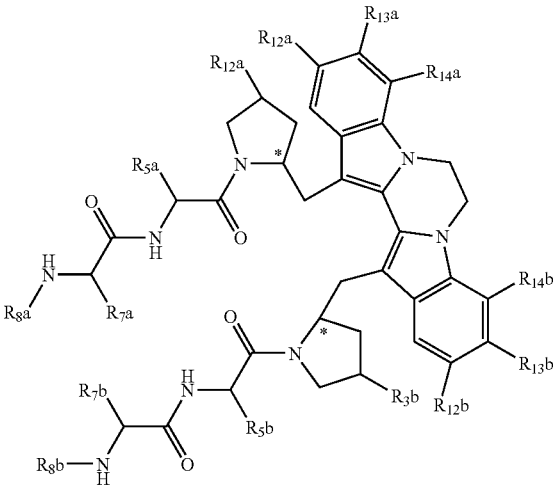

Example 4

Wherein R7a and R7b are independently H, alkyl, cycloalkyl, haloalkyl; or R8a and R7a and R8b and R7b can independently or together form a ring such as an aziridine or azetidine ring;

R8a and R8b are independently H, hydroxyl, alkyl, aryl, arylalkyl, cycloalkyl, cycloalkylalkyl, heteroaryl, or heteroarylalkyl wherein each alkyl, aryl, arylalkyl, cycloalkyl, cycloalkylalkyl, heteroaryl, and heteroarylalkyl is optionally-substituted with halogen, hydroxyl, mercapto, carboxyl, alkyl, alkoxy, amino, and nitro; or R8a and R7a and R8b and R7b can independently or together form a ring such as an aziridine or azetidine ring;

R5a and R5b are independently H, alkyl, cycloalkyl, cycloalkylalkyl, heterocycloalkyl, aryl, arylalkyl, heteroaryl, heteroarylalkyl; or each optionally-substituted with hydroxyl, mercapto, halogen, amino, carboxyl, alkyl, haloalkyl, alkoxy, or alkylthio; or, optionally, R5a and R5b are connected by an alkylene, alkenylene, alkynylene of 2 to 12 carbon atoms or optionally-substituted alkylene, alkenylene, alkynylene bridge of 2 to 12 carbon atoms where one or more carbon atoms can be replaced with N, O, or S;

R12a, R12b, R13a, R13b, R14a, and R14b are independently H, Cl, Br, F, alkyl, cycloalkyl, hydroxy, alkoxy, amino, alkylamino, cyano, or CO$_2$H; and R3a and R3b are independently H, halogen, alkyl, aryl, arylalkyl, amino, arylamino, arylalkylamino, hydroxy, alkyloxy, aryloxy, arylalkylhydroxy, dialkylamino, amido, sulfonamido, or amidino.

| Entry | R8a | R7a | R5a | Stereochem at Position (*) | R3a | R3b | R5b | R7b | R8b | R12 | R13 | R14 | $K_D$ Range |
|---|---|---|---|---|---|---|---|---|---|---|---|---|---|
| 72 | Me | S-Me | S-(2R-EtOH) | S | H | H | S-(2R-EtOH) | S-Me | Me | H | F | H | A |
| 73 | Me | S-Me | S-iPr | S | H | H | S-iPr | S-Me | Me | H | F | H | A |
| 74 | H | S-Me | S-iPr | S | H | H | S-iPr | S-Me | Me | H | F | H | A |
| 75 | Me | S-Me | S-iPr | S | H | H | S-iPr | S-Me | Me | F | H | H | A |
| 76 | Me | S-Me | H | S | H | H | H | S-Me | Me | H | F | H | B |
| 77 | Me | S-Me | S-Me | S | H | H | S-Me | S-Me | Me | H | F | H | B |
| 78 | Me | S-Me | S-(2S-EtOH) | S | H | H | S-(2S-EtOH) | S-Me | Me | H | F | H | A |
| 79 | Me | S-Me | S-Et | S | H | H | S-Et | S-Me | Me | H | F | H | A |
| 80 | Me | S-Me | S-(2S-EtOH) | S | H | H | S-(2S-EtOH) | S-Me | Me | F | H | H | A |
| 81 | H | H | S-iPr | S | H | H | S-iPr | H | H | H | F | H | B |
| 82 | Me | S-Me | S-sBu | S | H | H | S-sBu | S-Me | Me | F | H | H | A |
| 83 | Me | S-Me | S-cHex | S | H | H | S-cHex | S-Me | Me | F | H | H | A |
| 84 | Me | S-Me | S-tBu | S | H | H | S-tBu | S-Me | Me | H | F | H | A |
| 85 | Me | S-Me | S-cHex | S | H | H | S-cHex | S-Me | Me | H | F | H | A |
| 86 | Me | S-Me | S-(2R-EtOH) | R | S—OH | S—OH | S-(2R-EtOH) | S-Me | Me | H | F | H | A |
| 87 | Me | S-Me | S-iPr | R | S—OH | S—OH | S-iPr | S-Me | Me | H | F | H | A |
| 88 | Me | S-Me | S-(2R-EtOMe) | R | S—OH | S—OH | S-(2R-EtOMe) | S-Me | Me | H | F | H | A |
| 89 | Me | S-Me | S-(2R-EtOtBu) | R | S—OH | S—OH | S-(2R-EtOtBu) | S-Me | Me | H | F | H | B |
| 90 | Me | S-Me | S-(2S-EtOH) | R | S—OH | S—OH | S-(2S-EtOH) | S-Me | Me | H | F | H | A |
| 91 | Me | R-Me | S-iPr | S | H | H | S-iPr | R-Me | Me | H | F | H | B |
| 92 | Me | S-Me | R-iPr | S | H | H | R-iPr | S-Me | Me | H | F | H | C |
| 93 | Me | R-Me | R-iPr | S | H | H | R-iPr | R-Me | Me | H | F | H | C |

Further Examples

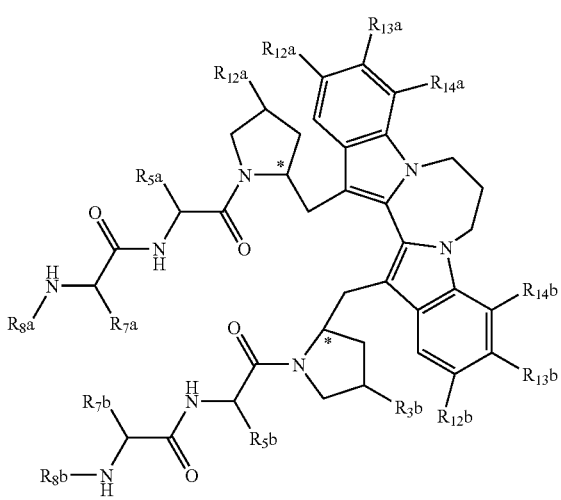

Example 5

Wherein R7a and R7b are independently H, alkyl, cycloalkyl, haloalkyl; or R8a and R7a and R8b and R7b can independently or together form a ring such as an aziridine or azetidine ring;

R8a and R8b are independently H, hydroxyl, alkyl, aryl, arylalkyl, cycloalkyl, cycloalkylalkyl, heteroaryl, or heteroarylalkyl wherein each alkyl, aryl, arylalkyl, cycloalkyl, cycloalkylalkyl, heteroaryl, and heteroarylalkyl is optionally-substituted with halogen, hydroxyl, mercapto, carboxyl, alkyl, alkoxy, amino, and nitro; or R8a and R7a and R8b and R7b can independently or together form a ring such as an aziridine or azetidine ring;

R5a and R5b are independently H, alkyl, cycloalkyl, cycloalkylalkyl, heterocycloalkyl, aryl, arylalkyl, heteroaryl, heteroarylalkyl; or each optionally-substituted with hydroxyl, mercapto, halogen, amino, carboxyl, alkyl, haloalkyl, alkoxy, or alkylthio; or, optionally, R5a and R5b are connected by an alkylene, alkenylene, alkynylene of 2 to 12 carbon atoms or optionally-substituted alkylene, alkenylene, alkynylene bridge of 2 to 12 carbon atoms where one or more carbon atoms can be replaced with N, O, or S;

R12a, R12b, R13a, R13b, R14a, and R14b are independently H, Cl, Br, F, alkyl, cycloalkyl, hydroxy, alkoxy, amino, alkylamino, cyano, or $CO_2H$; and R3a and R3b are independently H, halogen, alkyl, aryl, arylalkyl, amino, arylamino, arylalkylamino, hydroxy, alkyloxy, aryloxy, arylalkylhydroxy, dialkylamino, amido, sulfonamido, or amidino.

| Entry | R8a | R7a | R5a | Stereochem at Position (*) | R3a | R3b | R5b | R7b | R8b | R12 | R13 | R14 | $K_D$ Range |
|---|---|---|---|---|---|---|---|---|---|---|---|---|---|
| 94 | Me | S-Me | S-(2R-EtOH) | S | H | H | S-(2R-EtOH) | S-Me | Me | H | H | H | A |

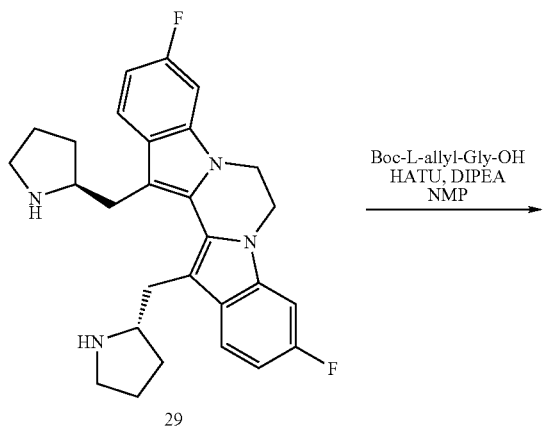

Scheme XIV

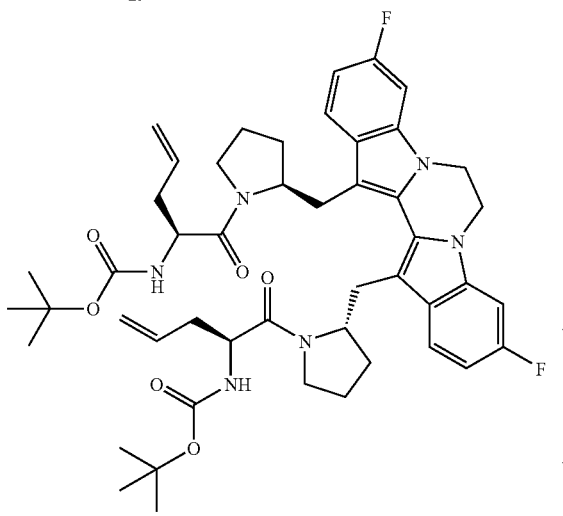

34

Bis-(Boc-Allylglycine)-Containing Species (34)

A solution containing Boc-L-allyl-Gly-OH (0.115 g, 0.53 mmol) and HATU (0.20 g, 0.53 mmol) in anhydrous NMP (3 mL) was cooled to 0° C. After 10 min, diisopropylethylamine (0.1 mL, 0.58 mmol) was added via syringe. After 5 min, a solution containing 29 (0.11 g, 0.23 mmol) in NMP (3 mL) was added and the reaction mixture was allowed to warm to ambient temperature over 16 h at which point TLC analysis revealed complete consumption of 29 [TLC analysis, 5% MeOH/DCM, $R_f(29)$=0.4]. The reaction mixture was diluted with diethyl ether and washed once with saturated aqueous NaHCO$_3$, once with dilute aqueous HCl, and twice with brine, dried over anhydrous Na$_2$SO$_4$, filtered, and concentrated. The crude product was purified by RP-HPLC (Dynamax Microsorb C18 60 Å8μ, 41.4 mm×250 mm; Flow 40 mL/min; Detector: 254 nm, 20-100% gradient of ACN/water with 0.1% AcOH over 30 min). The product-containing fractions were diluted with EtOAc, washed with saturated aqueous NaHCO$_3$, dried over anhydrous Na$_2$SO$_4$, filtered, and concentrated to afford 0.067 g (73%) of 34 as a light yellow solid. $^1$H NMR (CDCl$_3$, 300 MHz) δ8.06 (dd, J=5.4, 8.7 Hz, 1H), 7.02-6.92 (m, 2H), 5.88-5.79 (m, 1H), 5.42 (d, J=8.4 Hz, 1H), 5.19-5.11 (m, 2H), 4.49 (dd, J=6.9, 15.9 Hz, 2H), 4.16-4.08 (m, 1H), 3.65-3.41 (m, 3H), 2.75 (app t, J=12.9 Hz, 1H), 2.54-2.35 (m, 2H), 1.75-1.68 (m, 3H), 1.46-1.43 (m, 9H), 1.21-1.19 (m, 1H) ppm. Mass spectrum, m/z=877.7 (M+Na)+.

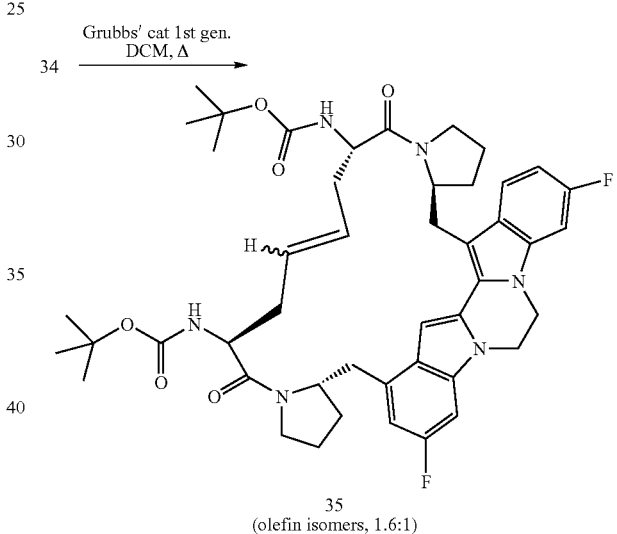

Scheme XV 35
(olefin isomers, 1.6:1)

Ring Closing Metathesis (RCM) Product (35)

To a solution of 34 (0.067 g, 0.08 mmol) in anhydrous DCM (30 mL) was added the first generation Grubbs' catalyst (9.2 mg, 0.01 mmol, 12 mol %) at room temperature. The reaction mixture was heated under reflux for 6 h at which time TLC analysis revealed mostly starting material. Additional Grubbs' catalyst (7 mg, 0.009 mmol, 11 mol %) was then added to the reaction mixture. After 2 d, the solvent was evaporated and the crude residue was purified by NP—HPLC (SiO$_2$, 20% hexane/EtOAc to 100% EtOAc over 20 min) to afford the desired olefins 35 (olefin isomers: 15 mg and 24 mg) as a separable mixture of isomers (unassigned olefin geometry) as light yellow solids. [TLC analysis, 1:1 hexane/EtOAc, $R_f(34)$=0.7; $R_f(35)$=0.6]. 35 Isomer A: $^1$H NMR (CDCl$_3$, 300 MHz) δ7.80 (app t, J=9.0 Hz, 1H), 7.00 (dd, J=1.5, 11.07 Hz, 1H), 6.92 (ddd, J=2.1, 9.3, 11.2 Hz, 1H), 5.62 (app d, J=7.8 Hz, 1H), 5.56 (br s, 1H), 4.79 (m, 1H), 4.56-4.47 (m, 2H), 4.12 (app d, J=6.9 Hz, 1H), 3.85 (dd, J=3.6, 13.5 Hz, 1H), 3.52-3.49 (m, 1H), 3.41 (m, 1H), 2.73

(m, 1H), 2.45-2.40 (m, 2H), 1.70-1.64 (m, 4H), 1.44 (s, 9H), 1.07-1.05 (m, 1H) ppm. Mass spectrum, m/z=849.7 (M+Na)+. 35 Isomer B: $^1$H NMR (CDCl$_3$, 300 MHz) δ7.85 (br s, 1H), 7.0 (dd, J=1.5, 9.3 Hz, 1H), 6.92 (ddd, J=2.4, 9.3, 11.1 Hz, 1H), 5.66 (br s, 1H), 5.56 (app d, J=7.5 Hz, 1H), 4.80 (br s, 1H), 4.62-4.51 (m, 2H), 4.17-4.09 (m, 1H), 3.75-3.52 (m, 3H), 2.69-2.60 (m, 2H), 2.47 (app d, J=15.3 Hz, 1H), 1.69 (m, 3H), 1.45 (s, 9H), 1.18 (m, 1H) ppm. Mass spectrum, m/z=849.7 (M+Na)+.

Scheme XVI

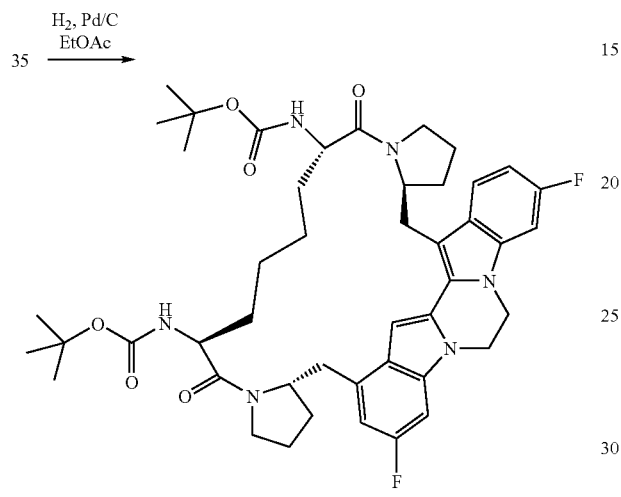

Alkyl-linked Product (36)

To a solution of olefin 35 Isomer A (15 mg, 0.02 mmol) in EtOAc (5 mL) was added 5% Pd/C (25 mg). The reaction mixture was shaken under a H$_2$ atmosphere using a Parr apparatus (~45-50 PSI). After 2.5 h, TLC analysis revealed unreacted starting material. Additional 5% Pd/C (20 mg) was then added and the mixture was again subjected to hydrogenation using a Parr apparatus. After 1.5 h, the mixture was filtered through Celite®, and the solids were rinsed with EtOAc. The filtrate was concentrated in vacuo to give 36 as a light yellow solid.

35 Isomer B (24 mg, 0.03 mmol) was subjected to the same reaction conditions and workup procedures as described for Isomer A. The product (36) was combined with that from the hydrogenation of Isomer A. Compound 36 was isolated as a light yellow solid (35 mg, 85%). [TLC analysis, 1:1 hexane/EtOAc, R$_f$(36)=0.3]. $^1$H NMR (CDCl$_3$, 300 MHz) δ7.85 (dd, J=5.4, 8.1 Hz, 1H), 7.00 (dd, J=1.8, 9.9 Hz, 1H), 6.92 (ddd, J=2.4, 9.2, 11.1 Hz, 1H), 5.70 (d, J=7.8 Hz, 1H), 4.79-4.78 (m, 1H), 4.57-4.51 (m, 2H), 4.13-4.09 (m, 1H), 3.75 (dd, J=3.6, 12.9 Hz, 1H), 3.53-3.41 (m, 2H), 2.49 (app t, J=12.3 Hz, 1H), 1.68-1.62 (m, 3H), 1.46 (s, 9H), 1.08-1.02 (m, 1H), 0.93-0.89 (m, 1H) ppm. Mass spectrum, m/z=851.7 (M+Na)+.

Scheme XVII

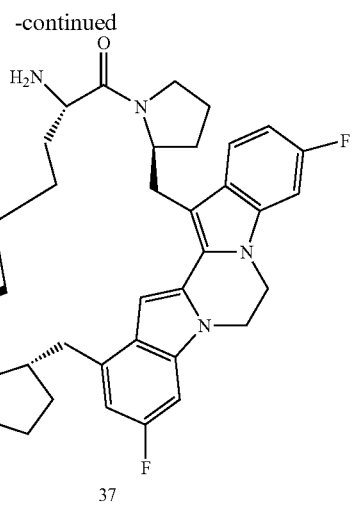

Free Alkyl-linked Diamine (37)

A solution containing 36 (0.035 g, 0.04 mmol) in DCM (10 mL) was cooled to 0° C. TFA (1 mL) was added via pipette and the reaction was allowed to warm to ambient temperature and monitored until TLC analysis revealed complete consumption of 36 (~1 h). The solvent was removed on a rotary evaporator and the residue was dissolved in EtOAc. The EtOAc solution was washed twice with saturated aqueous NaHCO$_3$ and once with brine. The combined aqueous washes were back-extracted with EtOAc and the organic extracts were dried over anhydrous Na$_2$SO$_4$, filtered, and concentrated to afford 0.025 g (quant.) of 37 as a yellow solid which was used without further purification. $^1$H NMR (CDCl$_3$, 300 MHz) δ7.92-7.87 (m, 1H), 7.00 (dd, J=2.1, 9.9 Hz, 1H), 6.91 (ddd, J=2.4, 9.3, 11.1 Hz, 1H), 4.81 (m, 1H), 4.52 (d, J=8.1 Hz, 1H), 4.13-4.09 (m, 1H), 3.79-3.76 (m, 2H), 3.42-3.39 (m, 2H), 2.50 (app t, J=12.9 Hz, 1H), 1.89 (m, 4H), 1.65-1.61 (m, 3H), 1.33-1.24 (m, 4H), 1.09-1.03 (m, 1H), 0.94-0.82 (m, 1H) ppm. Mass spectrum, m/z=315.3 (M+H)+/2; m/z=629.5 (M+H)+.

Scheme XVIII

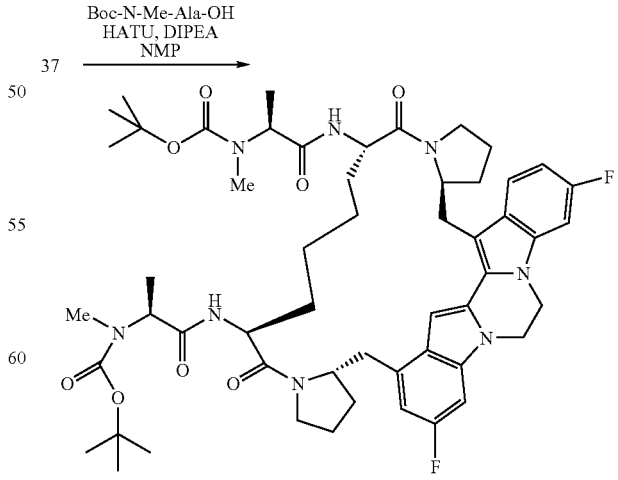

Bis-[Boc-N(Me)-Alanine]-containing Macrocycle (38)

A solution containing Boc-N-methyl-L-Ala-OH (0.022 g, 0.11 mmol) and HATU (0.03 g, 0.09 mmol) in anhydrous NMP (4 mL) was cooled to 0° C. After 10 min, diisopropylethylamine (0.05 mL, 0.29 mmol) was added via syringe. After 5 min, a solution containing 37 (0.025 g, 0.04 mmol) in NMP (3 mL) was added and the reaction mixture was allowed to warm to ambient temperature over 24 h at which point TLC analysis revealed complete consumption of 37 [TLC analysis, 5% MeOH/DCM, $R_f(38)$=0.3]. The reaction mixture was diluted with diethyl ether and washed once with saturated aqueous $NaHCO_3$, once with dilute aqueous HCl, and twice with brine, dried over anhydrous $Na_2SO_4$, filtered, and concentrated to give 38 as a yellow oil (35 mg) which was used without further purification.

Scheme XIX

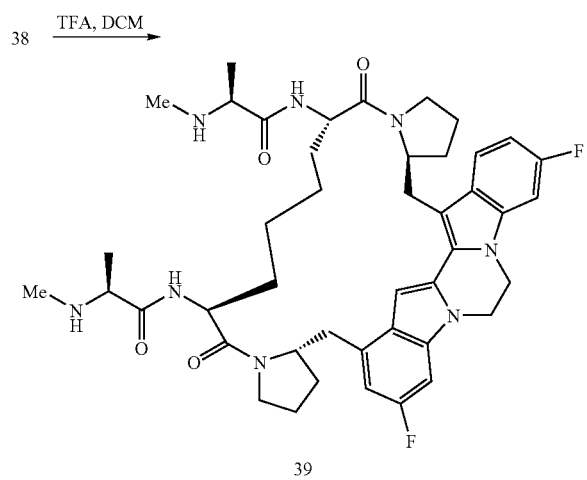

Macrocyclic Smac Mimetic (39)

A solution containing 38 (0.035 g, 0.04 mmol) in DCM (10 mL) was cooled to 0° C. TFA (1 mL) was added via pipette and the reaction was allowed to warm to ambient temperature and monitored until TLC analysis revealed complete consumption of 38 (~2 h). The solvent was removed on a rotary evaporator and the residue was dissolved in EtOAc. The EtOAc solution was washed twice with saturated aqueous $NaHCO_3$ and once with brine. The combined aqueous washes were back-extracted with EtOAc and the organic extracts were dried over anhydrous $Na_2SO_4$, filtered, and concentrated to afford 39 as a yellow solid. The crude product was purified by RP-HPLC (Dynamax Microsorb C18 60 Å 8µ, 41.4 mm×250 mm; Flow 40 mL/min; Detector 254 nm, 20-100% gradient of ACN/water with 0.1% AcOH over 30 min). The product-containing fractions were diluted with EtOAc and washed with saturated aqueous $NaHCO_3$, dried over anhydrous $Na_2SO_4$, filtered, and concentrated. The material was dissolved in a minimum amount of ACN, diluted with water, frozen, and lyophilized to afford 39 as a white flocculent solid (0.002 g). $^1H$ NMR ($CDCl_3$, 300 MHz) δ8.16 (app d, J=8.1 Hz, 1H), 7.90-7.86 (m, 1H), 7.00 (app d, J=8.7 Hz, 1H), 6.93 (ddd, J=3.0, 7.5, 9.0 Hz, 1H), 4.80 (m, 2H), 4.52 (d, J=8.4 Hz, 1H), 4.11 (d, J=8.4 Hz, 1H), 3.79 (dd, J=3.9, 12.9 Hz, 1H), 3.51 (m, 1H), 3.44 (m, 1H), 3.11-3.09 (m, 1H), 2.46 (s, 3H), 1.35-1.25 (m, 8H), 1.06 (m, 1H), 0.89-0.85 (m, 1H) ppm. Mass spectrum, m/z=400.5 (M)+/2; m/z=799.7 (M)+; m/z=821.7 (M+Na+).

Examples

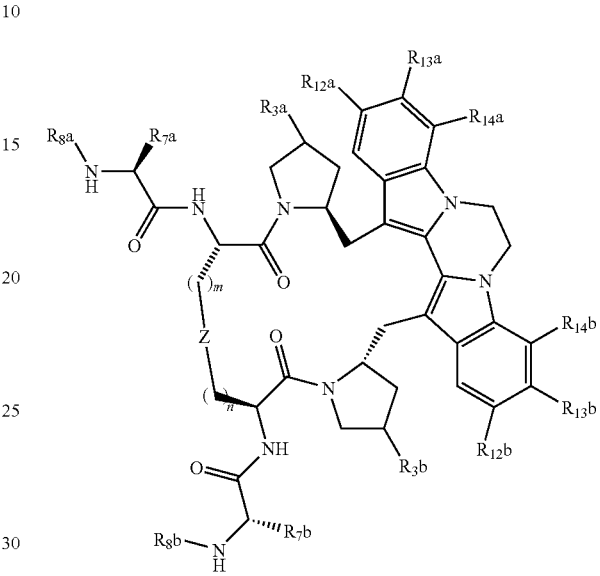

Example 6

Wherein R7a and R7b are independently H, alkyl, cycloalkyl, haloalkyl; or R8a and R7a and R8b and R7b can independently or together form a ring such as an aziridine or azetidine ring;

R8a and R8b are independently H, hydroxyl, alkyl, aryl, arylalkyl, cycloalkyl, cycloalkylalkyl, heteroaryl, or heteroarylalkyl wherein each alkyl, aryl, arylalkyl, cycloalkyl, cycloalkylalkyl, heteroaryl, and heteroarylalkyl is optionally-substituted with halogen, hydroxyl, mercapto, carboxyl, alkyl, alkoxy, amino, and nitro; or R8a and R7a and R8b and R7b can independently or together form a ring such as an aziridine or azetidine ring;

Z is a bond; an alkylene, alkenylene, alkynylene group of 1 to 6 atoms; or, an optionally substituted alkylene, alkenylene, or alkynylene group of 1 to 6 carbon atoms; a sulfide (—S—), sulfoxide (—SO—), sulfone (—$SO_2$—), or disulfide (—SS—) group; an aryl, arylalkylene, heteroaryl, heteroarylalkylene, or an optionally substituted aryl, arylalkylene, heteroaryl, heteroarylalkylene group; an amino or substituted amino group; an oxygen atom;

m and n are independently 0, 1, 2, or 3;

R12a, R12b, R13a, R13b, R14a, and R14b are independently H, Cl, Br, F, alkyl, cycloalkyl, hydroxyl, alkoxy, amino, alkylamino, cyano, or $CO_2H$; and R3a and R3b are independently H, halogen, alkyl, aryl, arylalkyl, amino, arylamino, arylalkylamino, hydroxy, alkyloxy, aryloxy, arylalkylhydroxy, dialkylamino, amido, sulfonamido, or amidino.

| Entry | R8a | R7a | m | n | Z | R3a | R3b | R7b | R8b | R12 | R13 | R14 | $K_D$ Range, μM |
|---|---|---|---|---|---|---|---|---|---|---|---|---|---|
| 95 | Me | Me | 1 | 1 | Z—CH=CH— | H | H | Me | Me | H | F | H | A |
| 96 | Me | Me | 1 | 1 | E—CH=CH— | H | H | Me | Me | H | F | H | A |
| 97 | Me | Me | 1 | 1 | —CH$_2$CH$_2$— | H | H | Me | Me | F | H | H | A |
| 98 | Me | Me | 1 | 1 | —CH$_2$CH$_2$— | H | H | Me | Me | H | F | H | A |
| 99 | H | Me | 1 | 1 | —SS— | H | H | Me | H | H | F | H | A |
| 100 | Me | Me | 1 | 1 | —CH(OH)CH(OH)— | H | H | Me | Me | H | H | H | A |
| 101 | Me | Me | 1 | 1 | —CH$_2$CH$_2$— | S—OH | S—OH | Me | Me | H | F | H | A |

Further Examples

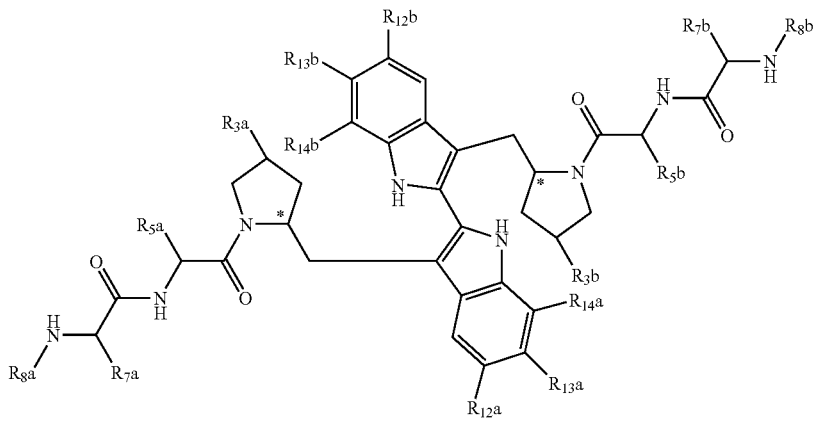

Example 7

Wherein R7a and R7b are independently H, alkyl, cycloalkyl, haloalkyl; or R8a and R7a and R8b and R7b can independently or together form a ring such as an aziridine or azetidine ring;

R8a and R8b are independently H, hydroxyl, alkyl, aryl, arylalkyl, cycloalkyl, cycloalkylalkyl, heteroaryl, or heteroarylalkyl wherein each alkyl, aryl, arylalkyl, cycloalkyl, cycloalkylalkyl, heteroaryl, and heteroarylalkyl is optionally-substituted with halogen, hydroxyl, mercapto, carboxyl, alkyl, alkoxy, amino, and nitro; or R8a and R7a and R8b and R7b can independently or together form a ring such as an aziridine or azetidine ring;

R5a and R5b are independently H, alkyl, cycloalkyl, cycloalkylalkyl, heterocycloalkyl, aryl, arylalkyl, heteroaryl, heteroarylalkyl; or each optionally-substituted with hydroxyl, mercapto, halogen, amino, carboxyl, alkyl, haloalkyl, alkoxy, or alkylthio; or, optionally, R5a and R5b are connected by an alkylene, alkenylene, alkynylene of 2 to 12 carbon atoms or optionally-substituted alkylene, alkenylene, alkynylene bridge of 2 to 12 carbon atoms where one or more carbon atoms can be replaced with N, O, or S;

R12a, R12b, R13a, R13b, R14a, and R14b are independently H, Cl, Br, F, alkyl, cycloalkyl, hydroxy, alkoxy, amino, alkylamino, cyano, or CO$_2$H; and R3a and R3b are independently H, halogen, alkyl, aryl, arylalkyl, amino, arylamino, arylalkylamino, hydroxy, alkyloxy, aryloxy, arylalkylhydroxy, dialkylamino, amido, sulfonamido, or amidino.

| Entry | R8a | R7a | R5a | Stereochem at Position (*) | R3a | R3b | R5b | R7b | R8b | R12 | R13 | R14 | $K_D$ Range |
|---|---|---|---|---|---|---|---|---|---|---|---|---|---|
| 102 | H | S-Me | S-iPr | S | H | H | S-iPr | S-Me | Me | H | F | H | A |
| 103 | Me | S-Me | S-(2R-EtOH) | S | H | H | S-(2R-EtOH) | S-Me | Me | H | F | H | A |
| 104 | H | S-Me | S-iPr | S | H | H | S-iPr | S-Me | Me | H | H | H | A |
| 105 | Me | S-Me | S-(2R-EtOH) | S | H | H | S-(2R-EtOH) | S-Me | Me | H | H | H | A |
| 106 | H | S-Me | S-(2R-EtOH) | S | H | H | S-(2R-EtOH) | S-Me | H | H | H | H | A |
| 107 | Me | S-Me | S-iPr | S | H | H | S-iPr | S-Me | Me | H | H | H | A |
| 108 | H | S-Et | S-iPr | S | H | H | S-iPr | S-Et | H | H | H | H | A |
| 109 | Me | S-Et | S-iPr | S | H | H | S-iPr | S-Et | Me | H | H | H | A |
| 110 | Me | S-Me | S-(2S-EtOH) | S | H | H | S-(2S-EtOH) | S-Me | Me | H | F | H | A |

-continued

| Entry | R8a | R7a | R5a | Stereochem at Position (*) | R3a | R3b | R5b | R7b | R8b | R12 | R13 | R14 | $K_D$ Range |
|---|---|---|---|---|---|---|---|---|---|---|---|---|---|
| 111 | Me | S-Me | S-Allyl | S | H | H | S-Allyl | S-Me | Me | H | F | H | A |
| 112 | Me | S-Me | S-iPr | R | S—OH | S—OH | S-iPr | S-Me | Me | H | F | H | A |
| 113 | Me | S-Me | S-sBu | R | S—OH | S—OH | S-sBu | S-Me | Me | H | F | H | A |
| 114 | Me | S-Me | S-(2S-EtOtBu) | R | S—OH | S—OH | S-(2S-EtOtBu) | S-Me | Me | H | F | H | A |
| 115 | Me | S-Me | S-(2S-EtOH) | R | S—OH | S—OH | S-(2S-EtOH) | S-Me | Me | H | F | H | A |
| 116 | Me | S-Me | S-(2R-EtOMe) | R | S—OH | S—OH | S-(2R-EtOMe) | S-Me | Me | H | F | H | A |
| 117 | Me | S-Me | S-(2S-EtOMe) | R | S—OH | S—OH | S-(2S-EtOMe) | S-Me | Me | H | F | H | A |
| 118 | Me | S-Me | S-(2R-EtOH) | R | S—OH | S—OH | S-(2R-EtOH) | S-Me | Me | H | F | H | A |

Scheme XX

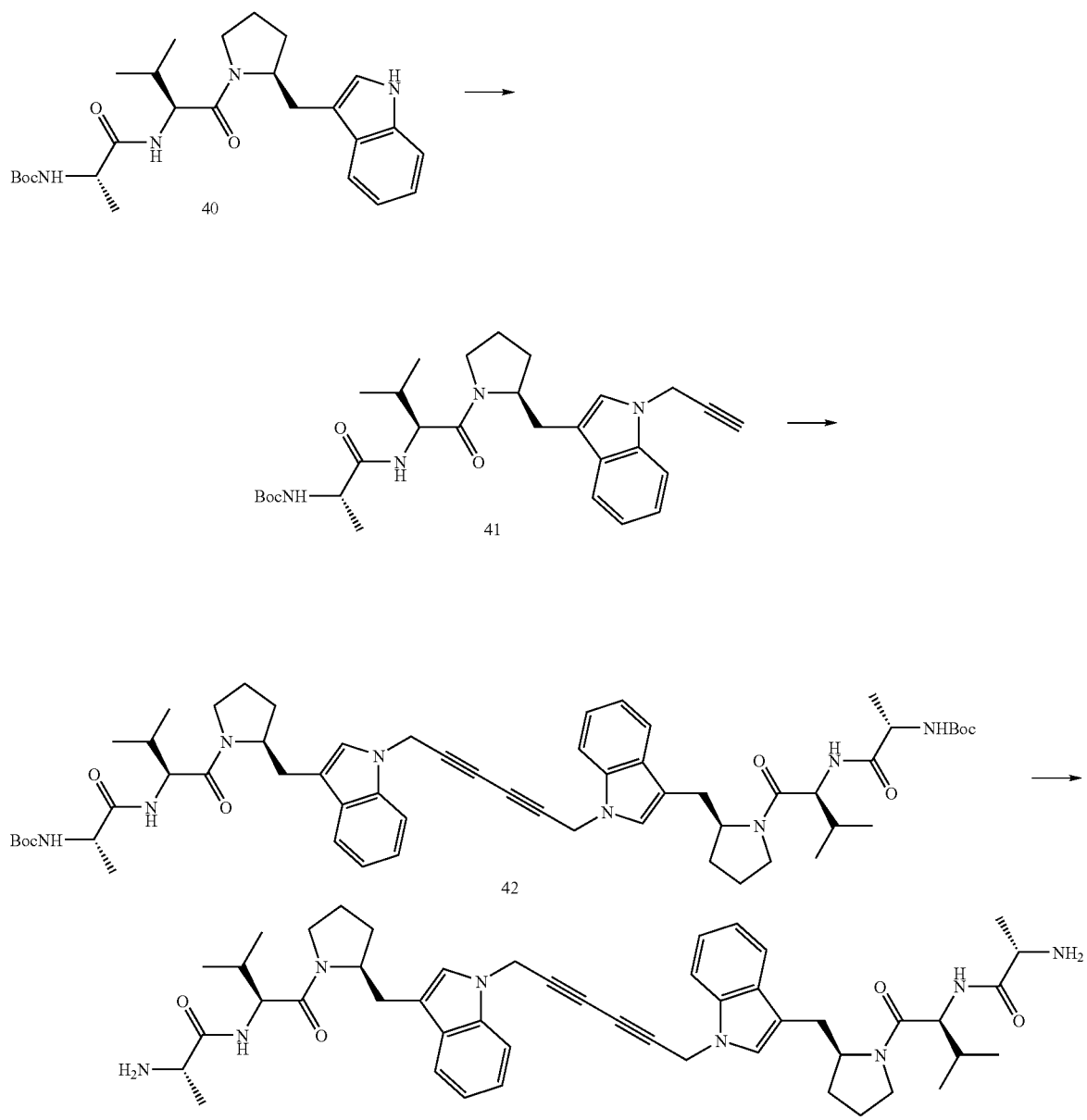

Preparation of 2-Amino-N-[1-(2-{1-[6-(3-{1-[2-(2-amino-propionylamino)-3-methyl-butyryl]-pyrrolidin-2-ylmethyl}-indol-1-yl)-hexa-2,4-diynyl]-1H-indol-3-ylmethyl}-pyrrolidine-1-carbonyl)-2-methyl-propyl]-propionamide (43)

A. (1S-{2-Methyl-1S-[2S-(1-prop-2-ynyl-1H-indol-3-ylmethyl)-pyrrolidine-1-carbonyl]-propylcarbamoyl}-ethyl)-carbamic acid tert-butyl ester (41)

To a solution of 40 (0.150 g, 0.319 mmol) in THF (2 mL) was added propargyl bromide [0.06 mL, 0.410 mmol, (80% wt/toluene)] followed by NaH [0.015 g, 0.410 mmol, (60% dispersion in mineral oil)]. The reaction mixture was stirred overnight at room temperature. Water (2 mL) was added to the reaction mixture and the product was extracted with ethyl acetate (3×30 mL). The ethyl acetate extracts were washed with water, brine and dried over anhydrous $Na_2SO_4$, filtered, and concentrated. The crude product was purified by HPLC. $^1$H NMR (CDCl$_3$, 300 MHz): δ8.0 (s, 1H), 7.9 (d, J=9.9 Hz, 1H), 7.38 (d, J=9.9 Hz, 1H), 7.3-7.1 (m, 3H), 6.8 (m, 1H), 4.8 (s, 2H), 4.62 (m 1H), 4.5-4.4 (m 1H), 4.4-4.0 (m, 2H), 3.7-3.5 (m, 2H), 3.4 (m, 1H), 2.5 (m, 1H), 2.4 (s, 1H), 2.2-1.8 (m, 4H), 1.48 (s, 9H), 1.35 (d, J=9.9 Hz, 3H), 1.05 (d, J=5.5 Hz, 3H), 0.95 (d, J=5.5 Hz, 3H) ppm.

B. {1-[1-(2-{1-[6-(3-{1-[2-(2-tert-Butoxycarbonylamino-propionylamino)-3-methyl-butyryl]-pyrrolidin-2-ylmethyl}-indol-1-yl)-hexa-2,4-diynyl]-1H-indol-3-ylmethyl}-pyrrolidine-1-carbonyl)-2-methyl-propylcarbamoyl]-ethyl}-carbamic acid tert-butyl ester (42)

To a solution of 41 (0.040 g, 0.077 mmol) in acetonitrile (2 mL), was added copper (II) acetate (0.070 g, 0.385 mmol) and the reaction mixture was immersed in a preheated oil bath (~100° C.) and refluxed for 5 min. Water was then added to the reaction mixture (2 mL) and the product was extracted with EtOAc (3×30 mL). The organic extracts were washed with aqueous NH$_4$OH (5 mL), water, brine and dried over anhydrous Na$_2$SO$_4$, filtered, and concentrated to afford the crude product. $^1$H NMR (CDCl$_3$, 300 MHz): δ8.0 (s, 2H), 7.9 (d, J=9.9 Hz, 2H), 7.38 (d, J=9.9 Hz, 2H), 7.3-7.1 (m, 6H), 6.8 (m, 2H), 4.8 (s, 4H), 4.62 (m 2H), 4.5-4.4 (m 2H), 4.4-4.0 (m, 4H), 3.7-3.5 (m, 4H), 3.4 (m, 2H), 2.5 (m, 2H), 2.2-1.8 (m, 8H), 1.48 (s, 18H), 1.35 (d, J=9.9H, 6H), 1.05 (d, J=5.5 Hz, 6H), 0.95 (d, J=5.5 Hz, 6H) ppm.

C. 2-Amino-N-[1-(2-{1-[6-(3-{1-2-(2-amino-propionylamino)-3-methyl-butyryl]-pyrrolidin-2-ylmethyl}-indol-1-yl)-hexa-2,4-diynyl]-1H-indol-3-ylmethyl}-pyrrolidine-1-carbonyl)-2-methyl-propyl]-propionamide (43)

To a solution of 42 (0.030 g, 0.029 mmol) in DCM (5 mL) was added TFA (1 mL) and the reaction mixture was stirred at room temperature for 30 min. Aqueous NaHCO$_3$ (3 mL) was then added to the reaction mixture. The reaction mixture was concentrated, diluted with water, and the product was extracted with DCM (3×30 mL). The organic extracts were washed with water, brine and dried over anhydrous Na$_2$SO$_4$. The solvent was removed on rotary evaporator and the product was purified by reverse phase HPLC. $^1$H NMR (DMSO, 300 MHz) δ8.0 (s, 2H), 7.9 (d, J=9.9 Hz, 2H), 7.38 (d, J=9.9 Hz, 2H), 7.3-7.1 (m, 6H), 6.8 (m, 2H), 4.8 (s, 4H), 4.62 (m 2H), 4.5-4.4 (m 2H), 4.4-4.0 (m, 4H), 3.7-3.5 (m, 4H), 3.4 (m, 2H), 2.5 (m, 2H), 2.2-1.8 (m, 8H), 1.35 (d, J=9.9 Hz, 6H), 1.05 (d, J=5.5 Hz, 6H), 0.95 (d, J=5.5 Hz, 6H) ppm.

Examples

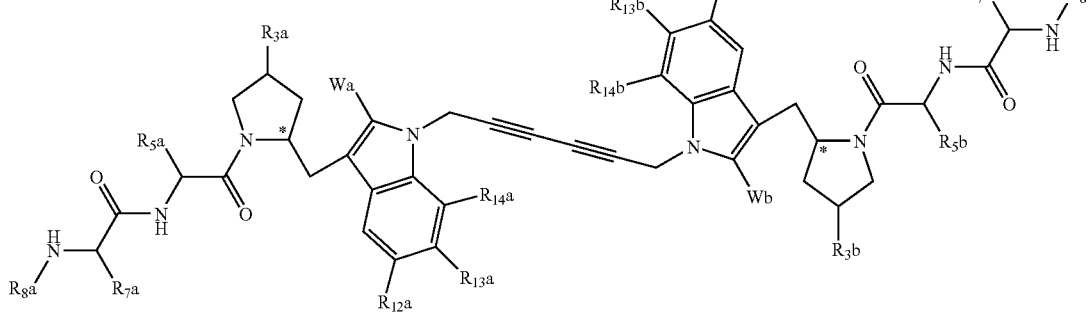

Example 8

Wherein R7a and R7b are independently H, alkyl, cycloalkyl, haloalkyl; or R8a and R7a and R8b and R7b can independently or together form a ring such as an aziridine or azetidine ring;

R8a and R8b are independently H, hydroxyl, alkyl, aryl, arylalkyl, cycloalkyl, cycloalkylalkyl, heteroaryl, or heteroarylalkyl wherein each alkyl, aryl, arylalkyl, cycloalkyl, cycloalkylalkyl, heteroaryl, and heteroarylalkyl is optionally-substituted with halogen, hydroxyl, mercapto, carboxyl, alkyl, alkoxy, amino, and nitro; or R8a and R7a and R8b and R7b can independently or together form a ring such as an aziridine or azetidine ring;

R5a and R5b are independently H, alkyl, cycloalkyl, cycloalkylalkyl, heterocycloalkyl, aryl, arylalkyl, heteroaryl, heteroarylalkyl; or each optionally-substituted with hydroxyl, mercapto, halogen, amino, carboxyl, alkyl, haloalkyl, alkoxy, or alkylthio; or, optionally, R5a and R5b are connected by an alkylene, alkenylene, alkynylene of 2 to 12 carbon atoms or optionally-substituted alkylene, alkenylene, alkynylene bridge of 2 to 12 carbon atoms where one or more carbon atoms can be replaced with N, O, or S;

R12a, R12b, R13a, R13b, R14a, and R14b are independently H, Cl, Br, F, alkyl, cycloalkyl, hydroxy, alkoxy, amino, alkylamino, cyano, or CO$_2$H;

R3a and R3b are independently H, halogen, alkyl, aryl, arylalkyl, amino, arylamino, arylalkylamino, hydroxy, alkyloxy, aryloxy, arylalkylhydroxy, dialkylamino, amido, sulfonamido, or amidino; and Wa and Wb are independently H, Cl, Br, F, alkyl, CN, or CO$_2$H.

| Entry | R8a | R7a | R5a | Stereochem at Position (*) | Wa | Wb | R3a | R3b | R5b | R7b | R8b | R12 | R13 | R14 | $K_D$ Range |
|---|---|---|---|---|---|---|---|---|---|---|---|---|---|---|---|
| 119 | Me | S-Me | S-tBu | S | H | H | H | H | S-tBu | S-Me | Me | H | H | H | A |
| 120 | Me | S-Me | S-cHex | S | H | H | H | H | S-cHex | S-Me | Me | H | H | H | A |
| 121 | Me | S-Me | S-iPr | S | H | H | H | H | S-iPr | S-Me | Me | H | H | H | A |
Scheme XXI
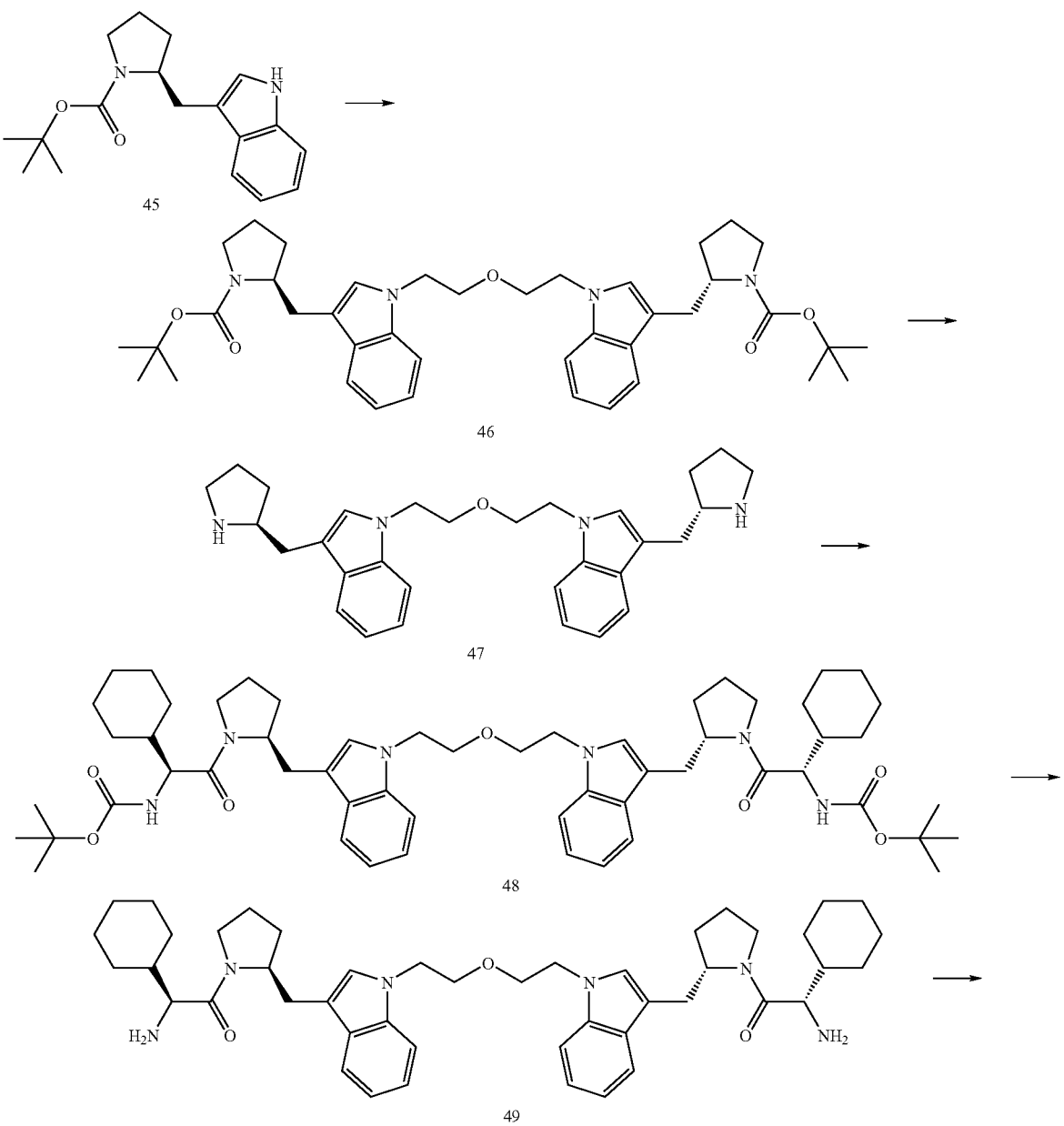

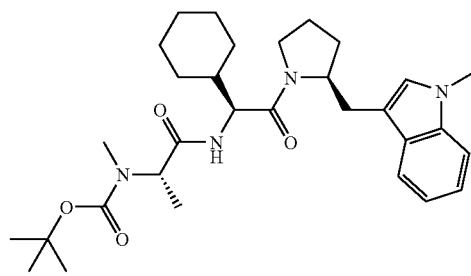
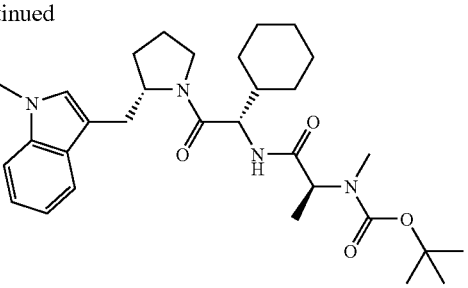

50

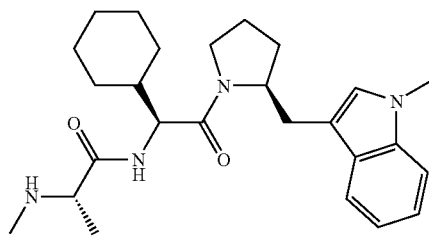
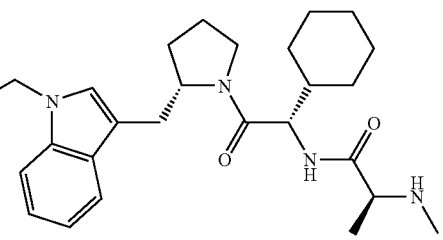

51

Preparation of N-{1-Cyclohexyl-2-[2-(1-{2-[2-(3-{1-[2-cyclohexyl-2-(2-methylamino-propionylamino)-acetyl]-pyrrolidin-2-ylmethyl}-indol-1-yl)-ethoxy]-ethyl}-1H-indol-3-ylmethyl)-pyrrolidin-1-yl]-2-oxo-ethyl}-2-methylamino-propionamide (51)

Compound (46):

At 0° C., NaH (60%, 0.025 g, 0.62 mmol) was added to a solution of indole 45 (0.17 g, 0.56 mmol) in anhydrous DMF (5 mL). After 1 h, bromoethyl ether (0.16 g, 0.68 mmol) and n-Bu$_4$NCl (0.021 g, 0.05 mmol) were added in rapid succession. The reaction mixture was allowed to slowly warm to ambient temperature and stirring was continued for 16 h. The reaction was quenched by the addition of saturated aqueous NH$_4$Cl and the product was extracted with diethyl ether. The combined ether extracts were washed repeatedly with water to remove excess DMF then brine and dried over anhydrous Na$_2$SO$_4$, filtered, and concentrated. The crude product was combined with material formed under similar reaction conditions (0.11 g 45, 0.36 mmol) and purified by normal phase HPLC (10-100% EtOAc/hexane) to afford) 0.18 g of 46 as a colorless oil and 0.18 g of the mono-alkylated indole. $^1$H NMR (CDCl$_3$, 300 MHz) δ7.75-7.66 (m, 2H), 7.25-7.07 (m, 6H), 6.85-6.80 (m, 2H), 4.13 (m, 8H), 3.62 (br s, 4H), 3.40-3.15 (m, 4H), 2.63 (m, 2H), 2.04 (br s, 4H), 1.53 (s, 18H) ppm.

Compound (47):

A solution containing 46 (0.18 g, 0.27 mmol) in DCM (8 mL) was cooled to 0° C. Trifluoroacetic acid (2 mL) was added and the reaction mixture was maintained at 0° C. for 1 h. The reaction was quenched by the careful addition of saturated aqueous NaHCO$_3$ and the product was extracted with EtOAc. The combined organic extracts were washed with aq. NaHCO$_3$, brine, dried over anhydrous Na$_2$SO$_4$, filtered, and concentrated to afford 0.075 g of 47 as a pale yellow oil. The crude product was used directly in the next reaction. $^1$H NMR (CDCl$_3$, 300 MHz) δ8.49 (br s, 2H), 7.57 (app. d, J=8.2, Hz, 2H), 7.26-7.052 (m, 6H), 6.82 (s, 2H), 4.11 (m, 8H), 3.57 (m, 4H), 3.29-2.96 (m, 6H), 1.95-1.58 (m, 8H) ppm.

[2-(2-{1-[2-(2-{3-[1-(2-tert-Butoxycarbonylamino-2-cyclohexyl-acetyl)-pyrrolidin-2-ylmethyl]-indol-1-yl}-ethoxy)-ethyl]-1H-indol-3-ylmethyl}-pyrrolidin-1-yl)-1-cyclohexyl-2-oxo-ethyl]-carbamic acid tent-butyl ester (48)

To a solution containing N-Boc-cyclohexylglycine (0.09 g, 0.34 mmol) in anhydrous NMP (2 mL) was added HATU (0.15 g, 0.38 mmol) and N-methylmorpholine (0.042 g, 0.42 mmol). After 15 min, 47 (0.075 g, 0.16 mmol) in anhydrous NMP (2 mL) was added and the reaction mixture was stirred for 16 h. The reaction mixture was diluted with water and the product was extracted with diethyl ether. The combined ether extracts were washed repeatedly with water to remove excess NMP, brine, dried over anhydrous Na$_2$SO$_4$, filtered, and concentrated. The crude product was purified by normal phase HPLC (50-100% EtOAc/hexane) to afford 0.085 mg of 48 as a colorless oil. $^1$H NMR (CDCl$_3$, 300 MHz) δ7.87 (d, J=7.62 Hz, 2H), 7.27-7.10 (m, 6H), 6.84 (s, 2H), 5.36 (d, J=9.37 Hz, 2H), 4.45 (m, 2H), 4.30 (app. t, J=6.4 Hz, 2H), 4.18-4.12 (m, 6H), 3.70-3.58 (m, 6H), 3.35 (dd, J=14.0, 2.9 Hz, 2H), 2.41 (dt, J=11.1, 2.3 Hz, 2H), 2.04-1.57 (m, 20H), 1.44 (s, 18H), 1.37-1.07 (m, 10H) ppm.

2-Amino-1-(2-{1-[2-(2-{3-[1-(2-amino-2-cyclohexyl-acetyl)-pyrrolidin-2-ylmethyl]-indol-1-yl}-ethoxy)-ethyl]-1H-indol-3-ylmethyl}-pyrrolidin-1-yl)-2-cyclohexyl-ethanone (49)

A solution containing 48 (0.085 g, 0.08 mmol) in DCM (8 mL) was cooled to 0° C. Trifluoroacetic acid (2 mL) was added and the reaction mixture was maintained at 0° C. for 30 min. An additional portion of TFA (1 mL) was added and the reaction mixture was stirred for 1 h at 0° C. The reaction was quenched by the careful addition of saturated aqueous NaHCO$_3$ and the product was extracted with EtOAc. The combined organic extracts were washed with aq. NaHCO$_3$, brine, dried over anhydrous Na$_2$SO$_4$, filtered, and concentrated to afford 0.068 g of 49 as a pale yellow oil. The crude product was used directly in the next reaction. $^1$H NMR (CDCl$_3$, 300 MHz) δ7.90 (d, J=7.6 Hz, 2H), 7.31-7.12 (m, 6H), 6.84 (app t, J=14 Hz, 2H), 4.47 (m, minor rotomer), 4.15 (m, 4H), 3.66-3.36 (m, 8H), 2.80 (m, 2H), 2.42 (m, 2H), 2.04-0.83 (m, 30H) ppm.

Amide (50):

To a solution containing N-Boc-N-methylalanine (0.041 g, 0.19 mmol) in anhydrous NMP (2 mL) was added HATU (0.083 g, 0.21 mmol) and N-methylmorpholine (0.024 g, 0.23 mmol). After 15 min, 49 (0.068 g, 0.09 mmol) in anhydrous NMP (2 mL) was added and the reaction mixture was stirred for 16 h. The reaction mixture was diluted with water and the product was extracted with diethyl ether. The combined ether extracts were washed repeatedly with water to remove excess NMP, brine, dried over anhydrous $Na_2SO_4$, filtered, and concentrated. The crude product was combined with material formed under similar reaction conditions (0.05 g 49, 0.06 mmol) and purified by normal phase HPLC (10-100% EtOAc/hexane) to afford 32 mg of 50 as a colorless oil. $^1$H NMR ($CDCl_3$, 300 MHz) δ7.86 (d, J=7.6 Hz, 2H), 7.27-7.08 (m, 6H), 6.84 (s, 2H), 4.70 (m, 2H), 4.58 (app. t, J=7.6 Hz, 2H), 4.19 (m, 2H), 4.15-4.04 (m, 6H), 3.76-3.60 (m, 6H), 3.37 (m, 2H), 2.83 (s, 6H), 2.42 (m, 2H), 1.98-1.55 (m, 20H), 1.51 (s, 18H), 1.33 (d, J=7.0 Hz, 6H), 1.30-0.98 (m, 10H) ppm.

N-{1-Cyclohexyl-2-[2-(1-{2-[2-(3-{1-2-cyclohexyl-2-(2-methylamino-propionylamino)-acetyl]-pyrrolidin-2-ylmethyl}-indol-1-yl)-ethoxy]-ethyl}-1H-indol-3-ylmethyl)-pyrrolidin-1-yl]-2-oxo-ethyl}-2-methylamino-propionamide (51)

A solution containing 50 (0.0.062 g, 0.055 mmol) in DCM (8 mL) was cooled to 0° C. Trifluoroacetic acid (2 mL) was added and the reaction mixture was maintained at 0° C. for 1 h. The reaction was quenched by the careful addition of saturated aqueous $NaHCO_3$ and the product was extracted with EtOAc. The combined organic extracts were washed with aq. $NaHCO_3$, brine, dried over anhydrous $Na_2SO_4$, filtered, and concentrated. The crude product was purified by reverse phase HPLC (10-100% ACN/water w/0.1% HOAc) to afford 0.047 g of 51.2HOAc as a white solid following lyophilization. $^1$H NMR (DMSO, 300 MHz) δ7.91 (d, J=8.7 Hz, 2H), 7.71 (d, J=7.8 Hz, 2H), 7.32 (d, J=7.5 Hz, 2H), 7.05 (m, 2H), 6.99-6.92 (m, 4H), 4.39 (app. t, J=6.6 Hz, 2H), 4.15 (m, 6H), 3.57 (m, 4H), 3.52-3.23 (m, 4H), 3.06-2.91 (m, 4H), 2.46 (s, 6H), 2.31 (m, 2H), 2.15 (s, 12H), 1.91-1.65 (m, 12H), 1.55-1.49 (m, 8H), 1.07 (d, J=7.0 Hz, 6H), 1.16-0.93 (m, 10H) ppm.

Examples

Example 9

Wherein R7a and R7b are independently H, alkyl, cycloalkyl, haloalkyl; or R8a and R7a and R8b and R7b can independently or together form a ring such as an aziridine or azetidine ring;

R8a and R8b are independently H, hydroxyl, alkyl, aryl, arylalkyl, cycloalkyl, cycloalkylalkyl, heteroaryl, or heteroarylalkyl wherein each alkyl, aryl, arylalkyl, cycloalkyl, cycloalkylalkyl, heteroaryl, and heteroarylalkyl is optionally-substituted with halogen, hydroxyl, mercapto, carboxyl, alkyl, alkoxy, amino, and nitro; or R8a and R7a and R8b and R7b can independently or together form a ring such as an aziridine or azetidine ring;

R5a and R5b are independently H, alkyl, cycloalkyl, cycloalkylalkyl, heterocycloalkyl, aryl, arylalkyl, heteroaryl, heteroarylalkyl; or each optionally-substituted with hydroxyl, mercapto, halogen, amino, carboxyl, alkyl, haloalkyl, alkoxy, or alkylthio; or, optionally, R5a and R5b are connected by an alkylene, alkenylene, alkynylene of 2 to 12 carbon atoms or optionally-substituted alkylene, alkenylene, alkynylene bridge of 2 to 12 carbon atoms where one or more carbon atoms can be replaced with N, O, or S;

R12a, R12b, R13a, R13b, R14a, and R14b are independently H, Cl, Br, F, alkyl, cycloalkyl, hydroxy, alkoxy, amino, alkylamino, cyano, or $CO_2H$;

R3a and R3b are independently H, halogen, alkyl, aryl, arylalkyl, amino, arylamino, arylalkylamino, hydroxy, alkyloxy, aryloxy, arylalkylhydroxy, dialkylamino, amido, sulfonamido, or amidino; and Wa and Wb are independently H, Cl, Br, F, alkyl, CN, $CO_2H$.

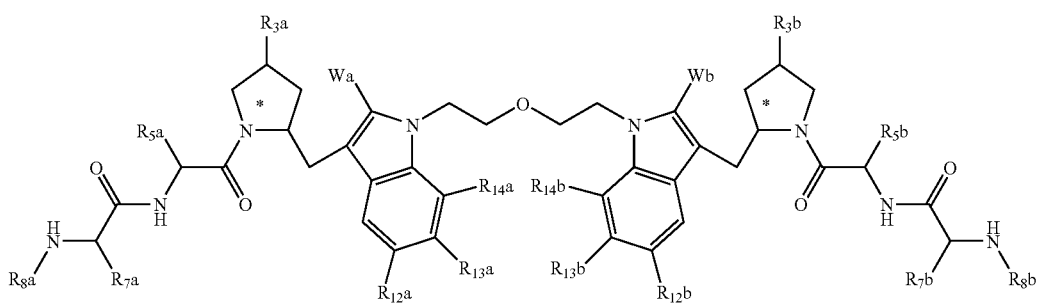

| Entry | R8a | R7a | R5a | Stereochem at Position (*) | Wa | Wb | R3a | R3b | R5b | R7b | R8b | R12 | R13 | R14 | $K_D$ Range, |
|---|---|---|---|---|---|---|---|---|---|---|---|---|---|---|---|
| 122 | Me | S-Me | S-cHex | S | H | H | H | H | S-cHex | S-Me | Me | H | H | H | A |
| 123 | Me | S-Me | S-cHex | S | H | H | H | H | S-cHex | S-Me | Me | H | F | H | A |
| 124 | Me | S-Me | S-(2R-EtOH) | S | H | H | H | H | S-(2R-EtOH) | S-Me | Me | H | F | H | A |
| 125 | Me | S-Et | S-(2R-EtOH) | S | H | H | H | H | S-(2R-EtOH) | S-Et | Me | F | H | H | B |
| 126 | Me | S-Me | S-cHex | S | H | H | H | H | S-cHex | S-Me | Me | F | H | H | A |
| 127 | Me | S-Me | S-cHex | S | Me | Me | H | H | S-cHex | S-Me | Me | F | H | H | A |
| 128 | Me | S-Et | S-cHex | S | Me | Me | H | H | S-cHex | S-Et | Me | F | H | H | A |
| 129 | H | S-Me | S-cHex | S | H | H | H | H | S-cHex | S-Me | H | Cl | H | H | A |
| 130 | Me | S-Me | S-cHex | S | H | H | H | H | S-cHex | S-Me | Me | Cl | H | H | A |
| 131 | H | S-Me | S-iPr | S | H | H | H | H | S-iPr | S-Me | H | Cl | H | H | A |
| 132 | Me | S-Me | S-iPr | S | H | H | H | H | S-iPr | S-Me | Me | Cl | H | H | A |
| 133 | Me | S-Me | S-iPr | S | H | H | H | H | S-iPr | S-Me | Me | F | H | H | A |
| 134 | H | H | S-cHex | S | H | H | H | H | S-cHex | H | H | H | F | H | C |
| 135 | Me | S-Me | H | S | H | H | H | H | H | S-Me | Me | H | F | H | C |
| 136 | Me | S-Et | S-(2R-EtOH) | S | H | H | H | H | S-(2R-EtOH) | S-Et | Me | H | F | H | C |
| 137 | Me | S-Me | S-cHex | S | H | H | H | H | S-cHex | S-Me | Me | Me | H | H | A |
| 138 | H | H | S-cHex | S | H | H | H | H | S-cHex | H | H | H | H | H | B |
| 139 | H | S-Me | S-cHex | S | H | H | H | H | S-cHex | S-Me | H | H | H | H | A |
| 140 | Me | S-Me | S-tBu | S | H | H | H | H | S-tBu | S-Me | Me | H | F | H | A |
| 141 | Me | S-Me | S-tBu | S | H | H | H | H | S-tBu | S-Me | Me | H | H | H | A |
| 142 | H | S-Me | S-tBu | S | H | H | H | H | S-tBu | S-Me | H | H | H | H | A |
| 143 | Me | S-Me | S-cHex | S | H | H | H | H | S-cHex | S-Me | H | H | H | H | A |
| 144 | Me | S-Me | S-cHex | S | H | H | H | H | S-cHex | H | H | H | H | H | A |
| 145 | Me | S-Me | S-(2R-EtOH) | S | H | H | H | H | S-(2R-EtOH) | S-Me | Me | H | H | H | B |
| 146 | Me | S-Me | S—(CH$_2$)$_4$NH$_2$ | S | H | H | H | H | S—(CH$_2$)$_4$NH$_2$ | S-Me | Me | Me | H | H | A |

Other Examples

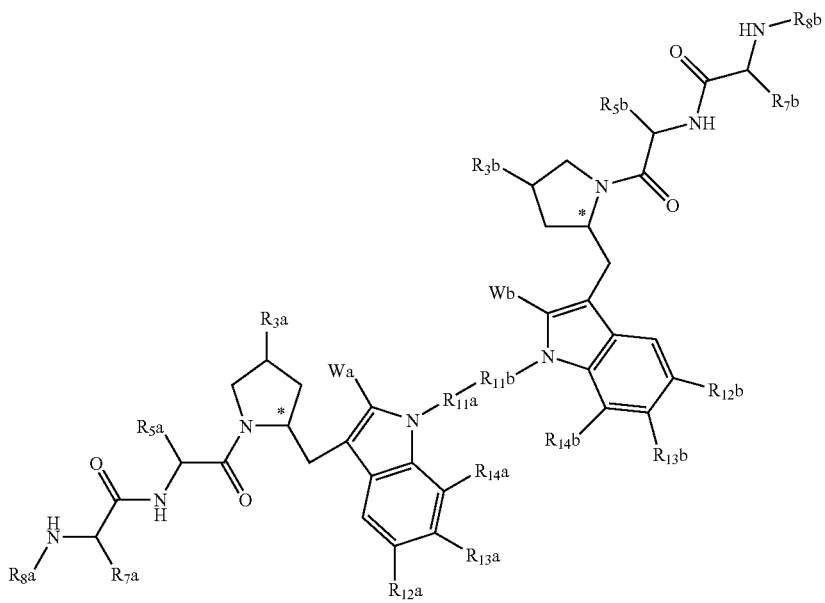

Example 10

Wherein R7a and R7b are independently H, alkyl, cycloalkyl, haloalkyl; or R8a and R7a and R8b and R7b can independently or together form a ring such as an aziridine or azetidine ring;

R8a and R8b are independently H, hydroxyl, alkyl, aryl, arylalkyl, cycloalkyl, cycloalkylalkyl, heteroaryl, or heteroarylalkyl wherein each alkyl, aryl, arylalkyl, cycloalkyl, cycloalkylalkyl, heteroaryl, and heteroarylalkyl is optionally-substituted with halogen, hydroxyl, mercapto, carboxyl, alkyl, alkoxy, amino, and nitro; or R8a and R7a and R8b and R7b can independently or together form a ring such as an aziridine or azetidine ring;

R5a and R5b are independently H, alkyl, cycloalkyl, cycloalkylalkyl, heterocycloalkyl, aryl, arylalkyl, heteroaryl, heteroarylalkyl; or each optionally-substituted with hydroxyl, mercapto, halogen, amino, carboxyl, alkyl, haloalkyl, alkoxy, or alkylthio; or, optionally, R5a and R5b are connected by an alkylene, alkenylene, alkynylene of 2 to 12 carbon atoms or optionally-substituted alkylene, alkenylene, alkynylene bridge of 2 to 12 carbon atoms where one or more carbon atoms can be replaced with N, O, or S;

R12a, R12b, R13a, R13b, R14a, and R14b are independently H, Cl, Br, F, alkyl, cycloalkyl, hydroxy, alkoxy, amino, alkylamino, cyano, or $CO_2H$;

R3a and R3b are independently H, halogen, alkyl, aryl, arylalkyl, amino, arylamino, arylalkylamino, hydroxy, alkyloxy, aryloxy, arylalkylhydroxy, dialkylamino, amido, sulfonamido, or amidino;

Wa and Wb are independently H, Cl, Br, F, alkyl, CN, $CO_2H$; and

R11a and R11b together form an alkylene, alkenylene, alkynlyene, or alkyloxyalkylene chain of 2 to 12 carbon atoms or optionally-substituted alkylene, alkenylene, alkynlyene, or alkyloxyalkylene chain of 2 to 12 carbon atoms where one or more carbon atoms can be replaced with N, O, or S.

| Entry | R8a | R7a | R5a | Wa | Wb | Stereochem at Position (*) | R11a-R11b |
|---|---|---|---|---|---|---|---|
| 147 | H | S-Me | S-iPr | H | H | S | $CH_2CH_2CH_2CH_2CH_2CH_2$ |
| 148 | Me | S-Me | S-cHex | H | H | S | $CH_2CH_2CH_2CH_2CH_2CH_2$ |
| 149 | Me | S-Me | S-tBu | H | H | S | $CH_2CH_2CH_2CH_2CH_2CH_2$ |
| 150 | H | S-Me | iPr | H | H | S | (R,R)—$CH_2CH(OH)CH(OH)CH_2$ |
| 151 | Me | S-Me | 2R-EtOH | H | H | S | (R,R)—$CH_2CH(OH)CH(OH)CH_2$ |
| 152 | Me | S-Me | 2R-EtOH | H | H | S | (S,S)—$CH_2CH(OH)CH(OH)CH_2$ |
| 153 | Me | S-Me | cHex | H | H | S | $CH_2CH_2CH_2$ |
| 154 | Me | S-Me | cHex | H | H | S | $CH_2CH_2OCH_2CH_2OCH_2CH_2$ |
| 155 | Me | S-Et | cHex | H | H | S | $CH_2CH_2OCH_2CH_2OCH_2CH_2$ |
| 156 | Me | S-Me | 2R-EtOH | H | H | S | $CH_2CH_2OCH_2CH_2OCH_2CH_2$ |
| 157 | Me | S-Et | 2R-EtOH | H | H | S | $CH_2CH_2OCH_2CH_2OCH_2CH_2$ |
| 158 | Me | S-Me | cHex | H | H | S | $C(O)CH_2CH_2C(O)$ |
| 159 | Me | S-Me | cHex | H | H | S | $C(O)C_6H_4C(O)$ |
| 160 | Me | S-Me | 2R-EtOH | H | H | S | $CH_2CH_2$ |
| 161 | Me | S-Me | 2R-EtOH | H | H | S | $CH_2CH_2CH_2CH_2$ |

| Entry | R3a | R3b | R5b | R7b | R8b | R12 | R13 | R14 | $K_D$ Range, |
|---|---|---|---|---|---|---|---|---|---|
| 147 | H | H | S-iPr | S-Me | H | H | H | H | A |
| 148 | H | H | S-cHex | S-Me | Me | H | H | H | A |
| 149 | H | H | S-tBu | S-Me | Me | H | H | H | A |
| 150 | H | H | iPr | S-Me | H | H | F | H | A |
| 151 | H | H | 2R-EtOH | S-Me | Me | H | F | H | A |
| 152 | H | H | 2R-EtOH | S-Me | Me | H | F | H | A |
| 153 | H | H | cHex | S-Me | Me | H | H | H | B |
| 154 | H | H | cHex | S-Me | Me | H | H | H | A |
| 155 | H | H | cHex | S-Et | Me | H | H | H | B |
| 156 | H | H | 2R-EtOH | S-Me | Me | H | H | H | A |
| 157 | H | H | 2R-EtOH | S-Et | Me | H | H | H | B |
| 158 | H | H | cHex | S-Me | Me | H | H | H | A |
| 159 | H | H | cHex | S-Me | Me | H | H | H | A |
| 160 | H | H | 2R-EtOH | S-Me | Me | H | H | H | A |
| 161 | H | H | 2R-EtOH | S-Me | Me | H | H | H | B |

Further Examples

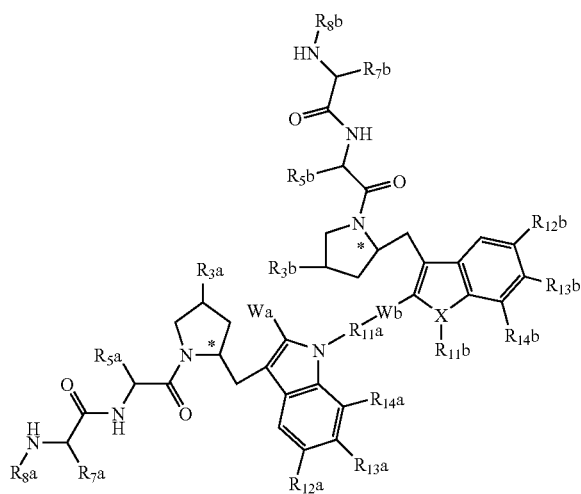

Example 11

Wherein R7a and R7b are independently H, alkyl, cycloalkyl, haloalkyl; or R8a and R7a and R8b and R7b can independently or together form a ring such as an aziridine or azetidine ring;

R8a and R8b are independently H, hydroxyl, alkyl, aryl, arylalkyl, cycloalkyl, cycloalkylalkyl, heteroaryl, or heteroarylalkyl wherein each alkyl, aryl, arylalkyl, cycloalkyl, cycloalkylalkyl, heteroaryl, and heteroarylalkyl is optionally-substituted with halogen, hydroxyl, mercapto, carboxyl, alkyl, alkoxy, amino, and nitro; or R8a and R7a and R8b and R7b can independently or together form a ring such as an aziridine or azetidine ring;

R5a and R5b are independently H, alkyl, cycloalkyl, cycloalkylalkyl, heterocycloalkyl, aryl, arylalkyl, heteroaryl, heteroarylalkyl; or each optionally-substituted with hydroxyl, mercapto, halogen, amino, carboxyl, alkyl, haloalkyl, alkoxy, or alkylthio; or, in some instances, the R5a and R5b residues are connected by an alkylene, alkenylene, alkynylene of 2 to 12 carbon atoms or optionally-substituted alkylene, alkenylene, alkynylene bridge of 2 to 12 carbon atoms where one or more carbon atoms can be replaced with N, O, or S;

R12a, R12b, R13a, R13b, R14a, and R14b are independently H, Cl, Br, F, alkyl, cycloalkyl, hydroxy, alkoxy, amino, alkylamino, cyano, or $CO_2H$;

R3a and R3b are independently H, halogen, alkyl, aryl, arylalkyl, amino, arylamino, arylalkylamino, hydroxy, alkyloxy, aryloxy, arylalkylhydroxy, dialkylamino, amido, sulfonamido, or amidino;

X is O, N, S, or C=C;

Wa is H, Cl, Br, F, alkyl, CN, $CO_2H$;

R11b is absent or H, alkyl, optionally-substituted alkyl, hydroxyalkyl, alkoxyalkyl.

Wb and R11a together are a bond, alkylene, alkenylene, alkynylene, aryl, arylalkylene, arylalkylalkylene, heteroaryl, heteroarylalkylene, or an optionally-substituted alkylene, alkenylene, alkynylene chain of 2 to 12 carbon atoms where one or more carbon atoms can be replaced with N, O, or S.

| Entry | R8a | R7a | R5a | Wa | R11b | Stereochem at Position (*) | X | Wb-R11a | R3a | R3b | R5b | R7b | R8b | R12 | R13 | R14 | $K_D$ Range |
|---|---|---|---|---|---|---|---|---|---|---|---|---|---|---|---|---|---|
| 162 | Me | S-Me | S-(2R-EtOH) | H | — | S | O | $CH_2CH_2CH_2$ | H | H | S-(2R-EtOH) | S-Me | Me | H | H | H | D |
| 163 | Me | S-Me | S-cHex | H | — | S | O | $CH_2CH_2CH_2$ | H | H | S-cHex | S-Me | Me | H | H | H | A |

In mammalian cells activation of the caspases is achieved through at least two independent mechanisms which are initiated by distinct caspases, but result in the activation of common executioner (effector) caspases. In addition to the cytochrome c activated mechanism (sometimes referred to as the 'intrinsic death pathway'), the 'extrinsic death pathway' is a mechanism by which the caspase cascade is activated via activation of a death receptor located on the cell membrane. Examples of death receptors include DR4, DR5 and TNF-R1 (as well as other members of the TNF group of cytokine receptors). The corresponding ligands are TRAIL and TNF-α, respectfully. Binding of pro-caspase-8 to the death receptor induces auto-activation wherein the inhibitory pro-domain of pro-caspase-8 is cleaved and removed. Caspase-8 is released from the receptor and can then activate effector caspases (caspase-3, -6, -7), and as in the caspase-9 initiated pathway, the result is the proteolytic cleavage of cellular targets by the effector caspases and the induction of apoptosis.

The present invention is directed generally to Smac peptidomimetics, methods of making Smac peptidomimetics and uses thereof including methods of making the peptidomimetics described above. In one embodiment of the current invention, Smac peptidomimetics (herein referred to as Smac mimetic) act as chemopotentiating agents. The term "chemopotentiating agent" refers to an agent that acts to increase the sensitivity of an organism, tissue, or cell to a chemical compound, or treatment namely "chemotherapeutic agents" or "chemo drugs" or radiation treatment. One embodiment of the invention is the therapeutic composition of a Smac mimetic. A further embodiment of the invention is the therapeutic composition of a Smac mimetic, which can act as a chemopotentiating agent and a biological or chemotherapeutic agent or radiation. Another embodiment of the invention is a method of inhibiting tumor growth in vivo by administering a Smac peptidomimetic. Another embodiment of the invention is a method of inhibiting tumor growth in vivo by administering a Smac mimetic and a biologic or chemotherapeutic agent or chemoradiation. Another embodiment of the invention is a method of treating a patient with a cancer by administering Smac mimetics of the present invention alone or in combination with a biological or chemotherapeutic agent or chemoradiation.

In a preferred embodiment of the present invention, suitable biological and chemotherapeutic agents that can be administered concurrently with Smac mimetics include alkylating agents, plant alkaloids, anti-tumor antibiotics, antimetabolites, topoisomerase inhibitors, hormonal agents, NSAIDs, growth factors, cytokines, mitotic inhibitors and combinations of these.

In another embodiment of the present invention, the cells are in situ or in an individual, and the contacting step is affected by administering a pharmaceutical composition comprising a therapeutically effective amount of the Smac mimetic wherein the individual may be subject to concurrent or antecedent radiation or chemotherapy for treatment of a neoproliferative pathology. Pathogenic cells are of a tumor such as, but not limited to, bladder cancer, breast cancer, prostate cancer, lung cancer, pancreatic cancer, gastric cancer, colon cancer, ovarian cancer, renal cancer, hepatoma, melanoma, lymphoma, sarcoma, and combinations thereof. However, the cells may also be immortalized tumor cells used in tumor cell culture.

Smac mimetics may also be used to treat autoimmune diseases. In addition to apoptosis defects found in tumors, defects in the ability to eliminate self-reactive cells of the immune system due to apoptosis resistance are considered to play a key role in the pathogenesis of autoimmune diseases. Autoimmune diseases are characterized in that the cells of the immune system produce antibodies against its own organs and molecules or directly attack tissues resulting in the destruction of the latter. A failure of those self-reactive cells to undergo apoptosis leads to the manifestation of the disease. Defects in apoptosis regulation have been identified in autoimmune diseases such as systemic lupus erythematosus or rheumatoid arthritis.

In one embodiment the pathogenic further include abnormally proliferating cells such as those of any autoimmune disease or diseases which are resistant to apoptosis due to the overexpression of IAPs or members of the Bcl-2 family of proteins. Examples of such autoimmune diseases include but are not limited to collagen diseases such as rheumatoid arthritis, systemic lupus erythematosus, Sharp's syndrome, CREST syndrome (calcinosis, Raynaud's syndrome, esophageal dysmotility, telangiectasia), dermatomyositis, vasculitis (Morbus Wegener's) and Sjören's syndrome, renal diseases such as Goodpasture's syndrome, rapidly-progressing glomerulonephritis and membrano-proliferative glomerulonephritis type II, endocrine diseases such as type-I diabetes, autoimmune polyendocrinopathy-candidiasis-ectodermal dystrophy (APECED), autoimmune parathyroidism, pernicious anemia, gonad insufficiency, idiopathic Morbus Addison's, hyperthyreosis, Hashimoto's thyroiditis and primary myxedema, skin diseases such as pemphigus vulgaris, bullous pemphigoid, herpes gestationis, epidermolysis bullosa and erythema multiforme major, liver diseases such as primary biliary cirrhosis, autoimmune cholangitis, autoimmune hepatitis type-1, autoimmune hepatitis type-2, primary sclerosing cholangitis, neuronal diseases such as multiple sclerosis, myasthenia gravis, myasthenic Lambert-Eaton syndrome, acquired neuromyotony, Guillain-Barré syndrome (Müller-Fischer syndrome), stiff-man syndrome, cerebellar degeneration, ataxia, opsoklonus, sensoric neuropathy and achalasia, blood diseases such as autoimmune hemolytic anemia, idiopathic thrombocytopenic purpura (Morbus Werlhof), infectious diseases with associated autoimmune reactions such as AIDS, Malaria and Chagas disease.

Pharmaceutical compositions encompassed by the present invention include a therapeutically effective amount of a Smac mimetic in dosage form and a pharmaceutically acceptable carrier, wherein the Smac mimetic inhibits the activity of an IAP, thus, promoting apoptosis. Another embodiment of the present invention are compositions containing a therapeutically effective amount of a Smac mimetic in dosage form and a pharmaceutically acceptable carrier, in combination with a biological or chemotherapeutic agent and/or radiotherapy, wherein the Smac mimetic inhibits the activity of an IAP, thus, promoting apoptosis and enhancing the effectiveness of the chemotherapeutic and/or radiotherapy.

Methods of making pharmaceutical compositions containing Smac mimetics are also encompassed in the present invention and include but are not limited to combining a therapeutically effective amount of the Smac mimetic with a pharmaceutically acceptable excipient.

In an embodiment of the invention a therapeutic composition for promoting apoptosis a therapeutically effective amount of a Smac peptidomimetic that binds to at least one IAP. In one embodiment the IAP can be XIAP. In another embodiment the IAP can be ML-IAP. In another embodiment the IAP can be cIAP-1 or cIAP-2. In a further embodiment the IAP can be multiple IAP types.

Embodiments of the invention also include a method of treating a patient with a condition in need thereof wherein administration of a therapeutically effective amount of a Smac peptidomimetic is delivered to the patient, and the Smac peptidomimetic binds to at least one IAP. In one embodiment the IAP can be XIAP. In another embodiment the IAP can be ML-IAP. In another embodiment the IAP can cIAP-1 or cIAP-2. In a further embodiment the IAP can be multiple IAP types. The method may further include the concurrent administration chemotherapeutic agent. The chemotherapeutic agent can be, but is not limited to, alkylating agents, antimetabolites, anti-tumor antibiotics, taxanes, hormonal agents, monoclonal antibodies, glucocorticoids, mitotic inhibitors, topoisomerase I inhibitors, topoisomerase II inhibitors, immunomodulating agents, cellular growth factors, cytokines, and nonsteroidal anti-inflammatory compounds.

Smac mimetics are preferably administered in effective amounts. An effective amount is that amount of a preparation that alone, or together with further doses, produces the desired response. This may involve only slowing the progression of the disease temporarily, although preferably, it involves halting the progression of the disease permanently or delaying the onset of or preventing the disease or condition from occurring. This can be monitored by routine methods. Generally, doses of active compounds would be from about 0.01 mg/kg per day to 1000 mg/kg per day. It is expected that doses ranging from 50-500 mg/kg will be suitable, preferably intravenously, intramuscularly, or intradermally, and in one or several administrations per day. The administration of the Smac peptidomimetic can occur simultaneous with, subsequent to, or prior to chemotherapy or radiation so long as the chemotherapeutic agent or radiation sensitizes the system to the Smac peptidomimetic.

In general, routine experimentation in clinical trials will determine specific ranges for optimal therapeutic effect for each therapeutic agent and each administrative protocol, and administration to specific patients will be adjusted to within effective and safe ranges depending on the patient condition and responsiveness to initial administrations. However, the ultimate administration protocol will be regulated according to the judgment of the attending clinician considering such factors as age, condition and size of the patient, the Smac peptidomimetic potencies, the duration of the treatment and the severity of the disease being treated. For example, a dosage regimen of the Smac peptidomimetic can be oral administration of from 1 mg to 2000 mg/day, preferably 1 to 1000 mg/day, more preferably 50 to 600 mg/day, in two to four (preferably two) divided doses, to reduce tumor growth. Intermittent therapy (e.g., one week out of three weeks or three out of four weeks) may also be used.

In the event that a response in a subject is insufficient at the initial doses applied, higher doses (or effectively higher doses by a different, more localized delivery route) may be employed to the extent that the patient tolerance permits. Multiple doses per day are contemplated to achieve appropriate systemic levels of compounds. Generally, a maximum dose is used, that is, the highest safe dose according to sound medical judgment. Those of ordinary skill in the art will understand, however, that a patient may insist upon a lower dose or tolerable dose for medical reasons, psychological reasons or for virtually any other reason.

A variety of administration routes are available. The particular mode selected will depend, of course, upon the particular chemotherapeutic drug selected, the severity of the condition being treated and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include, but are not limited to, oral, rectal, topical, nasal, intradermal, inhalation, intra-peritoneal, intravesical or parenteral routes. The term "parenteral" includes subcutaneous, intravenous, intramuscular, or infusion. Intravenous or intramuscular routes are particularly suitable for purposes of the present invention.

In one aspect of the invention, a Smac peptidomimetic as described herein, with or without additional biological or chemotherapeutic agents or radiotherapy, does not adversely affect normal tissues, while sensitizing tumor cells to the additional chemotherapeutic/radiation protocols. While not wishing to be bound by theory, it would appear that because of this tumor specific induced apoptosis, marked and adverse side effects such as inappropriate vasodilation or shock are minimized. Preferably, the composition or method is designed to allow sensitization of the cell or tumor to the chemotherapeutic or radiation therapy by administering at least a portion of the Smac peptidomimetic prior to chemotherapeutic or radiation therapy. The radiation therapy, and/or inclusion of chemotherapeutic agents, may be included as part of the therapeutic regimen to further potentiate the tumor cell killing by the Smac peptidomimetic.

In alternative embodiments of the current invention, Smac mimetics are administered in combination with a second form of therapy including but not limited to second therapy selected from radiation therapy, immunotherapy, photodynamic therapy, chemotherapy and combinations thereof.

Anti-cancer chemotherapeutic agents administered in combination with Smac mimetics may be any therapeutic agent that specifically targets tumorigenic tissue or cells and include but is not limited to alkylating agents, plant alkaloids, antitumor antibiotics, antimetabolites, and topoisomerase inhibitors including altretamine, busulfan, carboplatin, carmustine, chlorambucil, cisplatin, cyclophosphomide, dacarbazine, hexamethylmelamine, ifosfamide, lomustine, melphalan, mechlorethamine, oxaliplatin, procarbazine, streptozocin, temozolomide, thiotepa, uramustine, docetaxel, etoposide, irinotecan, paclitaxel, tenisopide, vincristine, vinblastine, vindesine, vinorelbine, bleomycin, dactinomycin, daunorubicin, epirubicin, hydroxyurea, idarubicin, mitomycin, mitoxantrone, plicamycin, azathioprine, capecitabine, cladribine, cytarabine, fludarabine, fluorouracil, floxuridine, gemcitabine, mercaptopurine, methotrexate, nelarabine, pemetrexed, pentostatin, thioguanine, camptothecan, topotecan, BNP 1350, SN 38, 9-amino-camptothecan, lurtotecan, gimatecan, diflomotecan, doxorubicin, epirubicin, idarubicin, nemorubicin, mitoxantrone, loxoxantrone, etoposide, and combinations thereof.

Smac mimetics as described herein may also be administered concurrently with immunotherapeutic agents. Immunotherapy includes the administration of an immunologically active agent selected from bacillus Calmette-Guerin (BCG), interferon, and other agents that specifically activate the immune system of affected patients and combinations thereof.

Pharmaceutical compositions. In one embodiment of the invention, an additional biological, chemotherapeutic or antineoplastic agent (infra) and/or radiation may be added prior to, along with, or following the administration of a Smac mimetic. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions are capable of being co-mingled with the molecules of the present invention, and with each other, in a manner such that there is no interaction which would substantially impair the desired pharmaceutical efficacy.

The delivery systems of the invention are designed to include time-released, delayed release or sustained release delivery systems such that the delivering of the Smac peptidomimetic occurs prior to, and with sufficient time, to cause sensitization of the site to be treated. A Smac peptidomimetic may be used in conjunction with radiation and/or additional anti-cancer chemical agents (infra). Such systems can avoid repeated administrations of the Smac peptidomimetc compound, increasing convenience to the subject and the physician, and may be particularly suitable for certain compositions of the present invention.

Many types of release delivery systems are available and known to those of ordinary skill in the art and may be used in the context of the present invention including but not limited to polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the active compound is contained in a form within a matrix such as those described in U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832,253, and 3,854,480. In addition, pump-based hardware delivery systems can be used, some of which are adapted for implantation.

Use of a long-term sustained release implant may be desirable. Long-term release, are used herein, means that the implant is constructed and arranged to deliver therapeutic levels of the active ingredient for at least 30 days, and preferably 60 days. Long-term sustained release implants are well-known to those of ordinary skill in the art and include some of the release systems described above.

The pharmaceutical compositions may conveniently be presented in unit dosage form and may be prepared by any of the methods well known in the art of pharmacy. All methods include the step of bringing the active agent into association with a carrier that constitutes one or more accessory ingredients or exipients. In general, the compositions are prepared by uniformly and intimately bringing the active compound into association with a liquid carrier, a finely divided solid carrier, or both, and then, if necessary, shaping the product.

In one embodiment of the invention, the dimeric peptidomimetics described above are combined with a pharmaceutically acceptable exipient.

Compositions suitable for parenteral administration conveniently include a sterile aqueous preparation of a chemopotentiating agent (e.g. Smac peptidomimetic), which is preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa. which is incorporated herein in its entirety by reference thereto.

Additional chemotherapeutic agents. Chemotherapeutic agents suitable for use in combination with the present invention, include but are not limited to the chemotherapeutic agents described in "Modern Pharmacology with Clinical Applications", Sixth Edition, Craig & Stitzel, Chpt. 56, pg 639-656 (2004), herein incorporated by reference in its entirety. This reference describes chemotherapeutic drugs to include alkylating agents, antimetabolites, anti-tumor antibiotics, plant-derived products such as taxanes, enzymes, hormonal agents such as glucocorticoids, miscellaneous agents such as cisplatin, monoclonal antibodies, immunomodulating agents such as interferons, and cellular growth factors. Other suitable classifications for chemotherapeutic agents include mitotic inhibitors and nonsteroidal anti-estrogenic analogs. Other suitable chemotherapeutic agents include toposiomerase I and II inhibitors, kinase inhibitors and any agent capable of activating the extrinsic or intrinsic apoptotic pathway or release of Smac from the mitochondria.

Specific examples of suitable biological and chemotherapeutic agents include, but are not limited to, cisplatin, carmustine (BCNU), 5-fluorouracil (5-FU), cytarabine (Ara-C), gemcitabine, methotrexate, daunorubicin, doxorubicin, dexamethasone, topotecan, etoposide, paclitaxel, vincristine, tamoxifen, TNF-alpha, TRAIL, interferon (in both its alpha and beta forms), thalidomide, and melphalan. Other specific examples of suitable chemotherapeutic agents include nitrogen mustards such as cyclophosphamide, alkyl sulfonates, nitrosoureas, ethylenimines, triazenes, folate antagonists, purine analogs, pyrimidine analogs, anthracyclines, bleomycins, mitomycins, dactinomycins, plicamycin, vinca alkaloids, epipodophyllotoxins, taxanes, glucocorticoids, L-asparaginase, estrogens, androgens, progestins, luteinizing hormones, octreotide actetate, hydroxyurea, procarbazine, mitotane, hexamethylmelamine, carboplatin, mitoxantrone, monoclonal antibodies, levamisole, interferons, interleukins, filgrastim and sargramostim. Chemotherapeutic compositions also include other members, i.e., other than TRAIL, of the TNF superfamily of compounds or agents such as BCG which induce synthesis of chemokines following intravesical treatment. NSAIDS may also be used in combination with the Smac mimetics of the present invention and may include selelctive and non-selective COX-2 inhibitors, celecoxib and rofecoib.

Radiotherapy protocols. Additionally, in several method embodiments of the present invention the Smac peptidomimetic therapy may be used in connection with chemo-radiation or other cancer treatment protocols used to inhibit tumor cell growth. For example, but not limited to, radiation therapy (or radiotherapy) is the medical use of ionizing radiation as part of cancer treatment to control malignant cells is suitable for use in embodiments of the present invention. Although radiotherapy is often used as part of curative therapy, it is occasionally used as a palliative treatment, where cure is not possible and the aim is for symptomatic relief. Radiotherapy is commonly used for the treatment of tumors. It may be used as the primary therapy. It is also common to combine radiotherapy with surgery and/or chemotherapy. The most common tumors treated with radiotherapy are breast cancer, prostate cancer, rectal cancer, head & neck cancers, gynecological tumors, bladder cancer and lymphoma. Radiation therapy is commonly applied just to the localized area involved with the tumor. Often the radiation fields also include the draining lymph nodes. It is possible but uncommon to give radiotherapy to the whole body, or entire skin surface. Radiation therapy is usually given daily for up to 35-38 fractions (a daily dose is a fraction). These small frequent doses allow healthy cells time to grow back, repairing damage inflicted by the radiation. Three main divisions of radiotherapy are external beam radiotherapy or teletherapy, brachytherapy or sealed source radiotherapy and unsealed source radiotherapy, which are all suitable examples of treatment protocol in the present invention. The differences relate to the position of the radiation source; external is outside the body, while sealed and unsealed source radiotherapy has radioactive material delivered internally. Brachytherapy sealed sources are usually extracted later, while unsealed sources are injected into the body. Administration of the Smac peptidomimetic may occur prior to, concurrently with the treatment protocol.

The relative binding affinity of a Smac tetrapeptide (AVPI) and a potent Smac mimetic (Entry 17) to XIAP BIR-3 is shown in FIG. 1 This figure reveals the marked increase in binding affinity, a 30,000 fold increase, of the Smac mimetic Entry 17 relative to the Smac tetrapeptide.

Figure 2:
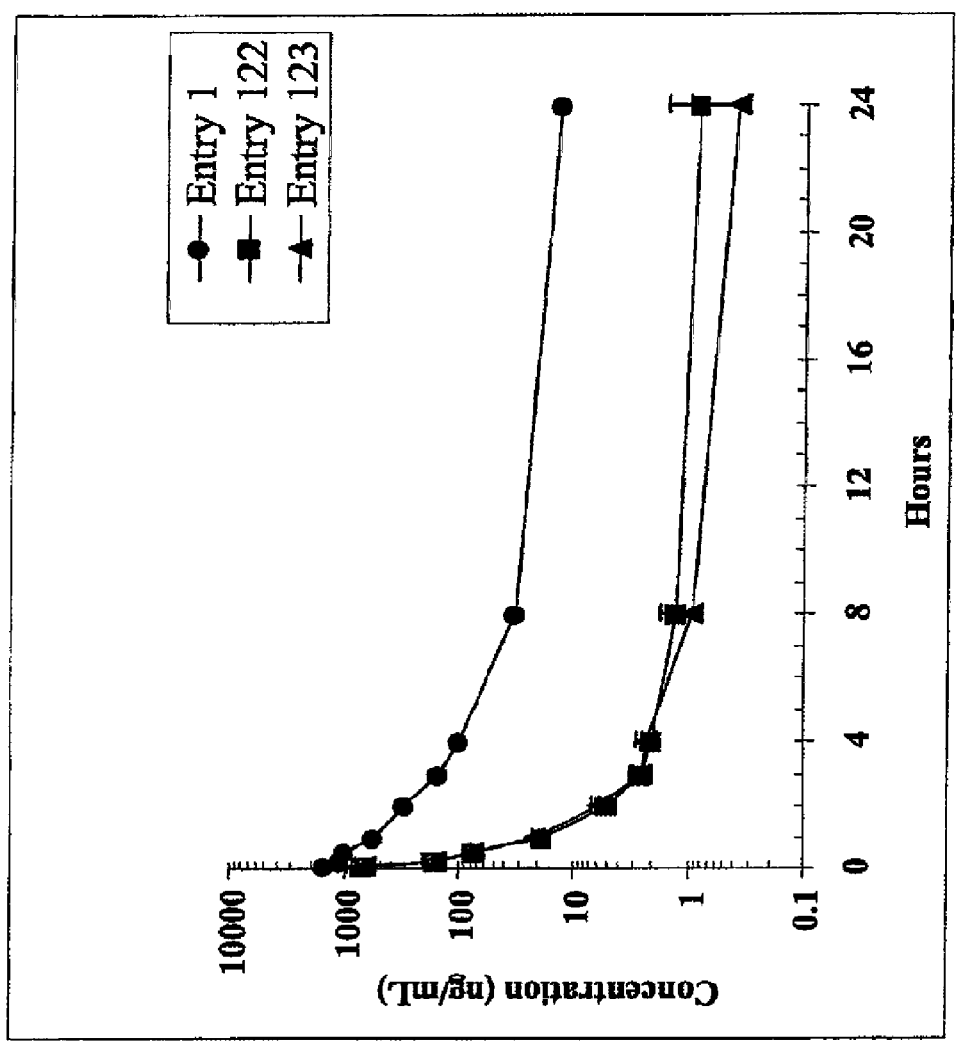
FIG. 2 is a graph showing the half life of three Smac mimetics of the present invention following a single dose intravenous administration of 1 mg/kg in a rat. Results show up to a six hour half-life for the mimetics tested.

The half life of 3 Smac mimetics, Entry 1, Entry 122 and Entry 123, was examined in a rat. The IV dose for each Smac mimetic was 1 mg/kg. FIG. 2 shows that the terminal elimination half life is up to approximately 6 hours for the Smac mimetics, with Entry 1 having the longest half-life.

Biological and chemotherapeutics/anti-neoplastic agents and radiation induce apoptosis by activating the extrinsic or intrinsic apoptotic pathways, and since Smac mimetics relieve inhibitors of apoptotic proteins (IAP's) and, thus, remove the block in apoptosis, the combination of chemotherapeutics/anti-neoplastic agents and radiation with Smac mimetics should work synergistically to facilitate apoptosis. To show the synergistic effects of Smac mimetics with common chemotherapeutic agents, a panel of diverse tumor cell lines was selected and representative compounds from various mechanistic classes of chemotherapeutics, as well as gamma radiation were tested.

A 72 hour MTT assay, as previously described by Hansen, M. B., Nielsen, S. E., and Berg, K. ((1989) *J. Immunol. Methods* 119, 203-210) and incorporated herein by reference in its entirety, was used to differentiate between a specific versus non-specific effect on cell killing by Smac mimetics. Briefly, SK-OV-3 cells were seeded in 96-well plates in McCoy's medium containing 10% fetal bovine serum albumin (20,000 per well) and incubated overnight at 37 C. The next day, test compounds were added at various concentrations (0.003-10 µM) and the plates were incubated at 37° C. for an additional 72 hrs. 50 microliters of 5 mg/mL MTT reagent was then added to each well and the plates were incubated at 37° C. for 3 hours. At the end of the incubation period, 50 microliters of DMSO was added to each well to dissolve cells and the optical density (OD) of the wells was measured using a microplate reader (Victor$^2$ 1420, Wallac, Finland) at 535 nm. Cell survival (CS) was calculated by the following equation $$CS=(OD\ treated\ well/mean\ OD\ control\ wells) \times 100\%$$

Figure 3:
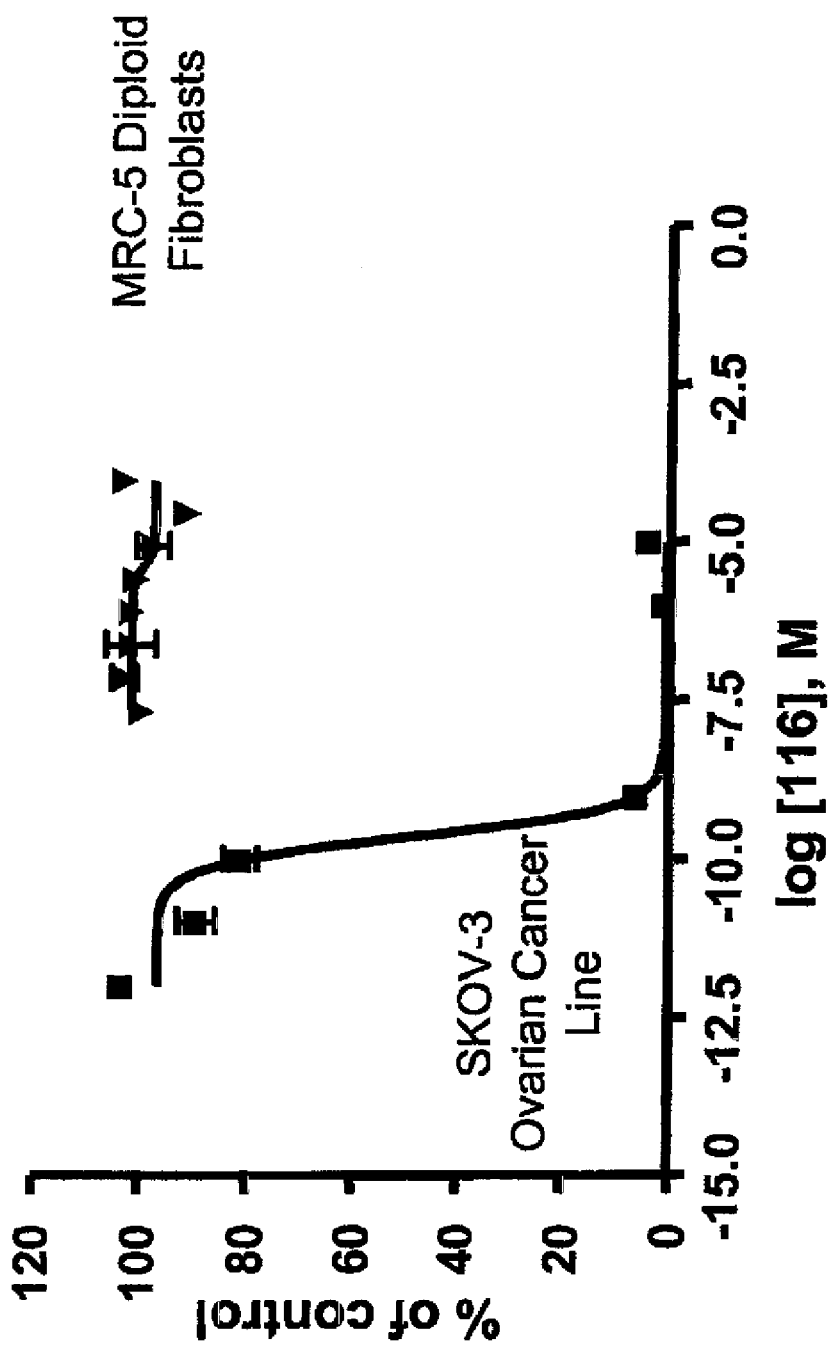
FIG. 3 is a graph showing the ability of a Smac mimetic of the present invention to selectively antagonize proliferation of an ovarian cancer cell line SK-OV-3. In this MTT assay, the Smac mimetic displays anticancer properties at concentrations that have no effect on normal diploid cell line MRC-5.

Smac mimetic Entry 116 was tested using an ovarian cancer cell line, SK-OV-3, and MRC-5 cells were used as a normal cell control. FIG. 3 shows that Entry 116 is 100,000× more effective at killing tumor cells then negative controls while normal (non-tumorigenic) cells remain unaffected.

The $EC_{50}$, defined as the drug concentration that results in 50% CS, was derived by calculating the point where the dose-response curve crosses the 50% CS point using GraphPad Prism. These results suggest that Smac mimetics that bind to XIAP can be used in the treatment of cancer either as monotherapy or in combination with chemotherapeutics.

Annexin V/Propidium Iodide Staining—To show the ability of Smac mimetics to induce apoptosis, Annexin V-fluorescein isothiocyanate staining was performed. Briefly as per manufacturer's protocol (Invitrogen, Carlsbad, Calif.), cells were exposed to various concentrations of Smac mimetics for 18-24 hrs. and then removed from the assay plate by trypsinization. Cells were then pelleted and resuspended in assay buffer (supplied by manufacturer). Annexin V and propidium iodide were added to the cell preparations and incubated for 1 hour in the dark at room temperature. Following the incubation additional buffer (200 µl) was then added to each tube, and the samples were analyzed immediately by flow cytometry. In the presence of Smac mimetics apoptosis was strongly promoted, as assessed by annexin/PI staining and analyzed by flow cytometry. The amplification in the number of apoptotic cells (Annexin V positive/propidium iodide negative–lower right quadrant) by IAP antagonists as compared to control was dose dependent and due to the induction of apoptosis and not via increasing the proportion of necrotic cells.

Figure 4:
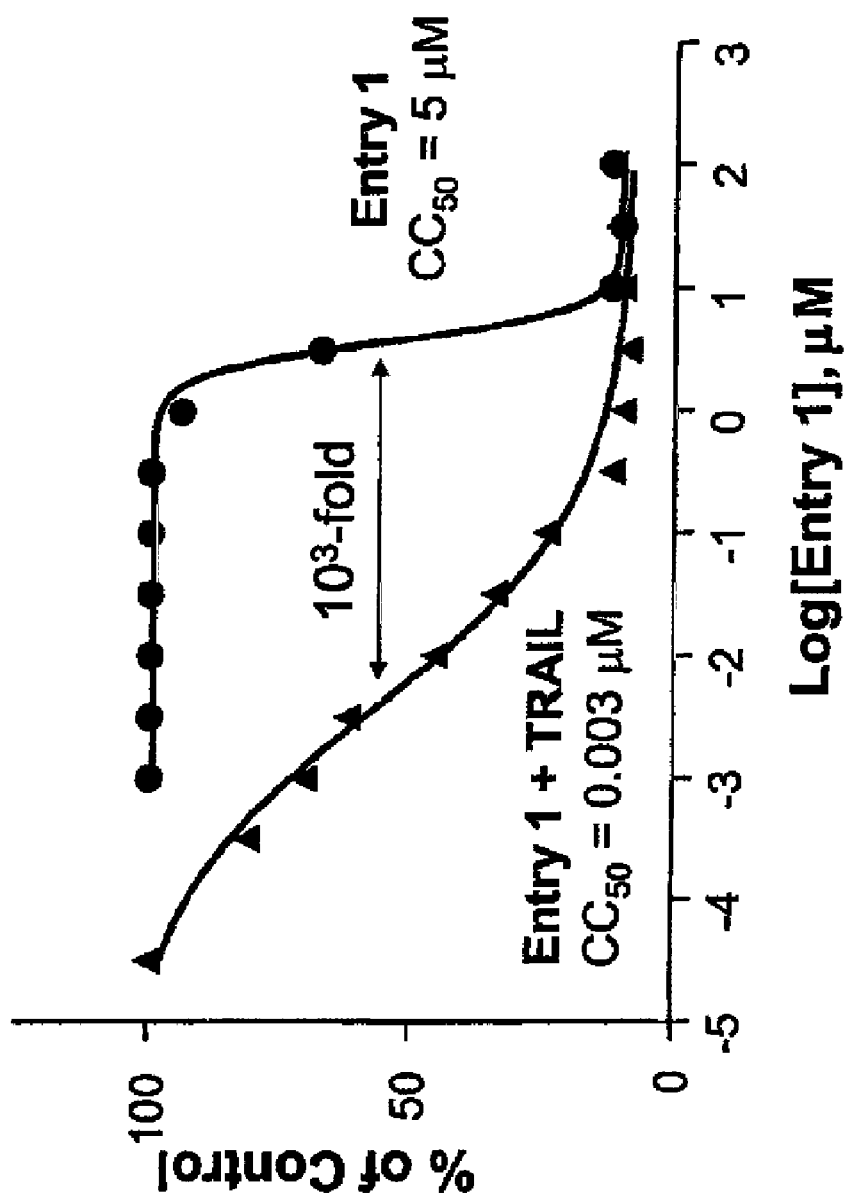
FIG. 4 shows the chemopotentiating effect Smac mimetic using melanoma cells that have been shown to be resistant to the apoptotic effects of TRAIL. Assays for cell proliferation revealed that when MDA-MB-231 cells, a breast cancer cell line, were treated with a Smac peptidomimetic of the invention Entry 1 alone the cells were resistant to the antiproliferative effects of the Smac mimetic of the invention. In contrast, when Entry 1 was used in combination with TRAIL there was a 1000 fold increase in the antiproliferative effect resulting in a 100-fold increase in the cell killing as detected by the corresponding loss in colony formation.

The chemopotentiating effect Smac mimetic using melanoma cells that have been shown to be resistant to the apoptotic effects of TRAIL, a chemotherapeutic drug (Chawla-Sarkar. Clin. Cancer Res. (2001). Assays for cell proliferation (MTT assay, FIG. 4) revealed that when MDA-MB-231 cells, a breast cancer cell line, were treated with a Smac peptidomimetic of the invention, Entry 1, alone the cells were resistant to the antiproliferative effects of the Smac mimetic of the invention. In contrast, when Entry 1 was used in combination with TRAIL there was a 1000 fold increase in the antiproliferative effect resulting in a 100-fold increase in the cell killing as detected by the corresponding loss in colony formation. A control peptidomimetic (Entry 62) failed to synergize with TRAIL and results (data not shown) indicate no anti-proliferative activity of Entry 62 alone or in combination with TRAIL. TRAIL alone induces little, if any, apoptosis of MDA MB-231 cells after 4 hours. Treatment with Entry 121 alone also failed to induce significant apoptosis (approximately 10% of cell total). In contrast, a combination of TRAIL with Entry 121 resulted in a 4 fold increase in apoptotic activity after 4 hours The ability of cells to form viable colonies was analyzed by adding various concentrations of the compound in the presence and absence of 0.4 ng/ml of TRAIL. Briefly, cells are seeded at 100 cells per well in a 12 well format in 2 ml of growth medium. The medium is removed after twenty-four hours and replaced with Smac mimetics at various concentrations in growth medium with 1% DMSO. After 72 hours on test, the concentrations are removed and replaced with 2 ml. of growth medium. The plates are returned to the incubator for 7-10 days at which time the colonies have multiplied to at least 10 cells per colony which can be counted by eye. The plates are stained with a 0.01% crystal violet solution (wt:vol. in $H_2O$) for thirty minutes. The plates are washed with tap water to remove any residual crystal violet, dried and the colonies are counted. Inhibition data were analyzed using the sigmoidal dose-response (variable slope) equation in Graph-Pad Prism (GraphPad Software, San Diego, Calif.). The 50% inhibitory concentration ($EC_{50}$) was the drug concentration that decreased the enzyme activity by 50% relative to control samples without drug.

Synergy was observed with topotecan and camptothecin, two examples of topoisomerases inhibitors in a cytotoxicity study in T98G cells. The highest amount of synergy is 50-60% more cell death than would be expected by adding together the cytotoxicity of each compound alone. Results show that both topotecan and camptothecin can act synergistically with a Smac mimetic of the invention, such as Entry 1, for an enhancement of apoptosis. The total synergistic volume was 457, with the greatest synergism being about 30%-40% more cell death than would be expected by adding together the individual Smac and topotecan cytotoxicities, between Entry 1 and a topoismerase inhibitor, such as topotecan.

To further assess potential drug-drug interactions a matrix of the permutations of two-fold serial dilutions of each drug and a Snac mimetic were tested as well as the activity of each compound alone using a program called MacSynergy II (Prichard, M. N., K. R. Aseltine, and C. Shipman, Jr. 1993. MacSynergy II. User's manual. Univ. of Michigan, Ann Arbor). The synergy with paclitaxel and the Smac peptidomimetic Entry 122 in OVCAR3 cells was tested. The highest amount of synergy detected is 10-20% which indicates greater cell death than would be expected by adding together the cytotoxicity of either compound alone.

Taxanes are compounds that inhibit mitotis by hindering depolymerization of the microtubule based spindle. These data were generated by testing various concentrations of a common taxane, paclitaxel, and a Smac mimetic. Paclitaxel the dosage ranged from about 0.0 to about 500.0 nM. For Entry 122, the dosage range was about 125.0 to about 8000.0 nM. The total synergistic volume was about 170.

The mechanism of action of platinum containing compounds is believed to be by binding to DNA and interfering with its repair mechanism, eventually leading to cell death. The synergy with cisplatin and the Smac peptidomimetics in OVCAR-3 cells was tested The highest amount of synergy is 40-50% more cell death than would be expected by adding together the cytotoxicity of each compound alone. These data were generated by testing various concentrations of cisplatin and Smac mimetics drugs. For cisplatin the dosage range was about 0.0 to about 166,500.0 nM. For Entry 122, the dosage range was about 500.0 to about 32,000.0 nM. The total synergistic volume was about 434. Similar tests were performed with the combination of carboplatin and Smac mimetics. Synergy between a Smac peptidomimetic, Entry 122, and carboplatin.

This potent synergy makes possible the use of the Smac peptidomimetics, which are IAP antagonists, to improve the efficacy of the marketed anti-tumor compounds (such as but not limited to paclitaxel, cisplatin and carboplatin). This effected will allow the lowering the required dose of the poorly tolerated anti-tumor compounds and/or by improving the responses rate at the marketed doses.

The present invention is not limited to the embodiments described and exemplified above, but is capable of variation and modification within the scope of the appended claims.

With the formula:
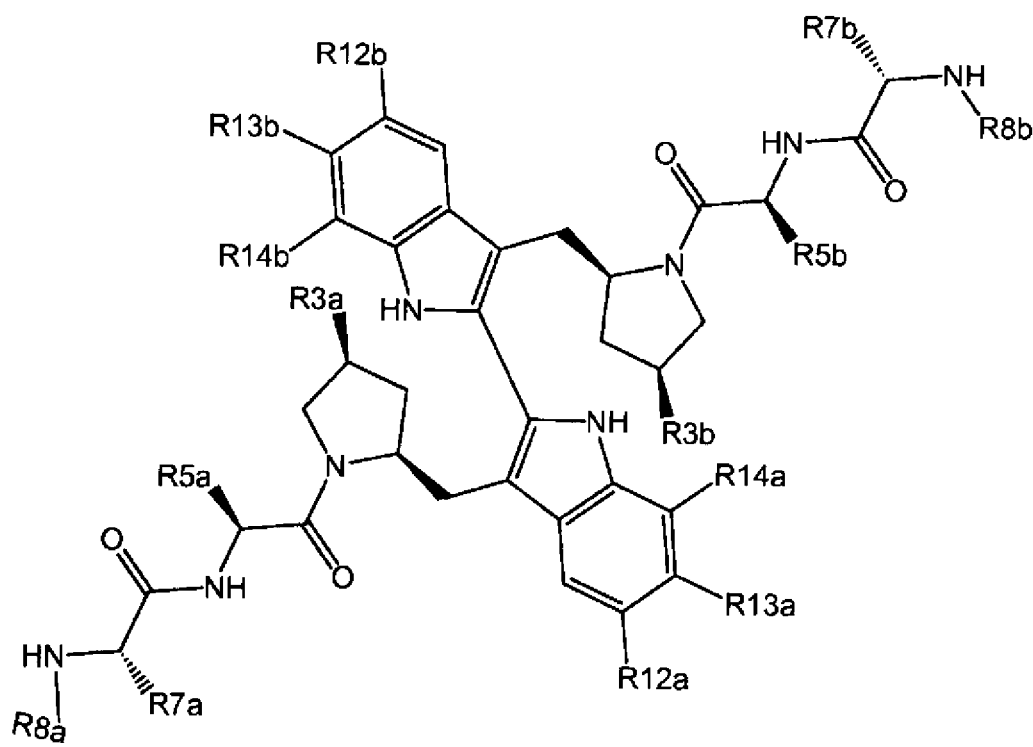

What is claimed is:
1. A compound or a pharmaceutically acceptable salt thereof, comprising formula (VII):

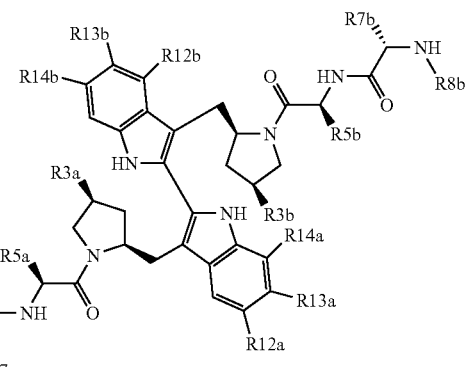

(VII)

where R5a and R5b are the same and are an alkyl, an alkyl substituted with hydroxyl, or an alkyl substituted with alkoxy;
where R7a and R7b are the same and are alkyl;
where R8a and R8b are the same and are selected from H, or alkyl;
where R3a and R3b are the same and are selected from H, or hydroxy;
where R12a, and R12b are both H;
where R13a and R13b are the same and are selected from H, or F; and
where, R14a and R14b are both H.

* * * * *

UNITED STATES PATENT AND TRADEMARK OFFICE
CERTIFICATE OF CORRECTION

PATENT NO.       : 8,022,230 B2                                              Page 1 of 2
APPLICATION NO.  : 12/403915
DATED            : September 20, 2011
INVENTOR(S)      : Stephen M. Condon et al.

It is certified that error appears in the above-identified patent and that said Letters Patent is hereby corrected as shown below:

In Column 90, lines 5-20:

Please replace the formula:

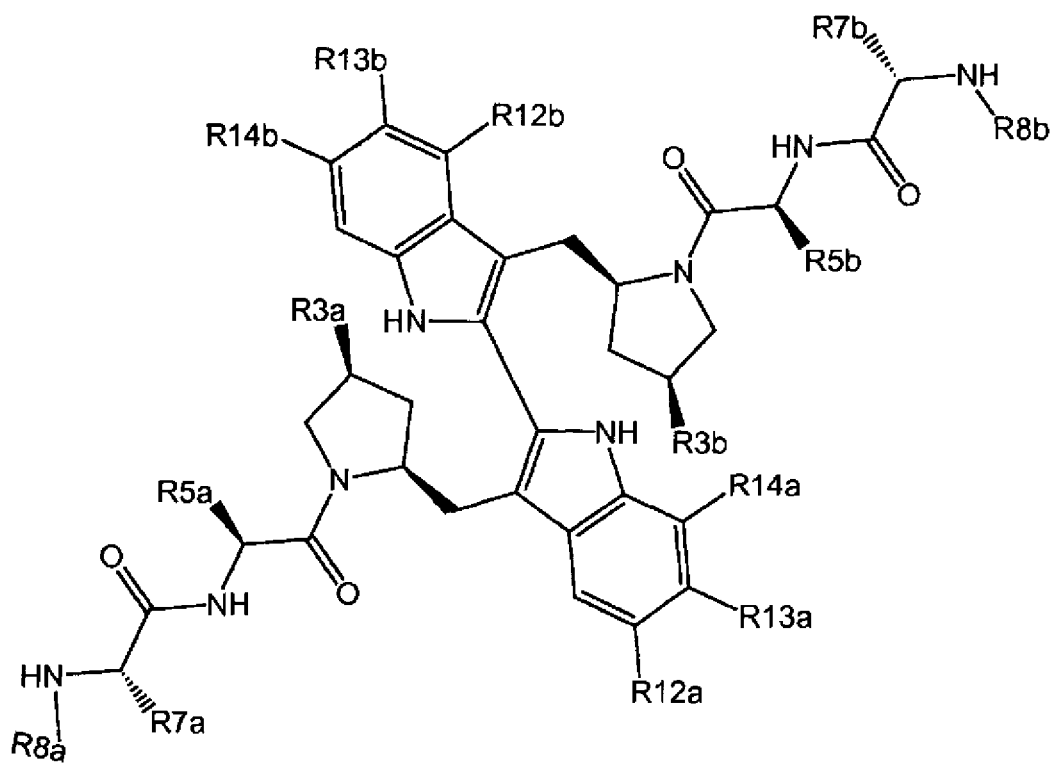

Signed and Sealed this
Third Day of July, 2012

David J. Kappos
*Director of the United States Patent and Trademark Office*